US008041416B2

(12) United States Patent
Hoium et al.

(10) Patent No.: US 8,041,416 B2
(45) Date of Patent: Oct. 18, 2011

(54) METHOD AND APPARATUS FOR DETERMINING SUSCEPTIBILITY FOR ARRHYTHMIAS USING WEDENSKY MODULATED ELECTROCARDIOGRAPHY AND ALTERNANS ANALYSIS

(75) Inventors: Harold H. Hoium, Eden Prairie, MN (US); James Brewer, Eden Prairie, MN (US)

(73) Assignee: Harbinger Medical, Inc., Eden Prairie, MN (US)

( * ) Notice: Subject to any disclaimer, the term of this patent is extended or adjusted under 35 U.S.C. 154(b) by 1008 days.

(21) Appl. No.: 11/901,695

(22) Filed: Sep. 18, 2007

(65) Prior Publication Data
US 2009/0076402 A1    Mar. 19, 2009

(51) Int. Cl.
*A61B 5/04* (2006.01)
(52) U.S. Cl. ...................................... 600/515
(58) Field of Classification Search ........... 600/515–518
See application file for complete search history.

(56) References Cited

U.S. PATENT DOCUMENTS

| | | | |
|---|---|---|---|
| 3,805,795 A | 4/1974 | Denniston et al. | |
| 4,522,194 A | 6/1985 | Normann | |
| 4,802,491 A | 2/1989 | Cohen et al. | |
| 4,969,467 A | 11/1990 | Callaghan et al. | |
| 5,117,834 A * | 6/1992 | Kroll et al. | 600/518 |
| 5,351,687 A | 10/1994 | Kroll et al. | |
| 5,487,391 A | 1/1996 | Panescu | |
| 5,555,888 A | 9/1996 | Brewer et al. | |
| 5,694,943 A | 12/1997 | Brewer et al. | |
| 5,704,365 A | 1/1998 | Albrecht et al. | |
| 5,713,367 A * | 2/1998 | Arnold et al. | 600/517 |
| 5,716,380 A | 2/1998 | Yerkovich et al. | |
| 5,735,883 A | 4/1998 | Paul et al. | |
| 5,759,158 A | 6/1998 | Swanson | |
| 5,817,130 A | 10/1998 | Cox et al. | |
| 5,951,484 A | 9/1999 | Hoium et al. | |
| 6,129,678 A | 10/2000 | Ryan et al. | |
| 6,445,947 B1 | 9/2002 | Hoium et al. | |
| 6,512,945 B1 | 1/2003 | Hoium et al. | |

(Continued)

FOREIGN PATENT DOCUMENTS

GB    2 301 037    11/1996
(Continued)

OTHER PUBLICATIONS

Medical and Biological Engineering & Computing 2002, vol. 40; Non-Invasive Wedensky Modulation Within the QRS Complex; Knathkova et al. pp. 234-240.*

(Continued)

*Primary Examiner* — Mark W Bockelman
(74) *Attorney, Agent, or Firm* — Patterson Thuente Christensen Pedersen, P.A.

(57) ABSTRACT

A method of assessing a patient's susceptibility to ventricular arrhythmia obtaining data by applying electrodes to detect electrocardiographic signal. A plurality of synchronized sub-threshold electrical stimuli are delivered into the patient's body to present stimulated cardiac cycles to the electrodes and unstimulated reference cardiac cycles to the electrodes the signals are analyzed by creating a matrix of vectorized time-phase data representing a plurality cardiac cycles contained in the electrocardiographic signals that are recorded the method includes processing the matrix to generate spectral analytic representation of the matrix, analyzing at least the spectral analytic representation to determine at least one alternans index for the patient; and displaying the at least one alternans index as an indicator of the patient's susceptibility to arrhythmia.

42 Claims, 33 Drawing Sheets

U.S. PATENT DOCUMENTS

| | | | |
|---|---|---|---|
| 6,625,483 | B2 | 9/2003 | Hoium et al. |
| 6,850,795 | B2 | 2/2005 | Hoium et al. |
| 7,016,731 | B2 | 3/2006 | Ryan et al. |
| 7,123,954 | B2 | 10/2006 | Narayan et al. |
| 7,171,265 | B2 | 1/2007 | Hoium et al. |
| 7,292,886 | B1 | 11/2007 | Kroll |
| 2007/0123787 | A1 | 5/2007 | Kitajima et al. |

FOREIGN PATENT DOCUMENTS

| | | |
|---|---|---|
| WO | WO 99/05964 | 2/1999 |

OTHER PUBLICATIONS

IEEE Transaction of Biomedical Engineering; vol. 52, No. 4, Apr. 2005; Methodological Principles of T Wave Alternans Analysis: A Unified Framework; Juan Pablo Martinez et al.; pp. 599-613.*

Journal of Cardiovascular Electrophysiology; vol. 13, No. 5, May 2002; Interpretation and Classification of Microvolt T Wave Alternans Tests; Daniel M. Bloomfield M.D. et al.; pp. 6502-6512.*

Journal of the American College of Cardiology; vol. 47, No. 2, 2006; T-Wave Alternans and the Susceptibility to Ventricular Arrhythmias; Sanjiv M. Narayan; pp. 269-281.*

J. Appl. Physiol 92: 541-549; 2002; Modified Moving Average Analysis of T-Wave Alternans to Predict Ventricular Fibrillation With High Accuracy. Bruce D. Nearing et al; pp. 541-549.*

Institute of Physics Publishing; Physiological Measurement; Physio. Meas. 26 (2005) R155-R199; Topical Review; Wavelet Transforms and the ECG: A Review; Paul S Addison; pp. R155-R199.*

Physiol. Meas. 19 (1998) 77-92; Beat -to- Beat Wavelet Variance of the QRS Complex as a Marker of Arrhythmogenic Substrate in Ventricular Tachycardia Patients; M. Popescu et al.; pp. 77-92.*

Article of Computers in Cardiology; Dated 1998; vol. 25; High Resolution ECG Filtering Using Adaptive Bayesian Wavelet Shrinkage; pp. 401-404.

Written Opinion of the International Searching Authority of PCT/US/2008/076856; Apr. 2007. Two pages.

* cited by examiner

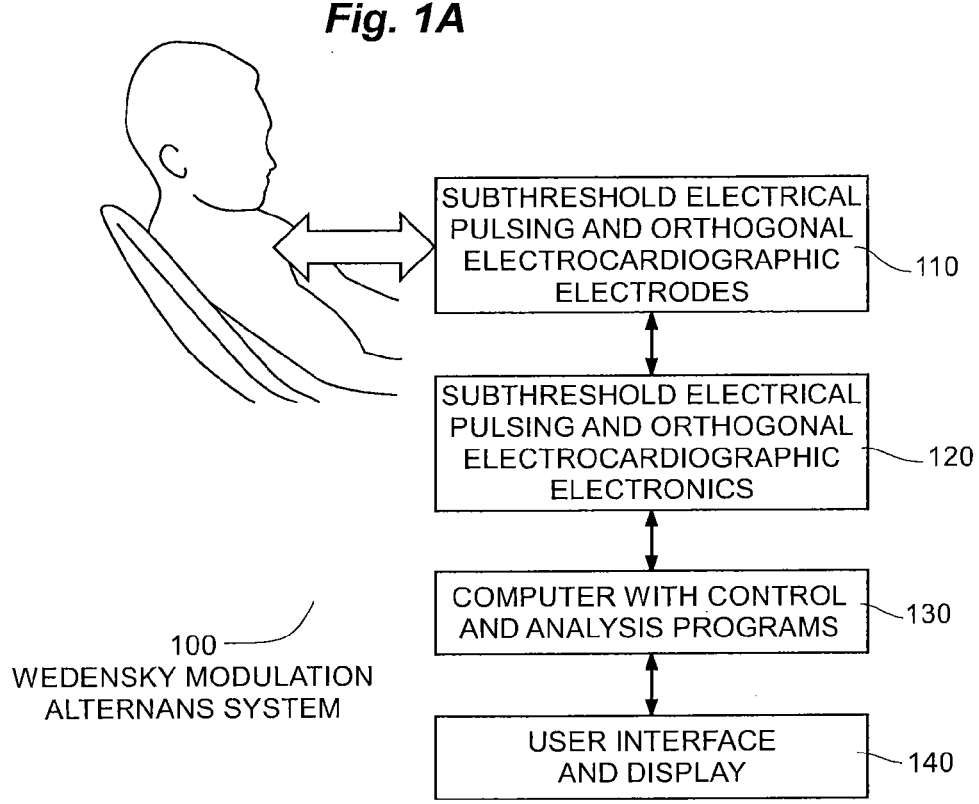

100 — WEDENSKY MODULATION ALTERNANS SYSTEM

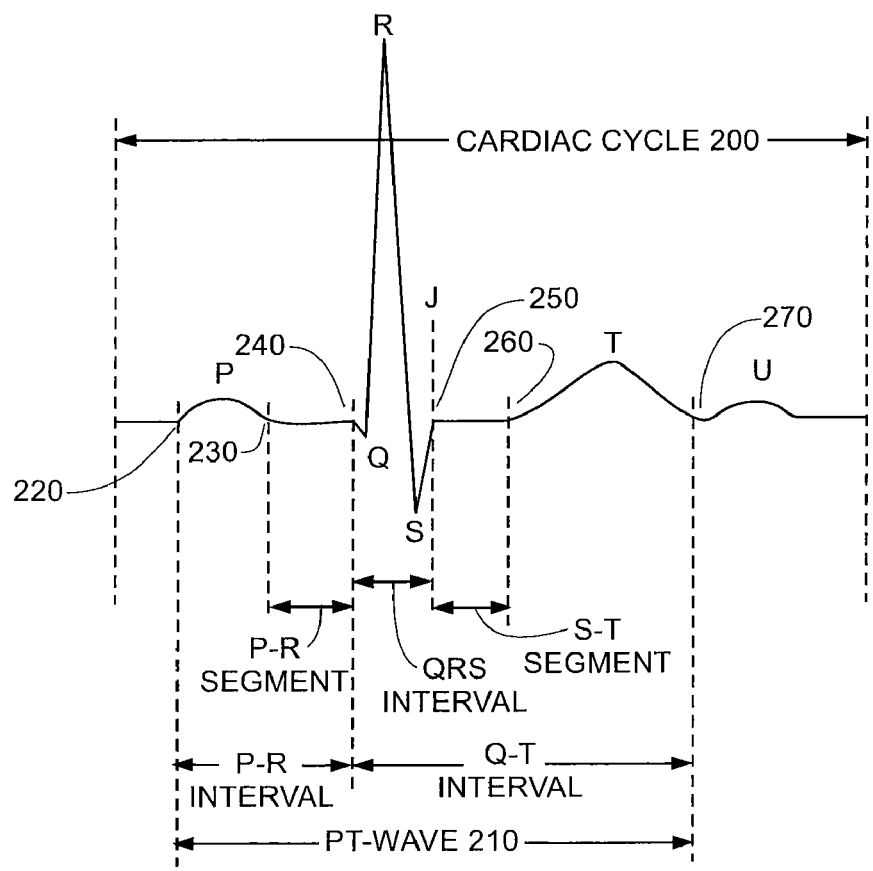

α ≤ 90 DEGREES
β ≤ 90 DEGREES
θ ≤ 90 DEGREES

α ≥ 90 DEGREES
β ≥ 90 DEGREES
θ ≥ 90 DEGREES

METHOD AND APPARATUS FOR DETERMINING SUSCEPTIBILITY FOR ARRHYTHMIAS USING WEDENSKY MODULATED ELECTROCARDIOGRAPHY AND ALTERNANS ANALYSIS

FIELD OF THE INVENTION

This invention relates generally to the detection of a patient's susceptibility to ventricular arrhythmias, to the various methods and techniques for accurately subthreshold stimulating, acquiring, and analyzing electrocardiographic signals, known as Wedensky modulation, to achieve this goal. In particular, this invention relates to the analysis of the electrical activity of a patient's heart to measure and quantify R-wave and T-wave alternans using Wedensky modulation combined with spectral methods to determine spatial and temporal dispersion relationships of myocardial depolarization and repolarization.

BACKGROUND OF THE INVENTION

There are various devices known in the art for monitoring heart function. Many of these devices typically function by analyzing signals such as an electrocardiogram (ECG) signal, which can be representative of heart function. Many methods have been developed to analyze a patient's ECG signal to diagnose whether the patient may be susceptible for sudden and life-threatening ventricular arrhythmias. Two general techniques developed to diagnose a patient for this susceptibility are the signal-averaged ECG method and the T-wave alternans method.

The Kroll and Kroll patents (U.S. Pat. Nos. 5,117,834 and 5,351,687) disclosed that a transthoracic application of subthreshold current across a patient's heart changed myocardial depolarization, that these changes were measurable in the patient's surface ECG, and that this method and apparatus would discern these changes by computing differences between vector magnitudes constructed from signal-averaged ECG signals comprising a plurality of current-injected cardiac cycles and undisturbed cardiac cycles. These methods and apparatus have been further developed in the Brewer-Taghizadeh patents (U.S. Pat. Nos. 5,555,888 and 5,694,943) and in the Hoium-Ryan-Malik patents (U.S. Pat. Nos. 5,951,484, 6,129,678, 6,445,947, 6,512,947, 6,625,483, and 6,850,795). These methods and apparatus have been shown to significantly improve patient diagnosis compared to conventional signal-averaged ECG methods.

The Cohen and Smith patent (U.S. Pat. No. 4,802,491) disclosed a passive method to detect subtle alternations in the morphologic features of the ECG, known as microvolt T-wave alternans (MTWA), to determine a patient's increased risk for life-threatening arrhythmias. Their method and apparatus was determined to provide a capability equivalent to general signal-averaged ECG methods. To generate a significant level of diagnostic alternans information, an important element to using the MTWA technology requires the measurements for MTWA to be drawn from a patient's recorded ECG signals derived during the course of an exercise stress procedure for the patient, and as such the MTWA technology may be limited in its application and utility because of the inability of many cardiac patients to participate in exercise induced stress or the risk that they will be harmed by it.

A recently published review (Haghjoo M, et al, Microvolt T-wave alternans: A review of techniques, interpretation, utility, clinical studies, and future perspectives, Internat Jour Cardiol 2006; 109; 293-306) carefully delineates the technical limitations to MTWA testing: (1) MTWA cannot be measured in patients with a trial fibrillation, a common arrhythmia in patients with structural heart disease, (2) the presence of frequent atrial and ventricular ectopy, excessive motion artifacts, and inability to reach a target heart rate render the results indeterminate, (3) the accuracy of MTWA testing is reduced in patients with prolonged QRS complex, (4) the spectral methods for MTWA do not perform well soon after an acute myocardial infarction, and (5) exercise MTWA testing may be impossible in subgroups of patients who are not able to perform bicycle or treadmill testing.

Further, as a clinical example regarding this appraisal, recent research has been published showing that there were a significant higher number of patients with sustained MTWA and a significantly lower number of patients with an indeterminate test when using simultaneous ventricular and atrial pacing in patients following myocardial infarction when compared to the same patients when using bicycle based exercise stress testing (Raatikainen M J P, et al, Microvolt T-wave alternans during exercise and pacing in patients with acute myocardial infarction, Pacing Clin Electrophysiol 2005; 28: S193-S197). Such clinical results continue to illustrate the truly demanding procedures required to support the application and accuracy of the MTWA as it is presently practiced.

Despite the need in the art for an ECG apparatus or methods which overcome the shortcomings and limitations of the prior art, none insofar as is known has been developed or proposed.

SUMMARY OF THE INVENTION

The present invention eliminates or reduces the need to subject the cardiac patient to exercise or pharmacological stress for the purpose of testing cardiac function. By replacing the physically challenging exercise stress procedure (or its pharmacological equivalent) with an easy-to-apply, non-invasive, non-exertional subthreshold pulsing procedure, called Wedensky modulation, a patient may be tested regardless of the patient's physical ability to walk or run, thereby determining a susceptibility index for the patient. Further, a patient may be tested without cause for concern regarding any cardiac or other related health issues due to aftereffects of an exercise or pharmacological stress procedure.

Accordingly, the present invention provides an active ECG method and apparatus that applies the clinical science related to Wedensky modulation and its associated diagnostic capabilities focused on spectral methods of microvolt T-wave alternans.

The invention includes a method and apparatus for assessing a patient's susceptibility to ventricular arrhythmia including obtaining data by applying electrodes to the patient. The electrodes are adapted to detect electrocardiographic signals from the patient and to selectively delivering a plurality of subthreshold electrical stimuli into the patient's body that are synchronized to a plurality of selected cardiac cycles. This presents stimulated cardiac cycles to the electrodes such and other unselected cardiac cycles that are unstimulated. The electrodes to record a plurality of the electrocardiographic signals including the stimulated cardiac cycles and the unstimulated reference cardiac cycles. The recorded electrocardiographic signals are analyzed by creating a matrix of vectorized time-phase data representing a plurality cardiac cycles contained in the electrocardiographic signals. Next the matrix is processed to generate spectral analytic representation of the matrix. At least the spectral analytic representation is analyzed to determine at least one alternans index for the patient. The alternans index is displayed as an indicator of the patient's susceptibility to arrhythmia.

In one aspect of the invention, the method and apparatus include constructing at least two stimulated time phase matrices from the stimulated cardiac cycles including at least one stimulated time phase matrix for each electrocardiographic signal and constructing at least two reference time phase matrices from the reference cardiac cycles including at least one reference time phase matrix for each electrocardiographic signal then computing a stimulated vector magnitude time phase matrix from the stimulated time-phase matrices from the stimulated time-phase matrices. Next, a reference vector magnitude time phase matrix is computed from the reference time-phase matrices. Power spectra are computed for each phase dimension column in each stimulated time phase matrix and each phase dimension column in the stimulated vector magnitude time phase matrix and for each phase dimension column in each reference time phase matrix and each phase dimension column in the reference vector magnitude time phase matrix. The method also includes: constructing alternans energy curves for each stimulated time phase matrix and each stimulated vector magnitude time phase matrix; constructing alternans energy curves for each reference time phase matrix and each reference vector magnitude time phase matrix; computing stimulated alternans indices from the stimulated alternans energy curves; computing reference alternans indices from the reference alternans energy curves; and computing comparative alternans indices by comparing the stimulated alternans indices and the reference alternans indices thereby assessing the patients susceptibility to arrhythmias.

In another aspect of the invention analyzing further includes performing wavelet analysis of the stimulated and reference alternans energy curves.

In another embodiment, analyzing includes computing a stimulated wavelet transform for at least one of the stimulated alternans energy curves, computing a reference wavelet transform for at least one of the reference alternans energy curves, computing a difference for at least one stimulated and reference wavelet transforms to derive for at least one wavelet residuum surface, computing a plurality of wavelet residuum surface area elements; and displaying a graph of the for at least one wavelet residuum surface graph, and a plurality of surface area elements.

Analyzing may also include processing the matrix in a batch mode or processing the matrix in an interleaved mode.

Analyzing may also include constructing a plurality of interleaved stimulated-reference time-phase matrices from the recorded stimulated cardiac cycles and unstimulated reference cardiac cycles, one interleaved stimulated-reference time-phase matrix for each orthogonal electrocardiographic signal then computing an interleaved stimulated-reference vector magnitude time-phase matrix from the interleaved stimulation-reference time-phase matrices. The method may also include computing power spectra for each phase dimension column in each interleaved stimulated-reference time-phase matrix and each phase dimension column in the interleaved stimulated-reference vector magnitude time-phase matrix and constructing differential alternans energy curves for the interleaved stimulated-reference time-phase matrices and the interleaved stimulated-reference vector magnitude time-phase matrix; and computing differential alternans indices from the differential alternans energy curves thereby assessing the patients susceptibility to arrhythmias.

Analysis may also include performing wavelet analysis of the differential alternans energy curves.

For example analyzing may further include computing Morlet wavelet based wavelet transforms of the alternans energy curves of the interleaved stimulated-reference time-phase matrix and the interleaved stimulated-reference vector magnitude time-phase matrix; and computing alternans indices derived from combination methods related to wavelet packet tiling.

An embodiment on the invention includes applying Fourier transform methodology to the process. Analysis may also include applying continuous wavelet transform methods such as applying continuous wavelet transform methods comprises applying a continuous wavelet transform. The wavelet transform methods may include applying a discrete wavelet transform or applying a wavelet packet transform.

Another aspect of the invention includes applying a weighting scheme using a multiresolution algorithm and a wavelet packet transform to a wavelet tiling representation. The weighting scheme may include sorting wavelet packet coefficients from largest value to smallest value, selecting a plurality of coefficients larger than a predetermined coefficient threshold value, and summing the selected coefficients to form an alternans energy curve index. Alternately, the weighting scheme includes computing an entropy value for each wavelet packet coefficient, sorting wavelet packet coefficient entropy values from smallest to largest, selecting a plurality of coefficients smaller than a predetermined entropy threshold value, and summing the selected coefficients to form an alternans energy curve index Another aspect of the invention includes eliminating data for outlier cardiac cycles in pairs.

The invention also may include delivering the subthreshold cardiac signal to an R-wave of the electrocardiographic signals, a T-wave of the electrocardiographic signals or a P-wave of the electrocardiographic signals.

BRIEF DESCRIPTION OF THE DRAWINGS

FIG. 1A illustrates a patient being tested with an embodiment of a Wedensky modulation system in accordance with the invention, including pulsing and electrocardiographic leads and electrodes attached to electronics, computer, and software programs.

FIG. 2 illustrates a patient's cardiac cycle and PT-wave, including the P-wave, R-wave, and T-wave, and their relationships to various timing markers.

DETAILED DESCRIPTION OF THE DRAWINGS

Figure 1B:
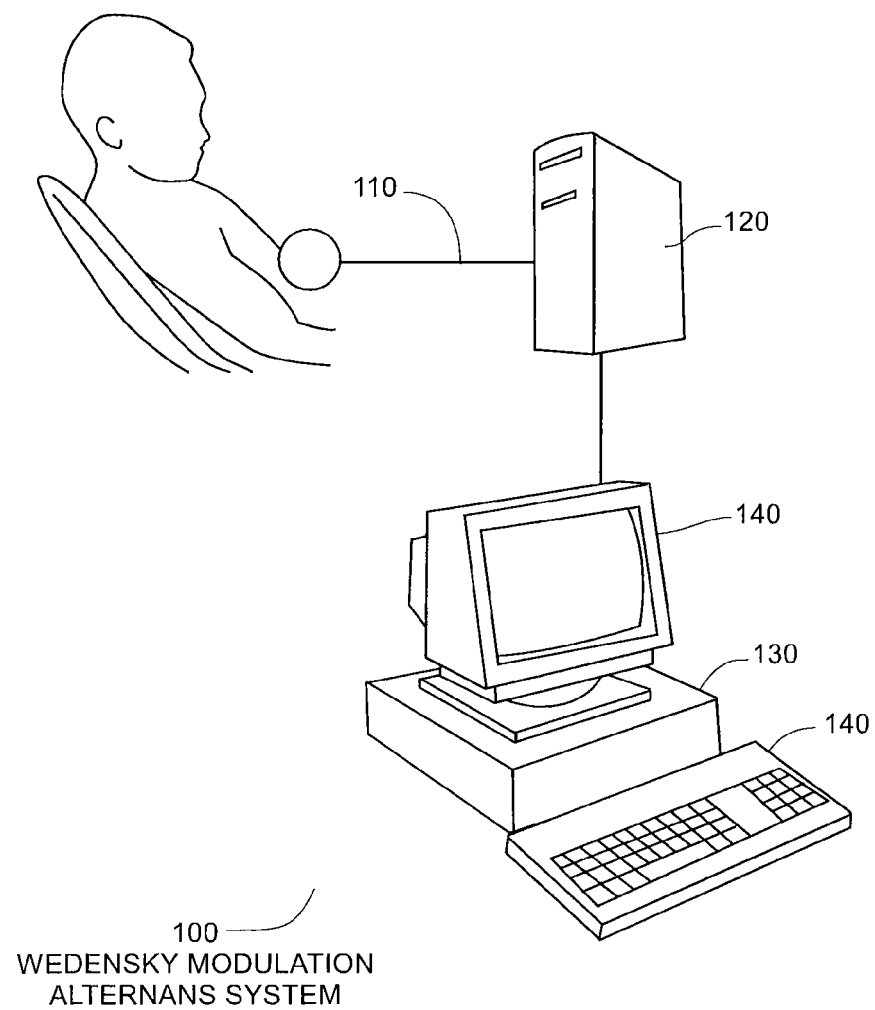
FIG. 1B illustrates a patient being tested with another embodiment of a Wedensky modulation system in accordance with the invention, including pulsing and electrocardiographic leads and electrodes attached to electronics, computer, and software programs.

FIGS. 1A and 1B illustrate an embodiment of the present invention, called the Wedensky modulation alternans system 100, and including a general purpose computing machine (computer) 130, interface units 140 such as a keyboard (as a data and command entry unit), a mouse (as a data and command control unit), and a screen (as a data output and display unit) connected to the computer, an electronic interface 120 that is physically and electronically connected to the computer and that is connected to a plurality of electrodes 110 which are adapted to be connected to a patient, and software 130 operating in the computer 130 and connected to the invention's listed physical elements using input/output (I/O), process, control, command, and interface capabilities.

One aspect of the present invention provides a diagnostic test capability to a user, typically a medical professional, to perform a plurality of diagnostic Wedensky modulation alternans tests involving observing and analyzing of a series of cardiac cycles derived from a patient's electrocardiograph (ECG). During a test, a plurality of the cardiac cycles are stimulated by one or more subthreshold pulses of electrical current derived from the electronic monitoring and pulsing interface. These cycles are referred to as stimulated cardiac cycles. Further, during a test, a plurality of the cardiac cycles are not stimulated by any externally applied energy. These cycles are referred to as reference cycles. Various representations of these two different sets of cardiac cycles are compared and the differences are analyzed to detect a patient's susceptibility to life-threatening cardiac arrhythmias.

Example methods and apparatus are disclosed for accomplishing transthoracic subthreshold pulsing, comparison of ECG changes in relation to subthreshold pulsing, using associated analysis, algorithms, display, printing, and reporting functions.

The present invention may make use of methods and apparatus such as those disclosed in U.S. Pat. No. 5,117,834 issued to Kroll et al, U.S. Pat. No. 5,555,888 issued to Brewer et al, and in U.S. Pat. Nos. 5,951,484, 6,445,947, and 6,512,947 issued to Hoium et al, the detailed description and Figures of which are hereby incorporated herein by reference in their entireties.

The present invention records electrocardiographic (ECG) signals from a patient using an orthogonal lead system, such as, for example, the Frank lead system (Frank E, An accurate clinically practical system for spatial vectorcardiography, Circulation 1956; 13: 737; the disclosure of which is incorporated herein by reference in its entirety). An orthogonal lead system comprises several electrical leads that are connected to the computer and that are connected to a patient. An orthogonal lead system, which comprises the electrodes connected to a patient, the wires connected to the electrodes and connected to the ECG and pulsing circuitry in the computer, and the control and data processing software elements that reside in the computer and are connected to the ECG and pulsing circuitry, is described in detail in the incorporated U.S. Pat. No. 6,512,947 reference.

The lead system serves at least two purposes. First, in one aspect of the invention the lead system and its pulsing circuitry and software pulsing control elements are used to apply electrical pulses across the chest of the patient at one or more pre-determined and synchronized timing points during a cardiac cycle for a pre-selected number of cardiac cycles that occur during a diagnostic Wedensky modulation testing episode. These short and subthreshold pulses of current are introduced by the invention at a predetermined timing point in a cardiac cycle for a plurality of cardiac cycles which have been designated as the cardiac cycles to be stimulated. The timing point is located between the P-wave and the start of the T-wave of the cardiac cycle. The current for the subthreshold pulses is equal to or less than about 100 mA and the duration for the subthreshold pulses is equal to or less than about 100 ms. The application of subthreshold pulses to a predetermined subset of a patient's cardiac cycles during the time when the patient is tested is called Wedensky modulation.

In general, the present invention is not restricted to orthogonal lead systems. For each lead pair of a lead system that is connected to a patient, there is an associated electrical vector. The electrical vector, also called a lead vector, is related to the heart dipole, such that the projection of the heart dipole onto the electrical vector times its length yields a potential difference as measured between the leads of a lead pair. When this potential lead difference is measured and recorded by the present invention, it is an electrocardiographic (ECG) signal. For example, a typical vectorcardiographic system has three lead pairs that measure and record three orthogonal electrical vectors. In the present invention, electrical vectors need not to be parallel to anatomic body axes, mutually perpendicular to one another, nor equal in length.

Figure 32A:
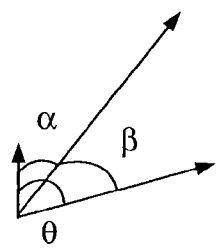
FIG. 32A illustrates an example electrical vector arrangement according to an embodiment of the invention.
Figure 32B:
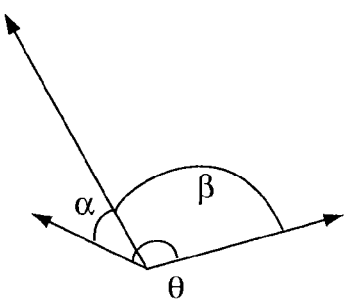
FIG. 32B illustrates another example electrical vector arrangement according to an embodiment of the invention.

In the present invention, it is only required that electrical vectors are linear independent as a set of vectors when measured and recorded by associated lead pairs (FIGS. 32A and 32B) and that the electrodes connecting each lead pair to a patient (and thereby associating an electrical vector to the lead pair) are placed in the same anatomical locations from one patient to the next. The first requirement provides a unique and reproducible frame of reference for the heart dipole from patient to patient. The second requirement promotes a minimum of variation due to a change in the anatomic location of the heart dipole from one patient to another, while at the same time providing quantitative electrocardiographic information measured on a patient's body surface.

In the present invention, using a selection menu provided by the invention's interface, a physician-operator selects the lead system in terms of rectangular (Cartesian) coordinates, cylindrical coordinates, circular cylindrical coordinates, elliptic cylindrical coordinates, parabolic cylindrical coordinates, spherical coordinates, oblate spheriodal coordinates, prolate spheriodal coordinates, parabolic coordinates, and general orthogonal and non-orthogonal curvilinear coordinates.

For the purposes of this application, a cardiac cycle that is subjected to a subthreshold pulse at some time during its cycle is called a stimulated cardiac cycle, and when associated with descriptors for a cardiac cycle the modifier "stimulated" indicates that the description of the invention structures and operations are referring to a stimulated cardiac cycle. Similarly, for the purposes of this application a cardiac cycle that is not subjected to a subthreshold pulse at any time during its cycle is called a reference cardiac cycle, and when associated with descriptors for a cardiac cycle the modifier "reference" indicates that the description of the invention structures and operations are referring to a reference cardiac cycle.

Second, the lead system is used by the present invention and its ECG data acquisition circuitry and software data acquisition control elements to sense and acquire one or more ECG data streams including reference and stimulated cardiac cycles measured from the patient. During the process of acquiring the ECG data streams, three ECG signals, measured as potential differences between pre-determined electrode pairs, are constructed and digitized, which are designated by the letters X, Y, and Z. Each ECG signal is sampled simultaneously and at the same rate. The sampling rate per ECG signal is a selectable and pre-determined rate between about $1*10^2$ samples per second and $1*10^9$ samples per second. Prior to digitizing the ECG signal data using a simultaneous sample-and-hold process, the present invention's circuitry filters the analog ECG signal components for Nyquist criteria. The filter circuitry provides anti-aliasing filtering that ranges from $1*10^{-2}$ Hz to $1*10^4$ Hz. The present invention operates using the default settings for a sampling rate of $1*10^3$ samples per second and for a frequency range from $5*10^{-2}$ Hz to $5*10^2$ Hz. Selectable anti-aliasing filter settings and signal sampling rates are available to an operator and are preset by the operator prior to testing a patient. The data for each recorded ECG signal is stored within the computer, either into the computer's memory or onto one or more of the computer's hard disk drives.

The ECG signals are the three orthogonal components of the human heart dipole, comprising an accurate system of spatial vectorcardiography employing the seven electrodes of the present invention, including a combination of reference and stimulated cardiac cycles, and enabling quantitative analysis of these ECG signals as describe herein. The present invention, as an improved electrocardiographic system, is re-configurable to record and analyze the standard electrocardiography leads, comprising the limb leads I, II, and III, the augmented limb leads aVR, aVL, and aVF, and the six precordial leads $V_1, V_2, V_3, V_4, V_5$, and $V_6$. The invention is also re-configurable to record and analyze a plurality of non-standard precordial leads, for example the $V_{R1}, V_{R2}, V_{R3}, V_{R4}$, $V_7, V_8, V_9$, and $V_{10}$ leads, such that these and various other recorded electrocardiographic signals comprise a combination of reference and stimulated cardiac cycles. The methods and apparatus of the present invention are equally applicable to these and various other electrocardiographic signals that have been Wedensky modulated. The detailed description of the present invention will emphasize the orthogonal ECG signals that have now been described; however, the description provides examples with respect to Wedensky modulated and recorded ECG signals and this should not be considered limiting. Details to the description of electrocardiography methods and its applications, various supporting lead systems, and the interpretation of ECG signals can be found in the well-known Marriott reference (Wagner G S, Marriott's Practical Electrocardiography, $9^{th}$ edition, Williams and Wilkins, Baltimore, Md. 21202 USA, 1994).

For each stored ECG signal and for each cardiac cycle in the stored ECG signal, morphological features are identified and marked by operating the present invention's software morphological feature detection and analysis program residing in the computer, as described in detail in the incorporated U.S. Pat. No. 6,512,947 reference. FIG. 2 illustrates an example cardiac cycle 200 and example PT-wave 210. For each cardiac cycle, these morphological features include such features as the P-wave, the R-wave (also known as the QRS complex), the ST segment, and the T-wave. For each morphological feature that is identified in a cardiac cycle, one or more timing markers 220, 230, 240, 250, 260, and 270 are assigned to the feature. A timing marker represents a location of a part of a morphological feature and corresponds to a fiducial alignment point for the feature. Specific to each cardiac cycle, the R-wave is detected, counted, and marked with one or more timing markers. Following the R-wave detection process, the present invention has a count of the number of R-waves, and therefore the number of cardiac cycles, that exist in each ECG signal.

Since each ECG signal is constructed using accurate simultaneous sample-and-hold acquisition electronics and circuitry for the ECG signals acquired from a patient, the timing markers for the features for one ECG signal can serve as the timing markers for other ECG signals that were electronically acquired and stored during the same time period, and each ECG signal has the same number of features for each cardiac cycle. The common number of detected R-waves for the ECG signals is herein labeled N and describes the total number of R-waves. The total number of R-waves is separated into two subsets of detected R-waves, the first set of detected R-waves associated with the reference cardiac cycles and the second set of detected R-waves associated with the stimulated cardiac cycles. The number of detected R-waves for the reference cardiac cycles for the ECG signals is herein labeled $N_R$ and the number of detected R-waves for the stimulated cardiac cycles for the ECG signals is herein labeled $N_S$. The construction and recording of storage location pointers to the reference cardiac cycles and to the stimulated cardiac cycles is described in detail in the incorporated U.S. Pat. No. 6,512,947 reference and are used by the present invention to differentiate between the two types of cardiac cycles in each ECG signal. In particular, the incorporated U.S. Pat. No. 6,512,947 reference describes the details regarding the electronic circuitry, software control elements, and their connection and operation to acquire and construct the ECG signals that are stored within the computer. In particular, the present invention operates filtering steps, baseline removal steps, steps to remove cardiac cycles representing ventricular arrhythmias, and steps to remove overly noisy cardiac cycles similar to that described in U.S. Pat. No. 6,512,947.

Further, in one aspect the present invention augments the removal of cardiac cycles by removing cardiac cycles in pairs. In one aspect of the invention, each ECG signal is processed for the removal of arrhythmic cardiac cycles and noisy cardiac cycles, herein labeled outlier cardiac cycles.

In contrast to the prior art, which teaches the exclusion of individual outlier cardiac cycles when they are detected during the course of pre-processing an ECG signal in preparation for analyzing the signal for T-wave alternans, the inventors have discovered that cardiac cycle pairs, which include the outlier cardiac cycle, should be excluded instead of excluding only the individual outlier cardiac cycles. The exclusion of cardiac cycle pairs permits a correct analysis of a patient's ECG signals for two important reasons. The first reason is clinical: the clinical nature of T-wave alternans and the prior art's description of their subsequent measurement, relies on an alternating cardiac cycle. In detail, clinically measurable T-wave alternans occur over the time period of two cardiac cycles and these alternans are directly and compellingly tied to this cardiac cycle pair. The second reason is technical: the time-frequency analysis performed on the phase dimension data requires that the alternating cardiac cycle positions create alternans patterns that cannot be disrupted without significant (and possibly destructive) aliasing effects on the information content in the analysis derived from a Fourier transform. Therefore, the removal of an outlier cardiac cycle requires the removal of the other cardiac cycle member of the pair. For these and other reasons that will become clear and will be appreciated with reference to the detailed description, the present invention applies this understanding to the operation of pre-processing an ECG signal for outlier cardiac cycles.

At the start of pre-processing an ECG signal, the present invention tracks consecutively occurring cardiac cycle pairs, and removes the pair of cardiac cycles if one or both of the cycles are determined to be outlier cardiac cycles. In this manner, the essential clinical characterization of T-wave alternans is preserved. The preservation of this clinical characterization will be best appreciated with reference to the detailed description of the invention embodiments described below.

Specific to a detected R-wave, a timing marker 220 is associated with the P-wave prior to the start of the R-wave, and is called the P-wave starting time. Specific to a detected R-wave, a timing marker 270 is associated with the T-wave following the end of the T-wave, and is called the T-wave ending time. The T-wave timing marker for the T-wave ending time is located at the same point in time in a cardiac cycle as measured from the P-wave starting time for each cardiac cycle in each ECG signal. The global maximum difference in time from the P-wave starting time to the T-wave ending time is herein labeled M. The value M represents the longest time length from a P-wave starting time to a T-wave ending time, where a PT-wave's length is its T-wave ending time minus its P-wave starting time, for all PT-waves that are extractable from a patient's ECG signals. The value M is used to construct the present invention's time-phase matrices so that all time-phase matrices have the same time-dimension length.

Additional example cardiac cycle feature detection and time marking methodologies are described and illustrated in the methods and apparatus of U.S. Pat. No. 3,590,811, issued to Harris, and U.S. Pat. No. 5,758,654, issued to Burton-Krahn et al., the detailed descriptions and Figures of which are hereby incorporated herein by reference in their entireties. The methods and apparatus of the present invention may be implemented using software-equivalent analysis of the present invention's stored ECG signals. Further, R-wave feature detection capabilities are also implemented as described and illustrated by the reference: Köhler B U, Hennig C, Orglmeister R, The principles of software QRS detection, IEEE Engineering in Medicine and Biology, January-February 2002, pages 42-57; the disclosure of which is hereby incorporated herein by reference in its entirety.

Following the detection of the various cardiac cycle features, the software analysis elements extract a vector of digital values, called a PT-wave 210, from each cardiac cycle of each ECG signal. A PT-wave is a vector of digital values of length M and includes the digital data in a cardiac cycle starting at the P-wave starting time 220 and ending at the T-wave ending time 270. The PT-wave, as a specific portion of the entire cardiac cycle, serves as the basis for the analysis performed by the present invention as it processes a patient's ECG signals to compute diagnostic markers related to the state of the patient's cardiac health. The PT-wave comprises five segments of the ECG data. These segments are the P-wave (from time marker 220 to time marker 230), the PR-segment (from time marker 230 to time marker 240), the R-wave (from time marker 240 to time marker 250), the ST segment (from time marker 250 to time marker 260), and the T-wave (from time marker 260 to time marker 270). The invention can also be applied to other portions of the cardiac cycle.

At the start of the PT-wave extraction process, as a first step and dependent on the condition of operation set by user-selectable testing parameters, a first set of three two-dimensional data matrices are created, each comprising storage locations for $M \times N_R$ digital data elements, where $N_R$ represents the number of reference (non-stimulated) cardiac cycles for the set of ECG signals. As a second step, a second set of three two-dimensional data matrices are created, each comprising storage locations for $M \times N_S$ digital data elements, where $N_S$ represents the number of stimulated cardiac cycles for the set of ECG signals. As a third step, a third set of three two-dimensional data matrices are created, each comprising storage locations for $M \times (N_R + N_S)$ digital data elements.

Figure 3:
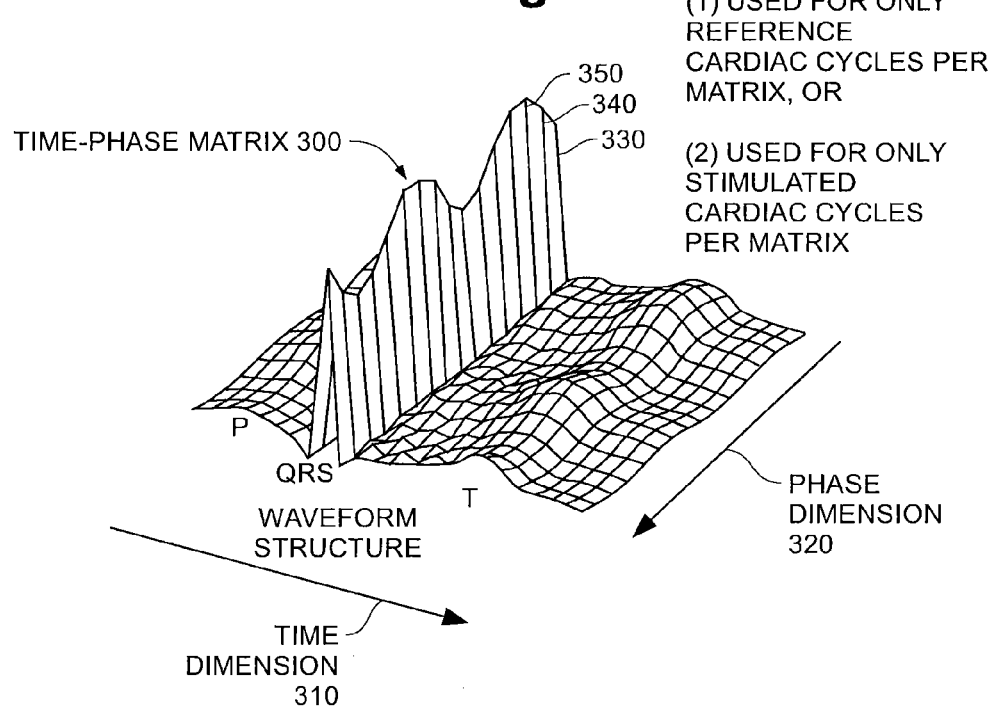
FIG. 3 illustrates an example time-phase matrix including individual PT-waves extracted from reference or stimulated cardiac cycles, in a time dimension, and a plurality of these PT-waves time-aligned in a phase dimension.
Figure 4:
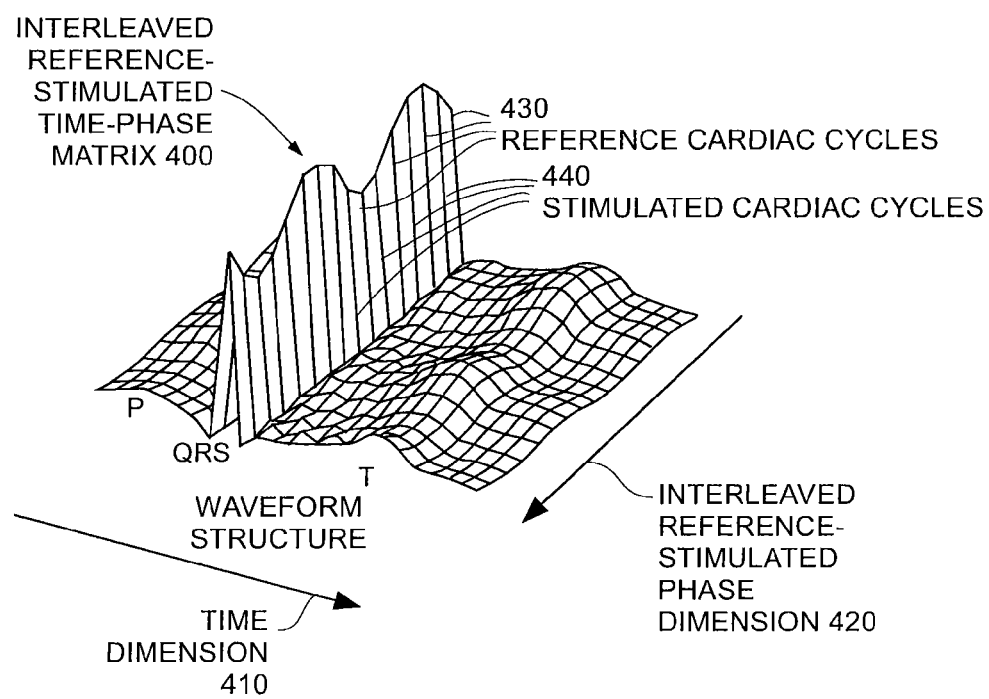
FIG. 4 illustrates an example time-phase matrix comprising individual PT-waves extracted from interleaved reference and stimulated cardiac cycles, in the time dimension, and a plurality of these PT-waves time-aligned in the phase dimension.

FIGS. 3 and 4 illustrate example time-phase matrices 300 and 400. The time-phase matrix illustrated in FIG. 3 comprises the time dimension M 310 and the phase dimension N 320 (where $N=N_R$ for the reference time-phase matrices and $N=N_S$ for the stimulated time-phase matrices). The three data matrices constructed in the first initialization step represent the reference cardiac cycles, are called the reference time-phase matrices 300, are herein labeled rTPX, rTPY, and rTPZ, and are associated with the reference cardiac cycles in the X, Y, and Z ECG signals. The three data matrices constructed in the second initialization step represent the stimulated cardiac cycles, are called the stimulated time-phase matrices 300, are herein labeled sTPX, sTPY, and sTPZ, and are associated with the stimulated cardiac cycles in the X, Y, and Z ECG signals. In the time-phase matrix, a row corresponds to an individual cardiac cycle and different column elements correspond to different cardiac cycles. The individual row-column values in a time-phase matrix correspond to the amplitude values of an ECG signal.

Following these first three initialization steps, an ECG signal is selected in order from the list of X, Y, and Z signals, and the software analysis element extracts each reference PT-wave from the selected ECG signal, labels its vector of digital data as rPT-wave(1:M,j), where j=1 to $N_R$ for the number of referenced cardiac cycles in the ECG signal, and stores the rPT-wave(1:M,j) into the signal's time-phase matrix. As an illustration, each of the extracted rPT-wave(1:M,j) data vectors for the X signal are stored into the time-phase matrix rTPX(1:M,j)=rPT-wave(1:M,j). FIG. 3 illustrates a first PT-wave 330 stored into the time-phase matrix, a second PT-wave 340 stored into the time-phase matrix, and a third PT-wave 350 stored into the time-phase matrix. At the end of the reference PT-wave extraction process for the X signal, the rTPX matrix comprises $N_R$ PT-waves, one for each reference cardiac cycle in X, with each PT-wave having M data points. A similar process is then performed using the Y and the Z signals, which then completes the construction of the rTPY and rTPZ matrices.

Following the construction of the rTPX, rTPY, and rTPZ matrices, the sTPX, sTPY, and sTPZ matrices are constructed by repeating the extraction process for the PT-wave vectors for the stimulated cardiac cycles in the ECG signals. An ECG signal is selected in order from the list of X, Y, and Z signals, and the software analysis element extracts each stimulated PT-wave from the selected ECG signal, labels its vector of digital data as sPT-wave (1:M,j), where j=1 to $N_S$ for the number of stimulated cardiac cycles in the ECG signal, and stores the sPT-wave(1:M,j) into the signal's time-phase matrix. As an illustration, each of the extracted sPT-wave(1:Mj) data vectors for the X signal are stored into the time-phase matrix sTPX(1:M,j)=sPT-wave(1:M,j). At the end of the stimulated PT-wave extraction process for the X signal, the sTPX matrix comprises $N_S$ PT-waves, one for each stimulated cardiac cycle in X, with each PT-wave having M data points. A similar process is next performed using the Y and the Z signals, which then completes the construction of the sTPY and sTPZ matrices.

Following the construction of the sTPX, sTPY, and sTPZ matrices, the iTPX, iTPY, and iTPZ matrices are constructed by repeating the extraction process for the PT-wave vectors for all cardiac cycles in the ECG signals. The iTPX, iTPY, and iTPZ matrices represent the complete set of cardiac cycles in an ECG signal in their naturally occurring order, and this complete set of extracted ECG cardiac cycles is called the interleaved reference-stimulated cardiac cycle set.

FIG. 4 illustrates a typical interleaved reference-stimulated time-phase matrix 400, with PT-wave defined time dimension 410 and phase dimension 420. FIG. 4 illustrates an interleaved pattern of subthreshold pulsing in which every other cardiac cycle is stimulated with a subthreshold pulse, and the PT-waves are stored into the time-phase matrix such that the reference PT-waves 430 are stored interleaved with the stimulated PT-waves 440 that are stored. An ECG signal is selected in order from the list of X, Y, and Z signals, and the software analysis element extracts each PT-wave from the selected ECG signal, labels its vector of digital data as iPT-wave(1:M,j), where j=1 to $N_T (=N_R+N_S)$ for the total number of cardiac cycles in the ECG signal, and stores the iPT-wave(1:Mj) into the signal's time-phase matrix. As an illustration, each of the extracted iPT-wave(1:Mj) data vectors for the X signal are stored into the time-phase matrix iTPX(1:M,j)=iPT-wave(1:

M,j). At the end of the PT-wave extraction process for the X signal, the iTPX matrix comprises $N_T$ PT-waves, one for each cardiac cycle in X, with each PT-wave having M data points. A similar process is next performed using the Y and the Z signals, which then completes the construction of the iTPY and iTPZ matrices.

At the end of the construction of the nine time-phase matrices, the present invention has created the matrices such that the PT-wave of each cardiac cycle in each time-phase matrix is the same length, M, and the PT-wave of each cardiac cycle in one time-phase matrix is time-aligned with every other PT-wave in the same time-phase matrix and it is also time-aligned with every other PT-wave in the other eight time-phase matrices. The data across a row are the amplitude values for an ECG signal in a single PT-wave and the data across a column are the amplitude values for an ECG signal at a fixed point in time in each PT-wave, called the phase for the PT-wave.

Following the formation of the three reference time-phase matrices, three stimulated time-phase matrices, and three interleaved time-phase matrices for the ECG orthogonal signals, a fourth set of three time-phase matrices are computed, called the vector magnitude time-phase matrices.

Figure 5:
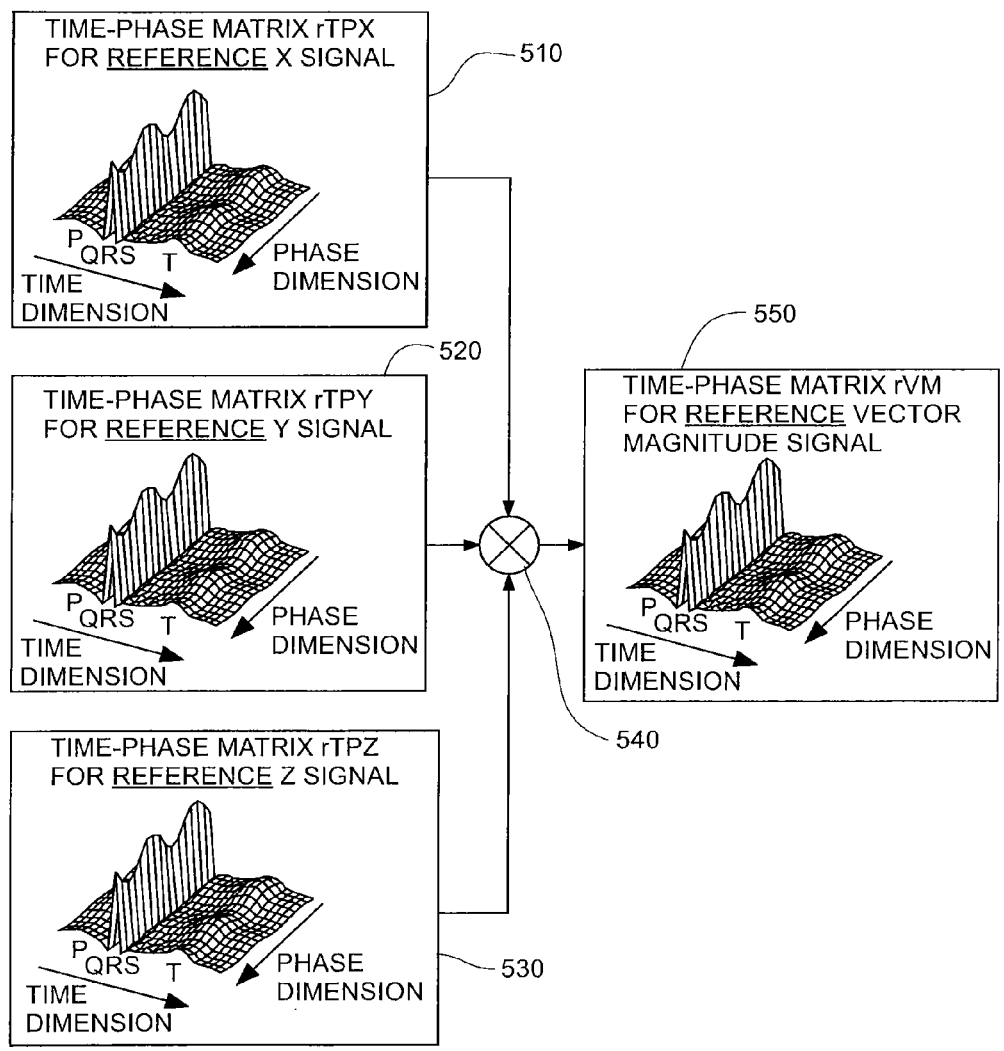
FIG. 5 illustrates X, Y, and Z reference time-phase matrices that are combined to form a reference vector magnitude time-phase matrix.

The construction of the reference vector magnitude time-phase matrix, rVM 550, is illustrated in FIG. 5. The time-phase matrices rTPX 510, rTPY 520, and rTPZ 530 are used to compute rVM 550 using the vector magnitude computation 540 (Euclidean distance metric) applied to the reference time-phase matrices. The reference vector magnitude time-phase matrix represents the magnitude of the three-dimensional dipole signal for the heart's electrical activity during the time course for each reference cardiac cycle. The reference vector magnitude time-phase matrix is computed such that the value for each row-column element in its matrix is the square root of the sum of the squares of the values in the corresponding row-column elements for the rTPX, rTPY, and rTPZ matrices. Thus, by construction and computation, in the rVM, a row corresponds to an individual reference vector magnitude PT-wave for the associated reference X, Y, and Z PT-waves and different column elements correspond to different reference vector magnitude PT-wave values computed from different reference X, Y, and Z PT-waves.

Figure 8:
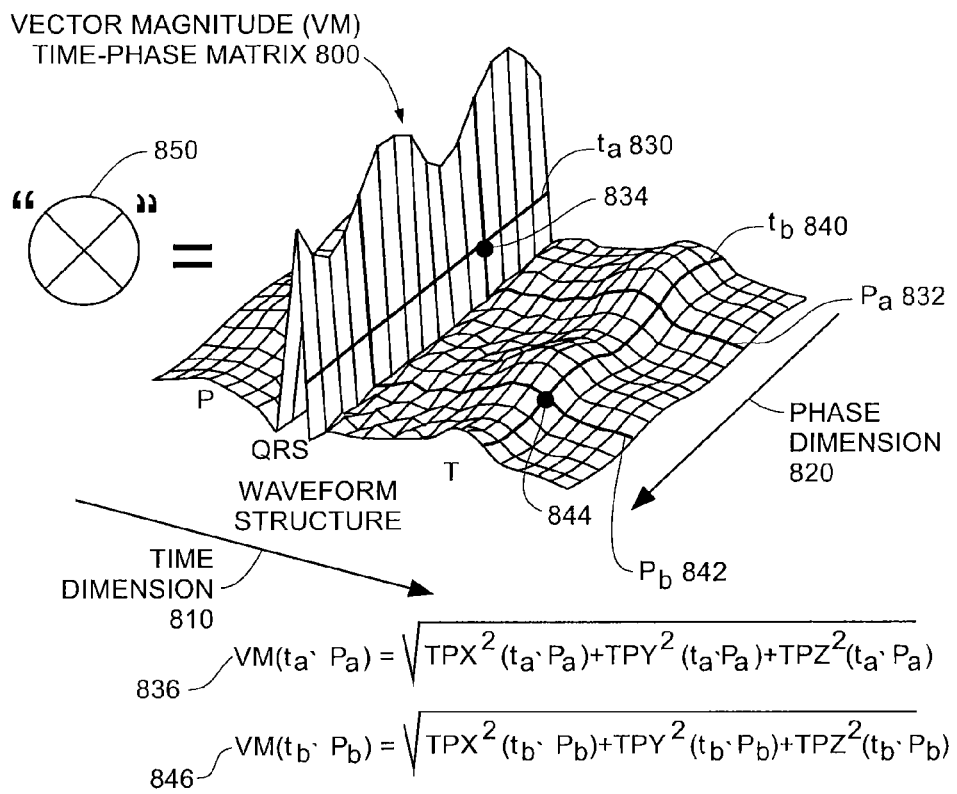
FIG. 8 illustrates a method for combining X, Y, and Z time-phase matrices into a vector magnitude time-phase matrix.

FIG. 8 illustrates the formula and the construction process that computes the conventional vector magnitude cardiac cycle using the cardiac cycles X, Y, and Z cardiac cycle components as represented by the X, Y, and Z ECG signals in the various sets of TPX, TPY, and TPZ matrices. The general computations to construct a vector magnitude time-phase matrix are illustrated in FIG. 8 and the application of the general vector magnitude computations (Euclidean distance metric) are indicated by the short-hand symbol 850. As an example, the value $t_a$ 830 represents a position along the time dimension 810, the value $p_a$ 832 represents a position along the phase dimension 820, and together the $(t_a, p_a)$ pair represents a position in the vector magnitude time-phase matrix. The $(t_a, p_a)$ pair-value 834 in the vector magnitude time-phase matrix for the $(t_a, p_a)$ pair-position is illustrated by the vector magnitude formula associated to this pair-position 836, and therefore the $(t_a, p_a)$ pair-position contains an estimated ECG R-wave vector magnitude value in the three-dimensional dipole signal. In the same manner and as another example, the value $t_b$ 840 represents a position along the time dimension 810, the value $p_b$ 842 represents a position along the phase dimension 820, and together the $(t_b, p_b)$ pair represents a position in the vector magnitude time-phase matrix. The $(t_b, p_b)$ pair-value 844 in the vector magnitude time-phase matrix for the $(t_b, p_b)$ pair-position is illustrated by the vector magnitude formula associated to this pair-position 846, and therefore the $(t_b, p_b)$ pair-position contains an estimated ECG T-wave vector magnitude value in the three-dimensional dipole signal.

Figure 6:
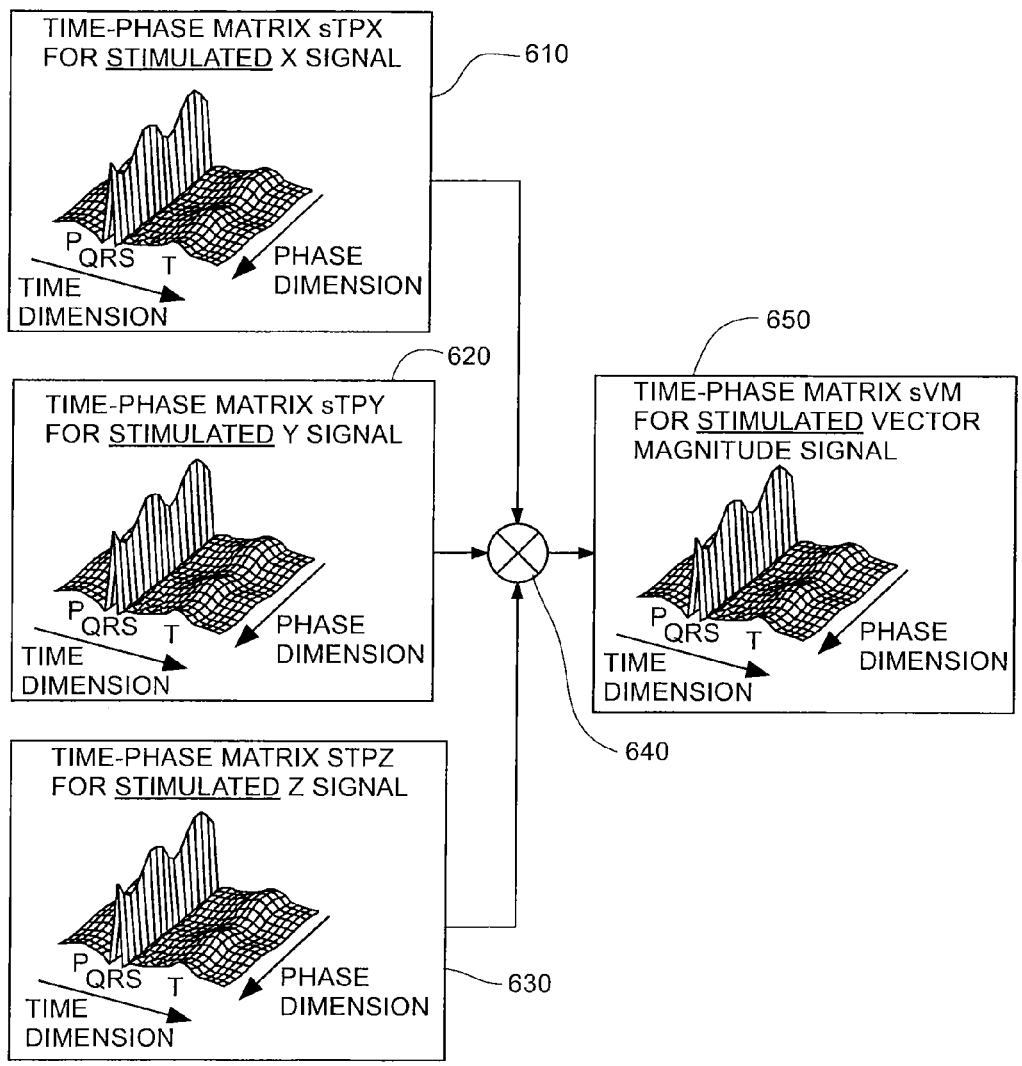
FIG. 6 illustrates X, Y, and Z stimulated time-phase matrices that are combined to form a stimulated vector magnitude time-phase matrix.

The construction of the stimulated vector magnitude time-phase matrix, sVM 650, is illustrated in FIG. 6. The time-phase matrices sTPX 610, sTPY 620, and sTPZ 630 are used to compute sVM 650 using the vector magnitude computation 640 (Euclidean distance metric) applied to the stimulated time-phase matrices. The stimulated vector magnitude time-phase matrix represents the magnitude of the three-dimensional dipole signal for the heart's electrical activity during the time course for each stimulated cardiac cycle. The stimulated vector magnitude time-phase matrix is computed such that the value for each row-column element in its matrix is the square root of the sum of the squares of the values in the corresponding row-column elements for the sTPX, sTPY, and sTPZ matrices. Thus, by construction and computation, in the sVM, a row corresponds to an individual stimulated vector magnitude PT-wave for the associated stimulated X, Y, and Z PT-waves and different column elements correspond to different stimulated vector magnitude PT-wave values computed from different stimulated X, Y, and Z PT-waves.

Figure 7:
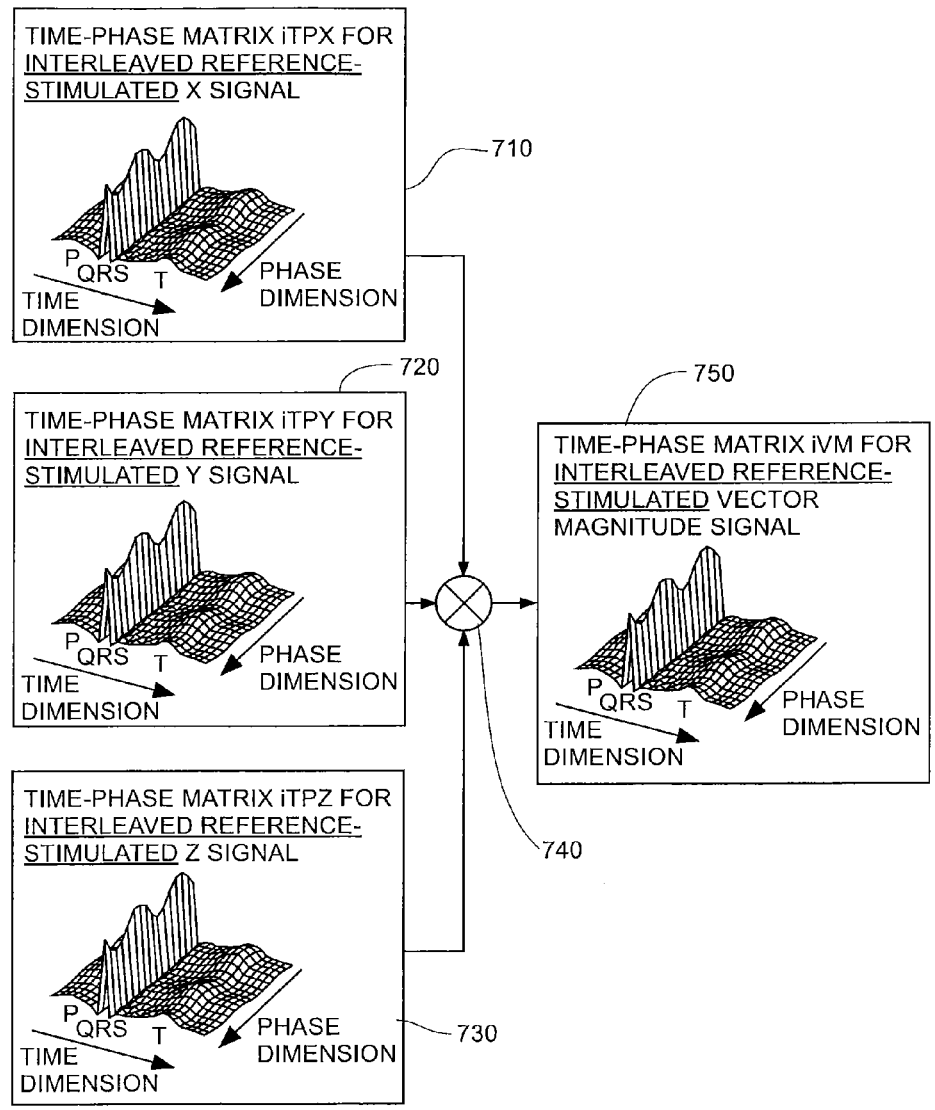
FIG. 7 illustrates X, Y, and Z interleaved reference-stimulated time-phase matrices that are combined to form an interleaved reference-stimulated vector magnitude time-phase matrix.

The construction of the interleaved reference-stimulated vector magnitude time-phase matrix, iVM 750, is illustrated in FIG. 7. The time-phase matrices iTPX 710, iTPY 720, and iTPZ 730 are used to compute iVM 750 using the vector magnitude computation 740 (Euclidean distance metric) applied to the interleaved reference-stimulated time-phase matrices. The interleaved reference-stimulated vector magnitude time-phase matrix represents the magnitude of the three-dimensional dipole signal for the heart's electrical activity during the time course for each interleaved reference-stimulated cardiac cycle. The interleaved reference-stimulated vector magnitude time-phase matrix is computed such that the value for each row-column element in its matrix is the square root of the sum of the squares of the values in the corresponding row-column elements for the iTPX, iTPY, and iTPZ matrices. Thus, by construction and computation, in the iVM, a row corresponds to an individual interleaved reference-stimulated vector magnitude PT-wave for the associated interleaved reference-stimulated X, Y, and Z PT-waves and different column elements correspond to different interleaved reference-stimulated vector magnitude PT-wave values computed from different interleaved reference-stimulated X, Y, and Z PT-waves.

Now having placed the reference, stimulated, and interleaved reference-stimulated cardiac cycles from the three orthogonal ECG signals into the rTPX, rTPY, rTPZ, sTPX, sTPY, sTPZ, iTPX, iTPY, and iTPZ matrices, and now having computed the corresponding rVM, sVM, and iVM matrices, then vector and matrix operations and analysis are used to determine one-dimensional cardiac cycle time and cardiac cycle phase related diagnostic markers and two-dimensional cardiac cycle time-phase related diagnostic markers. Additional important technical steps comprising the present invention analyze the differences and ratios determined between the reference time-phase matrices and the associated stimulated time-phase matrices to compute a plurality of diagnostic markers. The diagnostic markers relate to cardiac-related disease status, such as a patient's susceptibility to ventricular arrhythmias, in so much as these markers represent a measure of diagnostic information contained within a patient's PT-wave data.

Figure 18:
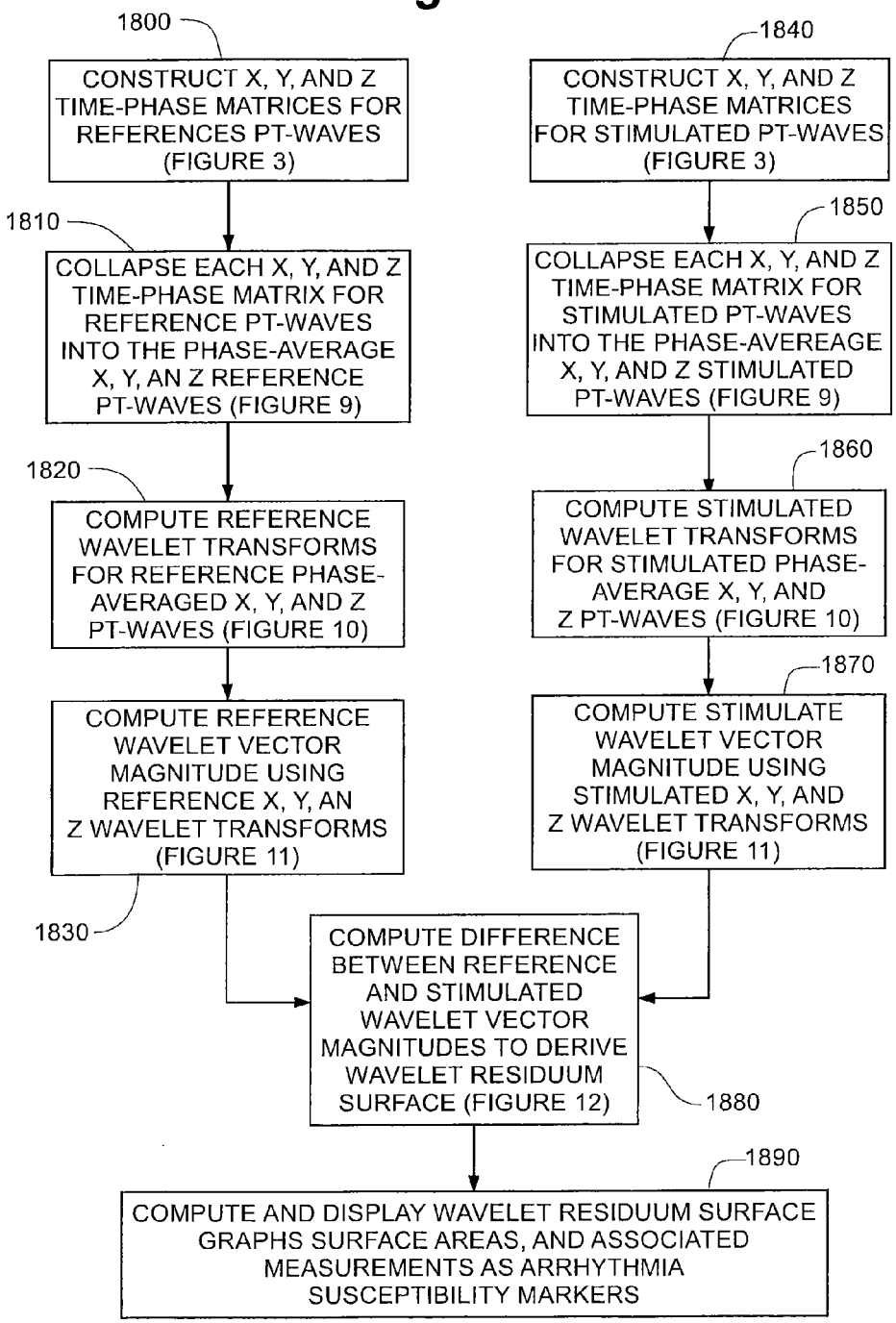
FIG. 18 illustrates a flowchart for a method of analyzing a patient's Wedensky modulated ECG data using frequency-domain wavelet vector magnitudes to determine continuous wavelet-based modulation graphs and associated arrhythmia indices in accordance with the invention.

FIG. 18 illustrate the flowchart for the general method and apparatus to use a plurality of reference and stimulated PT-waves to compute diagnostic information and specific markers based on continuous wavelet transform technology. FIG.

18, together with FIGS. 3, 9, 10, 11, and 12 provide a detailed description of the software analysis elements and steps to prepare the ECG signals for computing reference and stimulated continuous wavelet transforms and the continuous wavelet surface residuum. A review of the continuous and discrete wavelet transforms applied to ECG signals is presented in the publication by Addision (Addision PS, Wavelet transforms and the ECG: a review, Physiol Meas 2005; 26: R155-R199), the disclosure of which is hereby incorporated herein by reference in its entirety. A further review of the continuous wavelet transform-based approach specific to the assessment of post-myocardial infarction patients with a susceptibility for ventricular tachycardias is presented in the publication by Popescu et al (Popescu M, Laskaris N, Chiladakis I, Stathopoulos C, Cristea P, Manolis A, Bezerianos A, Beat-to-beat wavelet variance of the QRS complex as a marker of arrhythmia substrate in ventricular tachycardia patients, Physiol Meas 1998; 19: 77-92), the disclosure of which is hereby incorporated herein by reference in its entirety. Specific algorithm details related to Wedensky modulation and clinical analysis results are presented in the publication by Hnatkova et al (Hnatkova K, Ryan S J, Bathen J, Hoium H H, Malik M, Non-invasive Wedensky modulation within the QRS complex, Med Biol Eng Comput 2002; 40: 234-240), the disclosure of which is hereby incorporated herein by reference in its entirety. The publication by Hnatkova describes details to the present invention as they relate to the clinical confirmation of the present invention regarding to the application of Wedensky modulation to patients for the determination of significantly discriminating diagnostic R-wave and T-wave markers for a patient's arrhythmia susceptibility. Taken together, the incorporated U.S. Pat. No. 6,512,947 reference and the incorporated Hnatkova et al reference describe the structural, operational, and clinical components of the present invention.

As a first step following the process of Wedensky modulation and the acquisition of the ECG signals, the present invention's software analysis element 1800 constructs the rTPX, rTPY, and rTPZ time-phase matrices for the reference PT-waves (which are the present invention's embodiment of the reference cardiac cycles in a patient's ECG signal and are illustrated in FIGS. 2 and 3).

Figure 9:
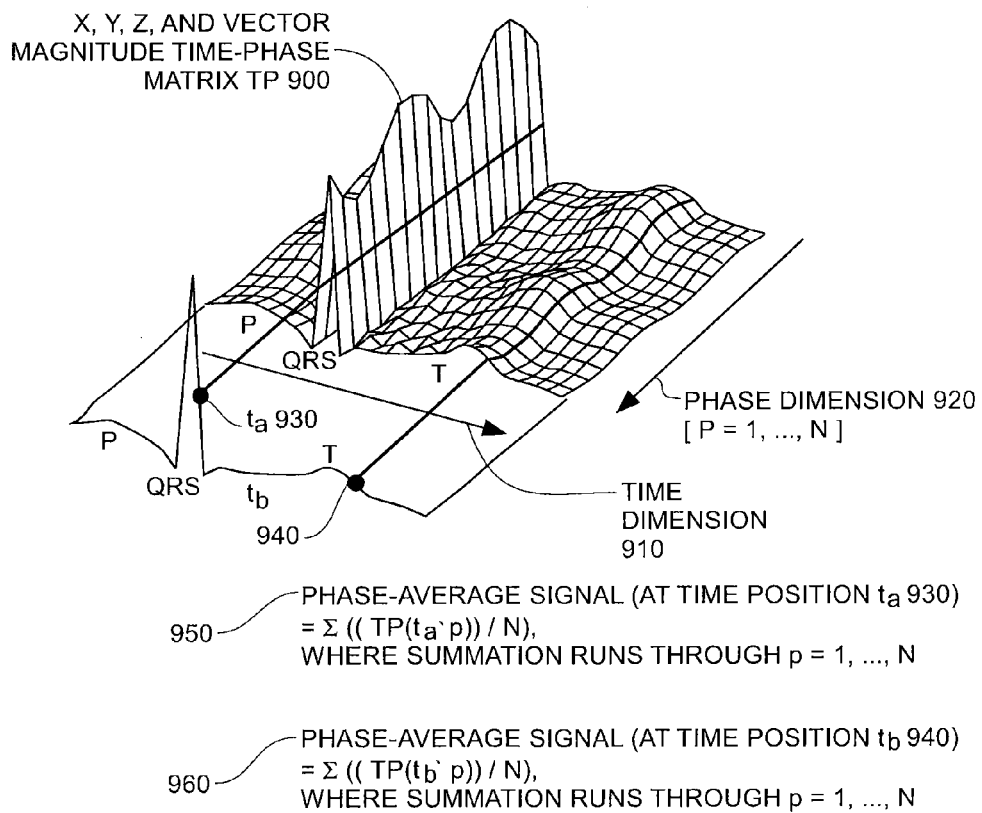
FIG. 9 illustrates a method for collapsing a X, Y, Z, or vector magnitude time-phase matrix into a phase-averaged PT-wave to represent the PT-waves comprising the time-phase matrix.

As a second step, the software analysis element 1810 collapses the reference rTPX, rTPY, and rTPZ time-phase matrices into the reference phase-averaged X, Y, and Z PT-waves, as illustrated in FIG. 9 for a time-phase matrix 900. For each point in time along the time axis 910 (a time-row index for a time-phase matrix), the collapsing operation computes the average of PT-wave values in the time-phase matrix along the phase axis 920 (using the PT-wave values in the phase-column indexed by the time-row index). As a first example, the collapsing operation computes the average PT-wave value 950 for a point in time in the R-wave, herein labeled $t_a$ 930. As a second example, the collapsing operation computes the average PT-wave value 960 for a point in time in the T-wave, herein labeled $t_b$ 940. In this manner, the collapsing operation computes the phase-averaged PT-wave for a time-phase matrix.

Figure 10:
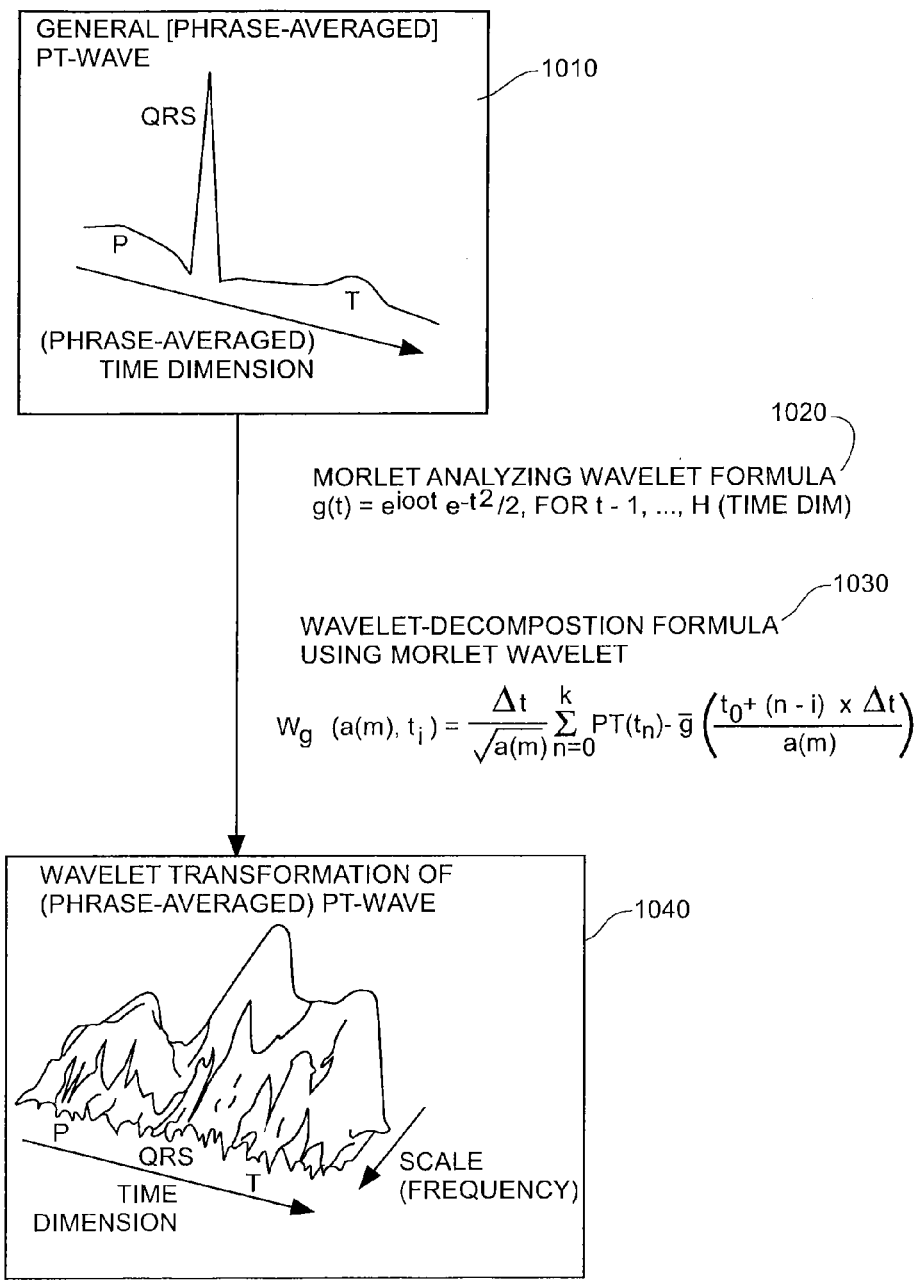
FIG. 10 illustrates a method for computing the continuous wavelet transform of a phase-averaged X, Y, Z, and vector magnitude PT-wave.

As a third step, the software analysis element 1820 computes the reference continuous wavelet transforms rWX, rWY, and rWZ using the reference phase-averaged PT-waves for the X, Y, and Z ECG signals, as illustrated in FIG. 10 for the phase-averaged PT-wave 1010. The software analysis element 1820 applies the Morlet wavelet transform, using the Morlet analyzing wavelet formula 1020 and the wavelet-decomposition formula 1030 to a phase-averaged PT-wave to construct the reference continuous wavelet transform 1040, also called the reference continuous wavelet-decomposed representation 1040.

Figure 11:
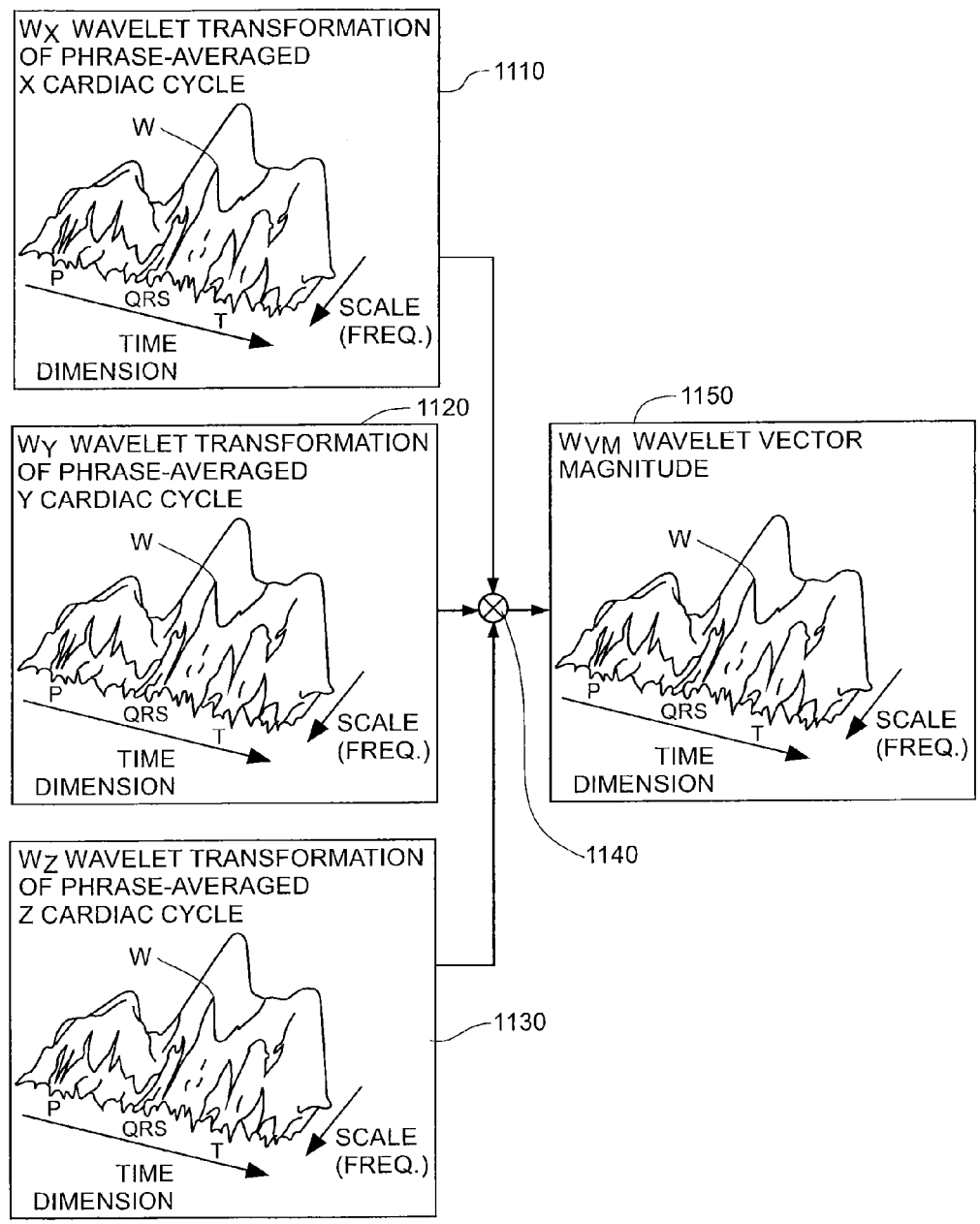
FIG. 11 illustrates a method for combining the continuous wavelet transforms for the phase-averaged X, Y, and Z PT-waves into a wavelet vector magnitude.

As a fourth step, the software analysis element 1830 then computes the reference wavelet vector magnitude rWVM using the reference wavelet transforms rWX, rWY, and rWZ, as illustrated in FIG. 11 and shown for a general triple of continuous wavelet transforms and the associated wavelet magnitude. The continuous wavelet transform matrices rWX 1110, rWY 1120, and rWZ 1130 are used to compute rWVM 1150 using the vector magnitude computation 1140 and Euclidean distance metric formula 1160 applied to each of the rWX, rWY, and rWZ wavelet transform matrix elements. An illustrative wavelet transform matrix position in FIG. II and formula 1160 is depicted as "w" in each Figure part 1110, 1120, 1130, and 1150.

FIG. 18, together with FIGS. 3, 9, 10, and 11, further illustrate the software analysis elements 1840, 1850, 1860, and 1870 and their four construction and computation steps to first construct the stimulated sTPX, sTPY, and sTPZ time-phase matrices for the stimulated PT-waves (which are the present invention's embodiment of the stimulated cardiac cycles in a patient's ECG signal and are illustrated in FIGS. 2 and 3), to second collapse the stimulated sTPX, sTPY, and sTPZ time-phase matrices into the stimulated phase-averaged PT-waves for the X, Y, and Z ECG signals (FIG. 9), to third compute the stimulated continuous wavelet transforms sWX, sWY, and sWZ using the stimulated phase-averaged PT-waves (FIG. 10), and to fourth compute the stimulated wavelet vector magnitude sWVM using the stimulated continuous wavelet transforms sWX, sWY, and sWZ (FIG. 11).

Further, the method and computational steps illustrated in FIG. 10 can be applied by the present invention to any generally defined PT-wave construction 1020, such as the general PT-wave representative of a reference X, Y, Z, or VM PT-wave, a phase-averaged reference X, Y, Z, and VM PT-wave, a stimulated X, Y, Z, and VM PT-wave, a phase-averaged X, Y, Z, and VM PT-wave, and such that the generally defined PT-wave construction 1020 is continuous wavelet decomposed into its transform representation matrix 1040 using the general continuous wavelet transform formulas 1020 and 1030. The contribution to the signal energy at specific scales and locations is given by the two-dimensional wavelet energy density function as the square of the wavelet transform values 1040 and is called the scalogram. The scale-dependent wavelet energy is converted to frequency-dependent wavelet energy by converting from the base wavelet scale to a predetermined characteristic frequency, herein labeled $f_c$, of the wavelet. Examples of a predetermined characteristic frequency $f_c$ are the peak frequency, passband center, and central frequency. Since spectral components are inversely proportional to the scale, then the frequency associated with a wavelet of scale "s" is given by $f=(f_c/s)$. For the practical implementation of the continuous wavelet transform 1040, the transform is computed over a finely discretized time-frequency grid with the location parameter designating time and the scaling parameter designating frequency (where the scale parameter is converted to a frequency parameter as described above). The details regarding the location and scale parameters of the wavelet transform and its construction for the present invention are described within the incorporated Hnatkova reference.

Figure 12:
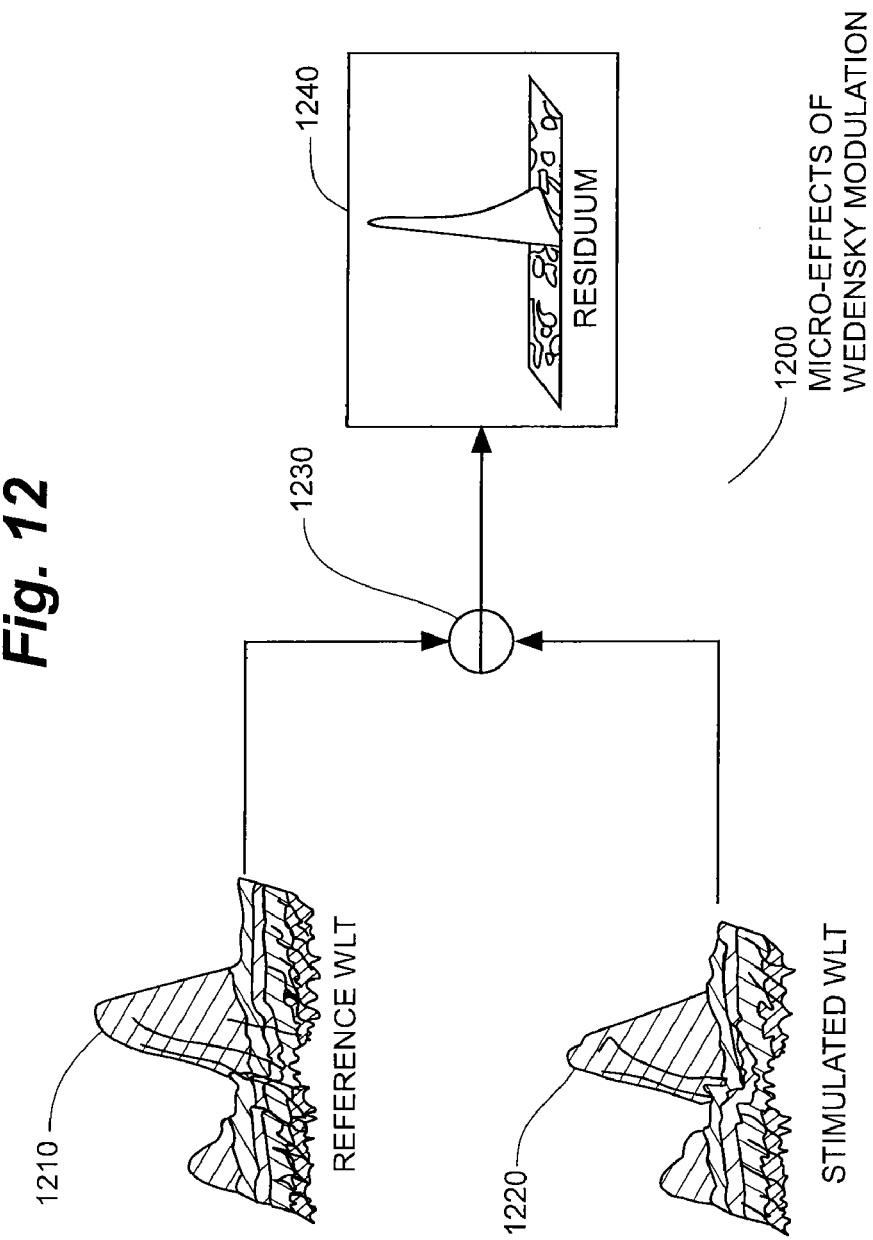
FIG. 12 illustrates a method for computing a continuous wavelet surface residuum by subtracting the reference wavelet vector magnitude from the stimulated wavelet vector magnitude.

FIG. 18 further illustrates the software analysis element 1880 that is tasked to perform the fifth and combining flow-chart step to compute the continuous wavelet surface residuum. The flowchart for the operation of software analysis element 1880 is illustrated in FIG. 12. Software analysis element 1880 subtracts 1230 the reference wavelet vector magnitude matrix representation rWVM 1210 point by point from the stimulated wavelet vector magnitude matrix representation sWVM 1220 to construct the continuous wavelet surface residuum 1240. As a sixth step, the software analysis element 1890 computes and display the residuum, surface area measurements, and statistical comparisons to serve as a set of diagnostic markers. A plurality of these markers are described in the aforementioned U.S. Pat. Nos. 6,445,947, and 6,512,947 issued to Hoium et al, and the Hnatkova et al reference, the disclosures of which were previously incorporated herein by reference in their entireties. New indices are described in subsequent paragraphs. As can be appreciated from the description of the present invention, the continuous wavelet surface residuum 1240 and its associated diagnostic markers are computed to permit a physician an ability to distinguish and interpret small but significant differential effects 1200 of Wedensky modulation.

Relating to the present invention and its embodiments, susceptibility to ventricular arrhythmias is determined using one or more diagnostic indices derived from a plurality of analyses between the reference PT-waves and the stimulated PT-waves residing in the time-phase matrices. As is well-known in the art, R-wave and T-wave alternans are phenomena appearing in a patient's ECG as consistent fluctuations in the depolarization and repolarization morphologies on a cardiac cycle by cardiac cycle basis. A variety of analysis methods have been developed to detect and estimate the levels of microvolt alternans in the ECG. A recent publication presented a unified framework for the methodological principles that represent a foundation for evaluating these methods. The recent publication reference is Martínez J P, Olmos S, Methodological principles of T wave alternans analysis: A unified framework, IEEE Trans Biomedical Engineering 2005; 52(4): 599-613, the disclosure of which is incorporated herein by reference in its entirety.

The details to the interpretation and classification of microvolt R-wave and T-wave alternans tests are further described in recent clinical review publications, which provide a contemporary evidence-based framework for the use of MTWA to risk stratify for sudden cardiac death, and which establishes uniform standards for the its clinical interpretation. These review references are (a) Bloomfield D M, Hohnloser S H, Cohen R J, Interpretation and classification of microvolt T-wave alternans tests, J Cardiovasc Electrophysiol 2002; 13: 502-512, and (b) Narayan S M, T-wave alternans and the susceptibility to ventricular arrhythmias, J Am Coll Cardiol 2006; 47: 269-281, the disclosures of which are hereby incorporated herein by reference in their entireties. These recent publications further delineate the limitations to the MTWA test and supports the present invention's method to subthreshold pulse the myocardial tissue in an interleaved manner that magnifies the alternans archetype and thereby increases the ability to measure alternans without strenuous physical or pharmacological stress.

The present invention, as a method and an apparatus for constructing and computing alternans energy indices, further comprises the methods and apparatus disclosed in U.S. Pat. No. 4,802,491 issued to Cohen et al, U.S. Pat. No. 5,713,367 issued to Arnold et al, and in U.S. Pat. No. 5,935,082 issued to Albrecht et al, the disclosures of which are hereby incorporated herein by reference in their entireties. Signal processing of the time-phase matrices provides superior sensitivity and specificity, reducing the effects of intercycle interval variability, reducing the effects of respiration, improving the determination of the statistical significance of the alternans measurement, and combining measurement of the alternans with other cardiovascular diagnostic tests to facilitate and improve the combined diagnostic capability. A limited number of signal processing operations executed on the time-phase matrices are described in these issued US Patent references that have been incorporated herein in their entireties. New structural and operational details of the present invention's paramount elements in relationship to the computation of various microvolt R-wave alternans indices and microvolt T-wave alternans indices using the reference and stimulated time-phase matrices are now described.

A first diagnostic index is based on the derivation of an alternans ECG morphology index. Alternans energy values are evaluated within a predetermined time dimension segment of the PT-wave and along the phase dimension, are then summed to generate an alternans energy index, and this alternans energy index is normalized with respect to the energy of the averaged PT waveform. The alternans pattern of cycle-to-cycle variability is evaluated in the presence of electrical stress applied to a patient in the form of the present invention's methods for subthreshold pulsing during batched or interleaved modes of operation. The electrical stress increases the amplitude of the alternans and these alternans are further differentiated when comparing a patient's reference ECG signal data to the patient's stimulated ECG signal data.

A plurality of indices that estimate the energy of the alternans component of the PT-wave are now computed for each time-phase matrix. These indices are an index measuring the energy of the alternans component of the R-wave and an index measuring the energy of the alternans component of the T-wave. In this manner, there are at least eight reference indices, at least eight stimulated indices, and at least eight interleaved reference-stimulated indices.

Additional alternans indices can be computed when selected by an operator of the present invention using the invention's operator interface. As a first example to illustrate the computation of additional sets of alternans indices, an operator may select a portion of the PT-wave that defines the P-wave, designating a starting PT-wave time position 220 and designating an ending PT-wave time position 230 for the P-wave, and directing the present invention's software analysis elements to process and analyze a patient's recently Wedensky modulated and acquired ECG signals to construct and compute alternans indices for the alternans components that exist in the patient's P-wave. In this manner, an operator, such as a physician using the present invention to diagnose a patient for susceptibility or predisposition for life-threatening ventricular arrhythmia events, can form a diagnosis that is based on a selected portion of the patient's ECG signal and the present invention's subsequent analysis thereof.

As a second example to illustrate the computation of additional sets of alternans indices, an operator may select a portion of the PT-wave that defines the ST-segment, designating a starting PT-wave time position 250 and designating an ending PT-wave time position 260 for the ST-segment, and directing the present invention's software analysis elements to process and analyze a patient's recently Wedensky modulated and acquired ECG signals to construct and compute alternans indices for the alternans components that exist in the patient's ST-segment. In this manner, an operator, such as a physician using the present invention to diagnose a patient for susceptibility or predisposition for life-threatening ventricular arrhythmia events, can form a diagnosis that is based on a selected portion of the patient's ECG signal and the present invention's subsequent analysis thereof.

Figure 19:
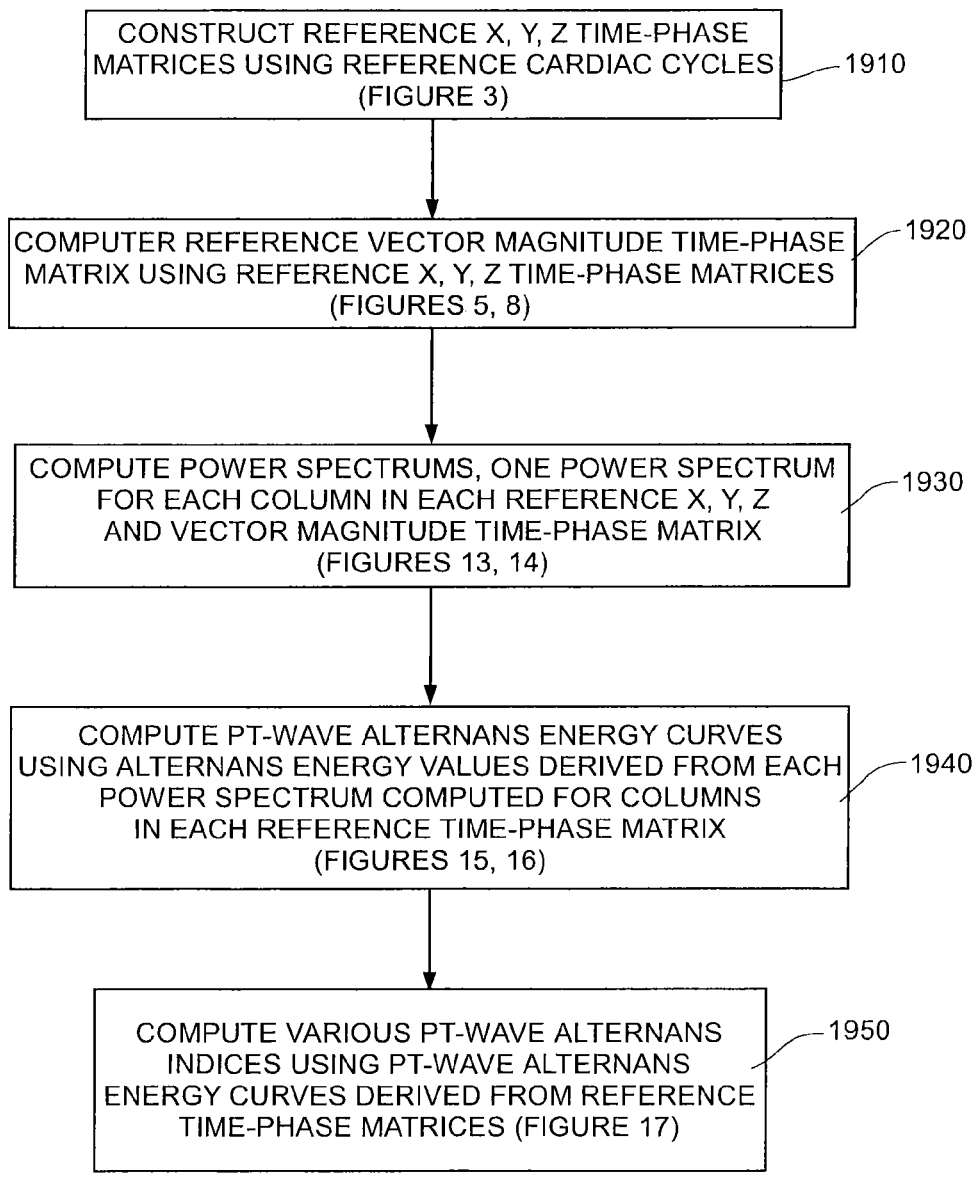
FIG. 19 illustrates a flowchart for a method of analyzing a patient's ECG data without Wedensky modulation (reference ECG data only) to compute R-wave and T-wave alternans indices in accordance with the invention.

FIG. 19 illustrate the flowchart for the general method and apparatus to use a plurality of reference PT-waves to compute diagnostic information and specific markers based on Fourier transform technology. FIG. 19, together with FIGS. 3, 5, 8, 13, 14, 15, 16, and 17 provide a detailed description of the software analysis elements and steps to prepare the ECG signals for computing reference Fourier transforms, reference power spectrums, and the spectral alternans measurements used to compute the reference alternans energy indices.

As a first step following the process of Wedensky modulation and the acquisition of the ECG signals, the present invention's software analysis element 1910 constructs the rTPX, rTPY, and rTPZ time-phase matrices for the reference PT-waves (which are the present invention's embodiment of the reference cardiac cycles in a patient's ECG signal and are illustrated in FIGS. 2 and 3).

As a second step, the software analysis element 1920 constructs the reference vector magnitude rVM time-phase matrix, as illustrated in FIGS. 5 and 8 for a time-phase matrix 900 and as previously described.

Figure 13:
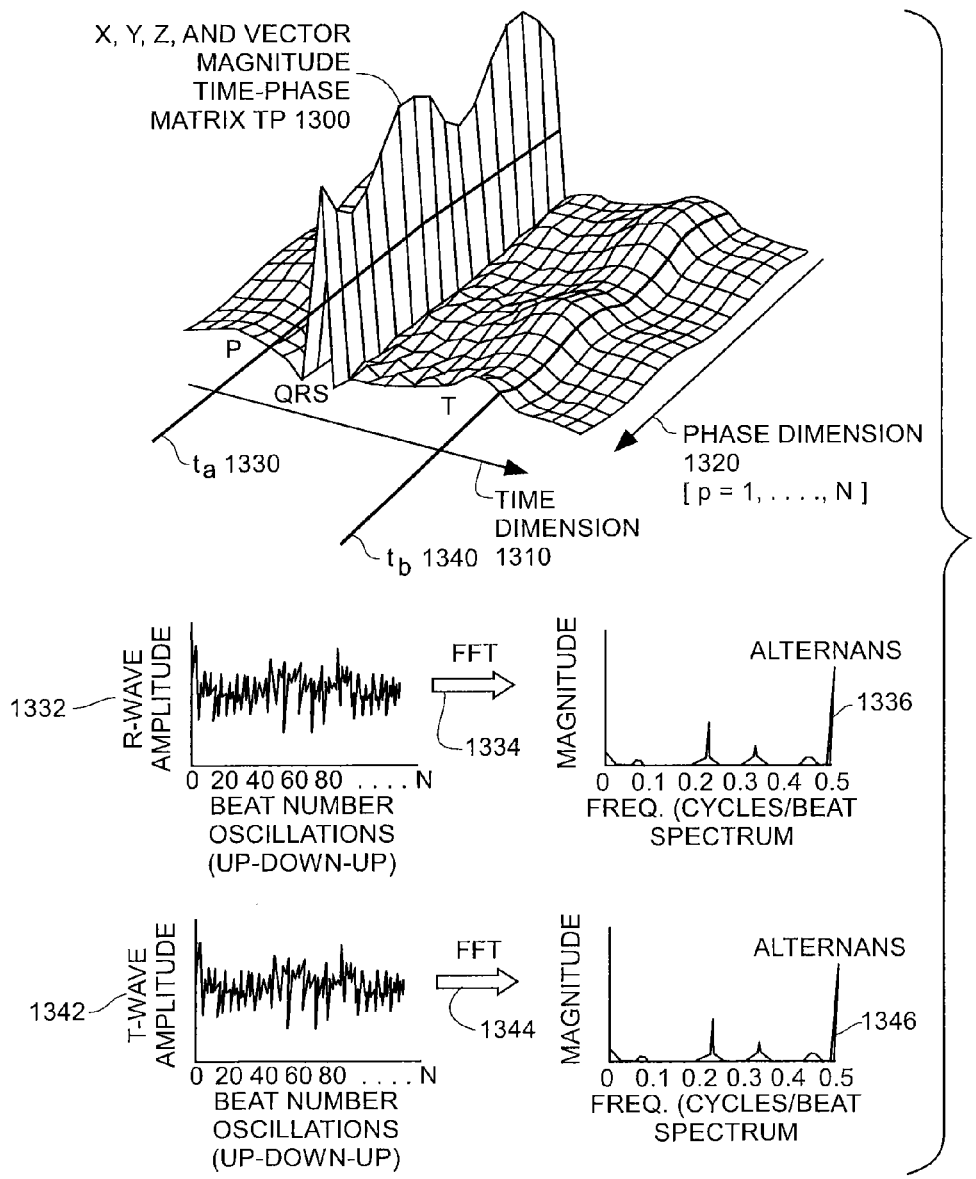
FIG. 13 illustrates a method of using a discrete Fourier transform to compute alternans measurements from the R-wave and from the T-wave in the direction of the phase dimension of a plurality of PT-waves in a time-phase matrix.
Figure 14:
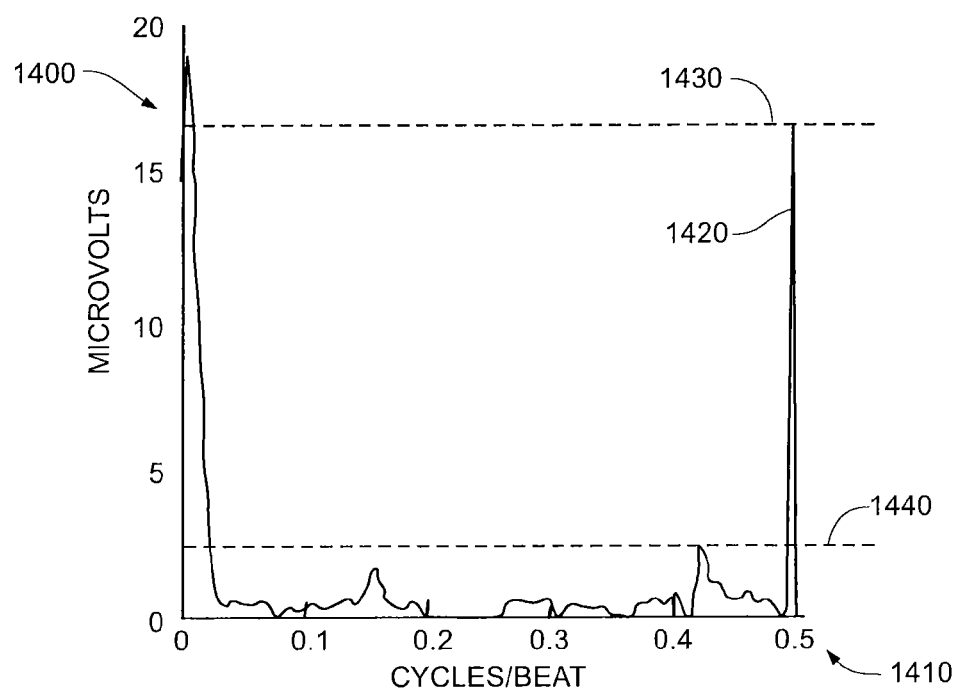
FIG. 14 illustrates a graphical presentation of a power spectrum for a fixed point in time and in the direction of the phase dimension of a time-phase matrix of PT-waves and the level of spectrally measured alternans energy measured at 0.5 cycles per beat.

As a third step, the software spectral analysis element 1930 computes the power spectrums for the reference X, Y, and Z time-phase matrices and their associated reference vector magnitude rVM, as illustrated in FIGS. 13 and 14 for a time-phase matrix 1300. As a first example, the software spectral analysis element 1930 computes the power spectrum 1336 for a point in time $t_a$ 1330 on the time axis 1310 and in the R-wave. The analysis element 1930 first extracts a portion of R-wave data 1332 from a time-phase matrix along the phase axis 1320 indexed by the time point $t_a$ 1330 (a column of R-wave data in a time-phase matrix indexed by the time point $t_a$ 1330), next applies a fast-Fourier transform (FFT) 1334 to the extracted R-wave data, and then next computes a power spectrum 1336 using the resulting frequency-domain data derived from the Fourier transform operation. As a second example, the software spectral analysis element 1930 computes the power spectrum 1346 for a point in time $t_b$ 1340 on the time axis 1310 in the T-wave. The analysis element 1930 first extracts a portion of T-wave data 1342 from a time-phase matrix along the phase axis 1320 indexed by the time point $t_b$ 1340 (a column of T-wave data in a time-phase matrix indexed by the time point $t_b$ 1340), next applies a fast-Fourier transform (FFT) 1344 to the extracted T-wave data, and then next computes a power spectrum 1346 using the resulting frequency-domain data derived from the Fourier transform operation.

The details of a power spectrum and the square-root of the spectrum 1400 are illustrated in FIG. 14 as the details relate to the operation of the present invention to compute alternans indices. A power spectrum, and the square-root 1400 of its data, provides a measurement of the alternans energy that resides within a patient's ECG signal as represented by a PT-wave time-phase matrix and at a specific (relative) point in time during a PT-wave. After computing a power spectrum, the spectral analysis element 1930 measures the alternans energy 1420 at the 0.5 frequency cycles per cardiac cycle 1410 (cycles per beat). Each power spectrum is evaluated at the frequency of alternation (the Nyquist frequency, relativized to 0.5 alternans cycles per cardiac cycle), which corresponds to the N/2 position in the spectrum, where the number of data points used to compute a power spectrum is N, where $N=N_R$ for the reference time-phase matrices. The alternans energy is a microvolt measurement 1430 as the square-root of the power spectrum value found in the same position 1410 in the power spectrum, since a power spectrum (periodogram) is the square of the modulus of the discrete Fourier transform and is an estimate of a signal's power spectral density or energy. The microvolt alternans energy value 1430 is compared to the largest microvolt measurements 1440 prior to the 0.5 cycles/beat (in the range from approximately 0.3 cycles/beat to values immediately preceding the alternans value at 0.5 cycles/beat).

Figure 15:
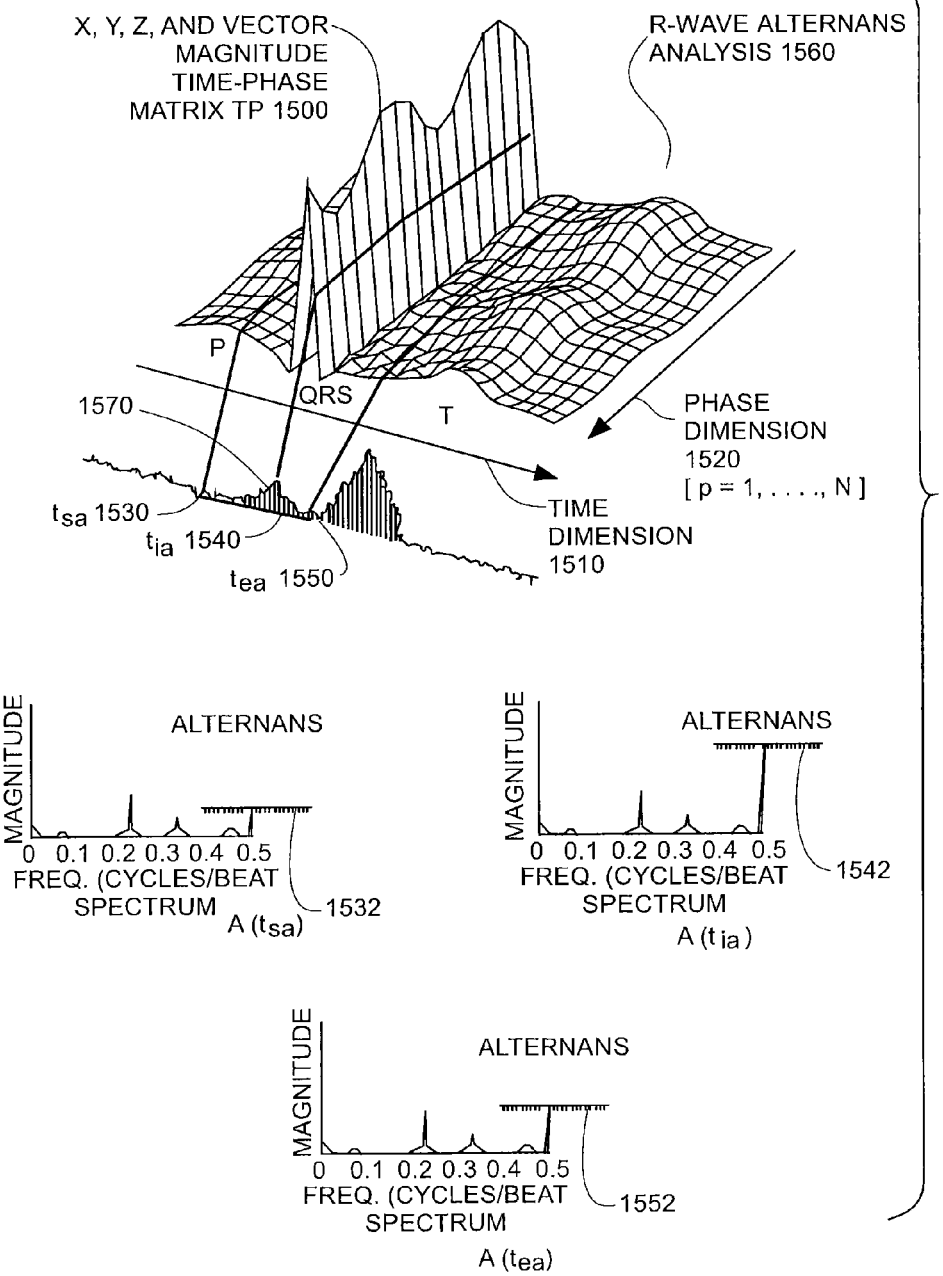
FIG. 15 illustrates a process of computing a plurality of power spectra for columns of phase data in the R-wave segment of a time-phase matrix of aligned PT-waves and the corresponding R-wave alternans energy curve.
Figure 16:
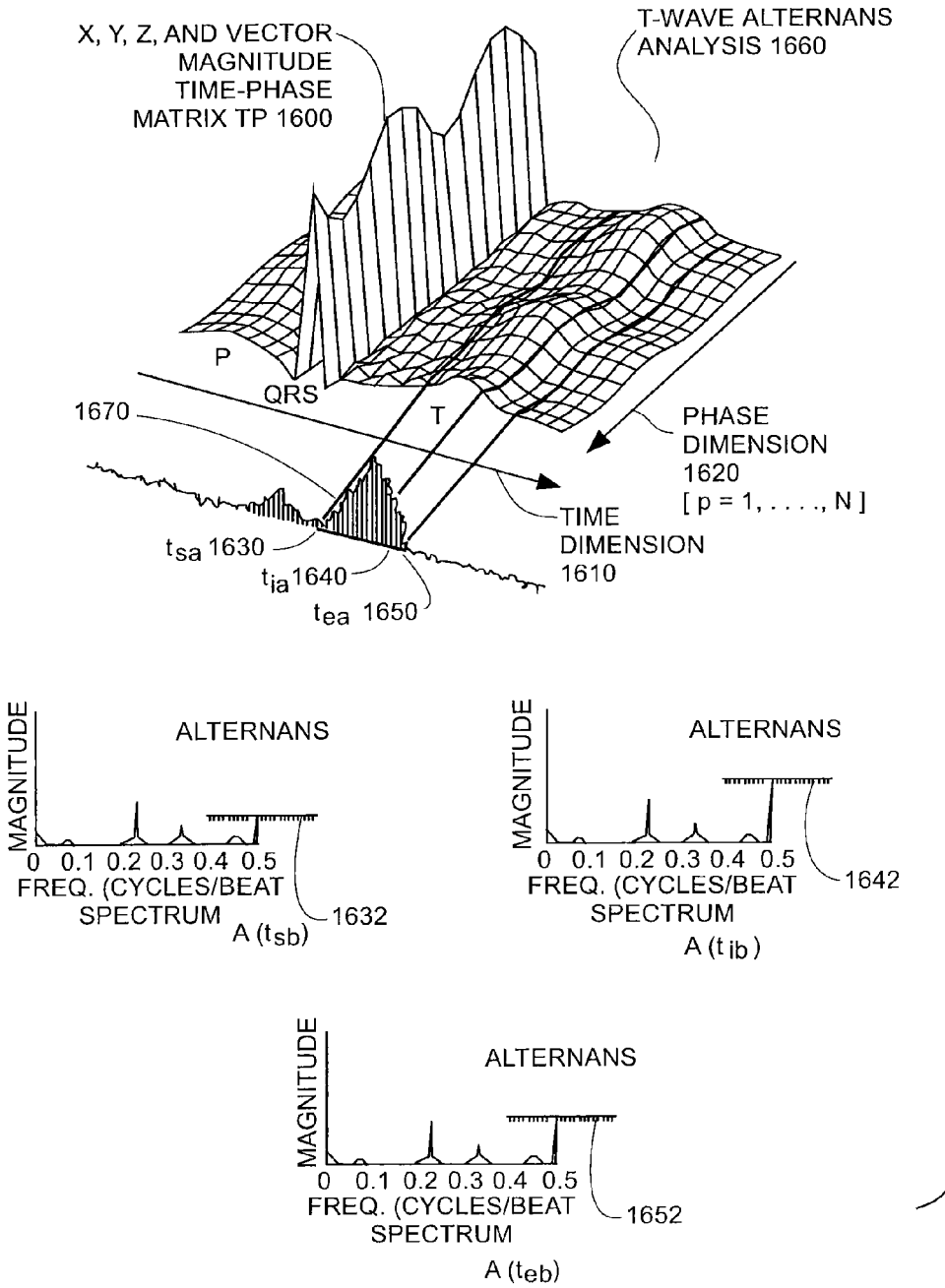
FIG. 16 illustrates a process of computing a plurality of power spectra for columns of phase data in the T-wave segment of a time-phase matrix of aligned PT-waves and the corresponding T-wave alternans energy curve.

As a fourth step, the software analysis element 1940 extracts the reference R-wave and T-wave alternans energy values as described in the third step to construct an alternans energy curve as illustrated in FIGS. 15 and 16. FIG. 15 illustrates the extraction of reference alternans energy values and their placement into the reference alternans energy curve for PT-wave data in the R-wave segment 1570 of a reference time-phase matrix illustrated by 1500 and called the R-wave alternans analysis 1560. FIG. 16 illustrates the extraction of reference alternans energy values and their placement into the same reference alternans energy curve for PT-wave data in the T-wave segment 1670 of a same reference time-phase matrix illustrated by 1600 and called the T-wave alternans analysis 1660.

As a fifth step, the software analysis element 1950 computes the reference PT-wave alternans energy indices. As a first illustration of an alternans energy index, analysis element 1950 sums the alternans energy values in the reference R-wave alternans energy curve segment 1570 and divides this summed value by the number of alternans energy values found in the segment 1570. For a reference time-phase matrix, the summed and normalized R-wave alternans energy values represent the reference energy of the alternans component of the ECG signal in the R-wave and is called a microvolt R-wave alternans index associated with the reference time-phase matrix. As a second illustration of an alternans energy index and using the same process steps, the analysis element 1950 sums the alternans energy values in the reference T-wave alternans energy curve segment 1670 and divides this summed value by the number of alternans energy values found in the segment 1670. For a reference time-phase matrix, the summed and normalized T-wave alternans energy values represent the reference energy of the alternans component of the ECG signal in the T-wave and is called a microvolt T-wave alternans index associated with the reference time-phase matrix. The index computation represents a finite and discrete integration method to determine the area under the alternans energy curve segments 1570 and 1670. The general details to these process steps for the analysis elements 1940 and 1950 are now described using FIGS. 15, 16, and 17.

For a time-phase matrix, FIG. 15 illustrates the computations to construct the reference microvolt R-wave alternans energy segment 1570 of the PT-wave alternans energy curve. As shown and previously described, a plurality of discrete power spectrums are computed from the start of the R-wave 240 to the end of the R-wave 250. The number of estimated power spectrums is equal to the number of digitized ECG data values that comprise an R-wave and is determined by the predetermined sampling rate at the start of a diagnostic Wedensky modulation test for a patient. For each time point in the time direction 1510 in the R-wave, a power spectrum is computed in the phase direction 1520 (along the phase dimension) of the time-phase matrix, thereby using the digitized ECG data values along each R-wave column in the PT-wave data of the time-phase matrix, starting with the column of phase data representing the start of the R-wave 240 and ending with the column of phase data representing the end of the R-wave 250. For a predetermined time-phase matrix TPX, TPY, TPZ, and VM, as a first step in the R-wave analysis process to construct the R-wave alternans energy segment 1570, the power spectrum and subsequent determination of the alternans energy value 1532 are shown as computed for the starting time point $t_{sa}$ 1530 for the R-wave, and, once computed, the R-wave alternans energy value $A(t_{sa})$ 1532 is placed into the corresponding time position $t_{sa}$ 1530 in R-wave alternans energy curve segment 1570. As an example of one of the intermediate steps in the R-wave analysis process to construct the R-wave alternans energy segment 1570, the power spectrum and subsequent determination of the alternans energy value 1542 are shown as computed for the intermediate time point $t_{ia}$ 1540 for the R-wave, and, once computed, the R-wave alternans energy value $A(t_{ia})$ 1542 is placed into the corresponding time position $t_{ia}$ 1540 in R-wave alternans energy curve segment 1570. As a final step in the R-wave analysis process to construct the R-wave alternans energy segment 1570, the power spectrum and subsequent determination of the alternans energy value 1552 are shown as computed for the ending time point $t_{ea}$ 1550 for the R-wave, and, once computed, the R-wave alternans energy value $A(t_{ea})$ 1552 is placed into the corresponding time position $t_{ea}$ 1550 in R-wave alternans energy curve segment 1570.

For a time-phase matrix, FIG. 16 illustrates the computations to construct the reference microvolt T-wave alternans energy segment 1670 of the PT-wave alternans energy curve. As shown and previously described, a plurality of discrete power spectrums are computed from the start of the T-wave 260 to the end of the T-wave 270. The number of estimated power spectrums is equal to the number of digitized ECG data values that comprise an T-wave and is determined by the predetermined sampling rate at the start of a diagnostic Wedensky modulation test for a patient. For each time point in the time direction 1610 in the T-wave, a power spectrum is computed in the phase direction 1620 (along the phase dimension) of the time-phase matrix, thereby using the digitized ECG data values along each T-wave column in the PT-wave data of the time-phase matrix, starting with the column of phase data representing the start of the T-wave 260 and ending with the column of phase data representing the end of the T-wave 270. For a predetermined time-phase matrix TPX, TPY, TPZ, and VM, as a first step in the T-wave analysis process to construct the T-wave alternans energy segment 1670, the power spectrum and subsequent determination of the alternans energy value 1632 are shown as computed for the starting time point $t_{sb}$ 1630 for the T-wave, and, once computed, the T-wave alternans energy value $A(t_{sb})$ 1632 is placed into the corresponding time position $t_{sb}$ 1630 in T-wave alternans energy curve segment 1670. As an example of one of the intermediate steps in the T-wave analysis process to construct the T-wave alternans energy segment 1670, the power spectrum and subsequent determination of the alternans energy value 1642 are shown as computed for the intermediate time point $t_{ib}$ 1640 for the T-wave, and, once computed, the T-wave alternans energy value $A(t_{ib})$ 1642 is placed into the corresponding time position $t_{ib}$ 1640 in T-wave alternans energy curve segment 1670. As a final step in the T-wave analysis process to construct the T-wave alternans energy segment 1670, the power spectrum and subsequent determination of the alternans energy value 1652 are shown as computed for the ending time point $t_{eb}$ 1650 for the T-wave, and, once computed, the T-wave alternans energy value $A(t_{eb})$ 1652 is placed into the corresponding time position $t_{eb}$ 1650 in T-wave alternans energy curve segment 1670.

Figure 17:
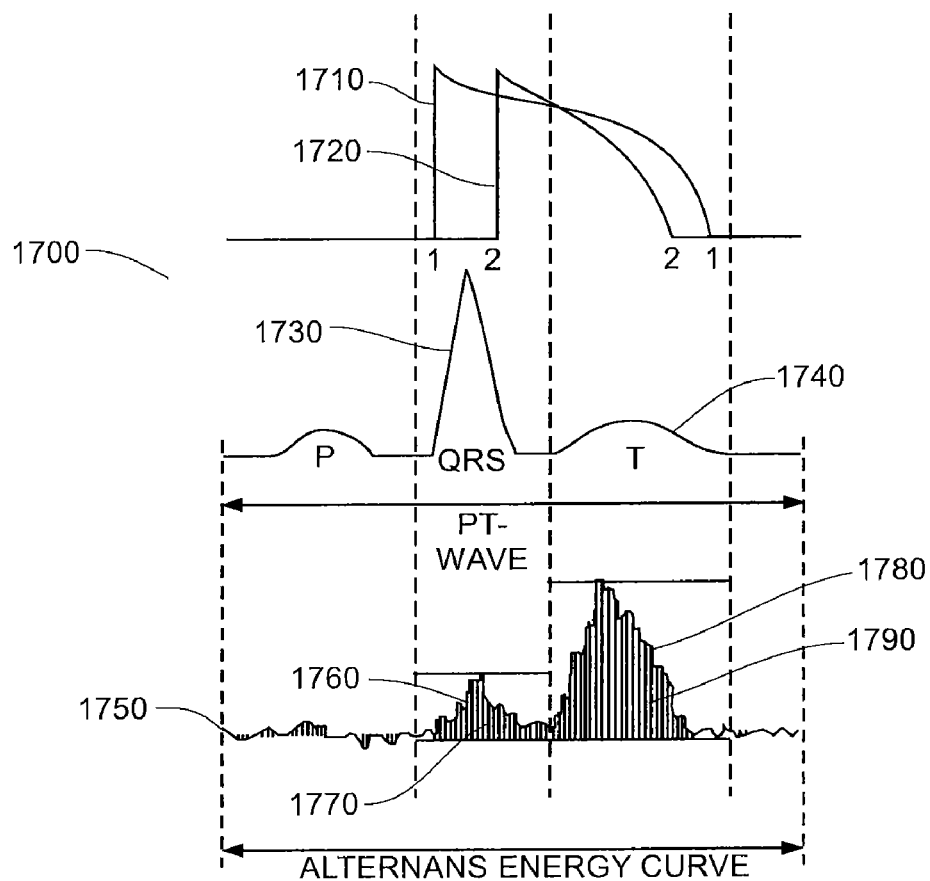
FIG. 17 illustrates a relationship between a myocardial cell action potential, an associated cardiac cycle as recorded on an ECG, and the alternans energy curve computed for a plurality of PT-waves in a time-phase matrix.

FIG. 17 illustrates the important relationships 1700 between myocardial cell action potentials 1710 and 1720 (depolarization and repolarization), the cardiac cycle's R-wave 1730 and T-wave 1740, and R-wave alternans energy curve segment 1760 and the T-wave alternans energy curve segment 1780 of the PT-wave alternans energy curve 1750. FIG. 17 first illustrates the action potential to cardiac cycle relationship for a typical ventricular endocardial cell 1710 (where its depolarization phase starts at the first number "1" and its repolarization phase ends at the second number "1") and for a typical ventricular epicardial cell 1720 (where its depolarization phase starts at the first number "2" and its repolarization phase ends at the second number "2"). Dependent upon the structure of the heart and the path of electrical wavefronts through the heart muscle (myocardium), the start of a ventricular endocardial action potential 1710 generally relates to time nearer to the start of the R-wave 1730 and the start of a ventricular epicardial action potential 1720 generally relates to time nearer to the end of the R-wave 1730. Similarly and in general fashion, the end of a ventricular endocardial action potential 1710 generally relates to time nearer to the end of the T-wave 1740 and the end of a ventricular epicardial action potential 1720 generally relates to time nearer to the start of the T-wave 1730.

FIG. 17 further illustrates these electrical activity relationships regarding action potentials and cardiac cycles to the R-wave alternans energy curve segment 1760 and the T-wave alternans energy curve segment 1780 of PT-wave alternans energy curve 1750 constructed by the present invention and previously illustrated in FIGS. 13, 14, 15 and 16. FIG. 17 illustrates the R-wave levels 1760 and T-wave levels 1780 of spectrally measured alternans energy measured at the N/2 position in the power spectrum (relativized to be measured at the 0.5 alternans per cardiac cycle) for each time position in the R-wave 1730 and the T-wave 1740 in the cardiac cycle, and therefore illustrates the plurality of spectrally measured alternans energy values 1760 for the R-wave and 1780 for the T-wave. FIG. 17 further illustrates the area 1770 under the R-wave alternans energy curve segment and the area 1790 under the T-wave alternans energy curve segment. The R-wave area 1770 is the index that is computed and provided for display and interpretation by the software spectral analysis elements 1940 and 1950 and illustrates an example of a microvolt R-wave alternans index for a time-phase matrix as a finite and discrete integration defined as a point by point average of the alternans energy values of the R-wave alternans energy curve segment 1760. The formula for the area 1770 is written as $$R_{AA} = \left[ \frac{\sum_{t=t_{sa}}^{t=t_{ea}} R_{AA}(t)}{R_N} \right],$$

where $R_{AA}(t)$ represents one of a plurality of values in the R-wave alternans energy curve (previously defined and illustrated as $A(t_{sa})$ 1532, $A(t_{ia})$ 1542, and $A(t_{ea})$ 1552), and $R_N$ represents the number of alternans energy curve values in the R-wave alternans energy curve segment 1760. In the same manner, the T-wave area 1790 is the index that is computed and provided for display and interpretation by the software spectral analysis elements 1940 and 1950 and illustrates an example of a microvolt T-wave alternans index for a time-phase matrix as a finite and discrete integration defined as a point by point average of the alternans energy values of the T-wave alternans energy curve segment 1780. The formula for the area 1790 is written as $$T_{AA} = \left[ \frac{\sum_{t=t_{sb}}^{t=t_{eb}} T_{AA}(t)}{T_N} \right],$$

where $T_{AA}(t)$ represents one of a plurality of values in the T-wave alternans energy curve (previously defined and illustrated as $A(t_{sb})$ 1632, $A(t_{ib})$ 1642, and $A(t_{eb})$ 1652), and $T_N$ represents the number of alternans energy curve values in the R-wave alternans energy curve segment 1790.

In this manner, a reference microvolt R-wave alternans index 1770 is computed by the software spectral analysis and alternans computing elements for the set of reference cardiac cycle R-waves in each X, Y, Z and vector magnitude signal using the time-phase matrices rTPX, rTPY, rTPZ, and the vector magnitude rVM. There are four reference microvolt R-wave alternans indices 1770. In a same manner and as a next step, a reference microvolt T-wave alternans index 1790 is computed by the software spectral analysis and alternans computing elements for the set of reference cardiac cycle T-waves in each X, Y, Z and vector magnitude signal using the time-phase matrices rTPX, rTPY, rTPZ, and the vector magnitude rVM. There are four reference microvolt T-wave alternans indices 1790. These computations and indices represent a significant improvement over the prior art regarding the explicit construction and subsequent analysis of the full and entire reference alternans energy curve 1750 for each of the reference time-phase matrices constructed using the reference PT-waves extracted from the ECG signals.

Figure 20:
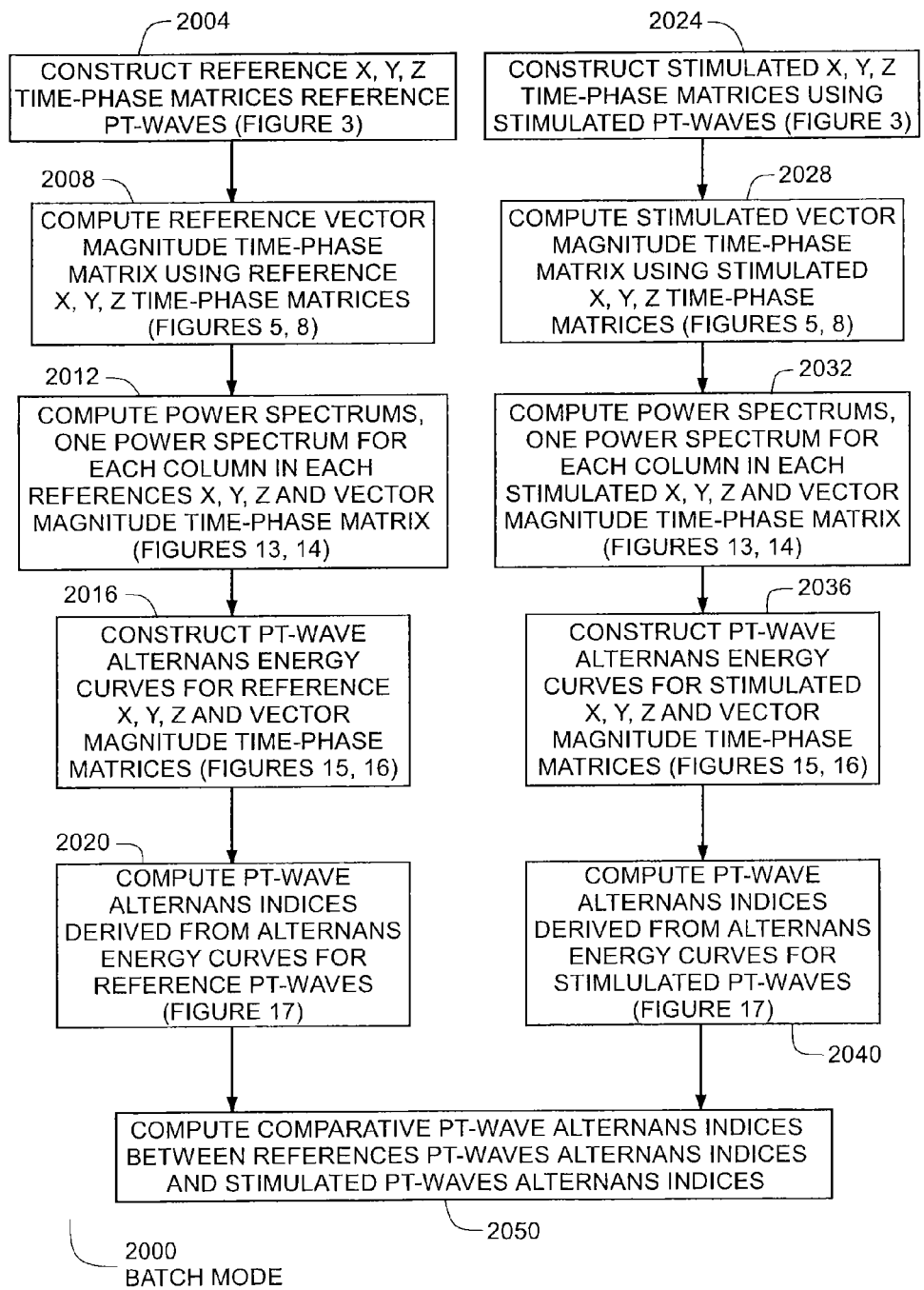
FIG. 20 illustrates a flowchart for a method of using a batch mode for analyzing a patient's Wedensky modulated ECG data (reference and stimulated ECG data) to compute R-wave and T-wave alternans indices in accordance with the invention.

FIG. 20 illustrates the steps operated by the software analysis elements described in FIG. 19 and applied to both the reference and the stimulated cardiac cycles derived from a Wedensky modulation test. The analysis elements 2004, 2008, 2012, 2016, and 2020 perform the same analysis steps for constructing time-phase matrices, alternans energy curves, and microvolt alternans indices as these elements are applied to the subset of the reference PT-waves and as these elements are elucidated by the description for analysis elements 1910, 1920, 1930, 1940, and 1950. Immediately following the conclusion of the operation of analysis element 2020, analysis elements 2024, 2028, 2032, 2036, and 2040 next perform the same analysis steps for constructing time-phase matrices, alternans energy curves, and microvolt alternans indices as these elements are applied to the subset of the stimulated PT-waves and as these elements are elucidated by the description for analysis elements 1910, 1920, 1930, 1940, and 1950. As a final step, software analysis element 2050 then computes comparative PT-wave alternans indices, such as the illustrated R-wave and T-wave alternans indices, to describe the differential PT-wave alternans energy between reference and stimulated PT-waves in the time-phase matrices.

In this manner and as illustrated in FIG. 20, a stimulated microvolt R-wave alternans index 1770 is computed by the software spectral analysis and alternans computing elements for the set of stimulated cardiac cycle R-waves in each X, Y, Z and vector magnitude signal using the time-phase matrices sTPX, sTPY, sTPZ, and the vector magnitude sVM. There are four stimulated microvolt R-wave alternans indices 1770. In a same manner and as a next step, a stimulated microvolt T-wave alternans index 1790 is computed by the software spectral analysis and alternans computing elements for the set of stimulated cardiac cycle T-waves in each X, Y, Z and vector magnitude signal using the time-phase matrices sTPX, sTPY, sTPZ, and the vector magnitude sVM. There are four stimulated microvolt T-wave alternans indices 1790. These computations and indices represent a significant improvement over the prior art regarding the explicit construction and subsequent analysis of the full and entire stimulated alternans energy curve 1750 for each of the stimulated time-phase matrices constructed using the stimulated PT-waves extracted from the ECG signals.

As an illustrative example of comparative R-wave alternans indices, and as process steps within the analysis element 2050, four reference microvolt R-wave alternans indices 1770 are computed by the present invention's software spectral analysis and alternans computing element 2020 for the set of time-phase matrices rTPX, rTPY, rTPZ, and the vector magnitude rVM. Next, four stimulated microvolt R-wave alternans indices 1770 are computed by the present invention's software spectral analysis and alternans computing element 2040 for the set of time-phase matrices sTPX, sTPY, sTPZ, and the vector magnitude sVM. The two sets of four microvolt R-wave alternans indices are next used to compute difference indices 2050. As an illustrative example, a difference microvolt R-wave alternans index for the X ECG signal is the absolute value of the difference between the reference and stimulated microvolt R-wave alternans indices constructed from the rTPX and sTPX time-phase matrices. As an example formula, the difference microvolt R-wave alternans index for the X ECG signal is written as $$DR_{AA(X)} = [R_{AA}(X_S) - R_{AA}(X_R)],$$

where the variable $R_{AA}(X_S)$ represents $R_{AA}$ derived from the reference X signal and $R_{AA}(X_R)$ represents $R_{AA}$ derived from the stimulated X signal. In this way, four difference microvolt R-wave alternans indices are computed, one difference index for each of the X, Y, Z, and vector magnitude ECG signals. The reference, stimulated, and difference indices are computed and presented to the physician-operator for review and for interpretation.

In addition, the two sets of four microvolt R-wave alternans indices 1770 are used to compute index ratios. As an illustrative example, a ratio microvolt R-wave alternans index for the X ECG signal is the ratio of the stimulated microvolt R-wave alternans index 1770 (constructed using sTPX) to the reference microvolt R-wave alternans index 1770 (constructed using rTPX). As an example formula, the ratio microvolt R-wave alternans index for the X ECG signal is written as $$DR_{AA(X)} = [R_{AA}(X_S) / R_{AA}(X_R)],$$

where the variable $R_{AA}(X_S)$ represents $R_{AA}$ derived from the reference X signal and $R_{AA}(X_R)$ represents $R_{AA}$ derived from the stimulated X signal. In this way, there are four ratio microvolt R-wave alternans indices, one ratio index for each of the X, Y, Z, and vector magnitude ECG signals. These ratio indices are computed and presented to the physician-operator for review and for interpretation.

In general, the pair of microvolt R-wave alternans indices 1770, one pair for each set of reference and stimulated PT-waves, can be combined in similar ways (weighted sums and weighted ratios) to provide an improved and more accurate measure of a patient's susceptibility to ventricular arrhythmias when compared to the microvolt R-wave alternans index presently computed and evaluated in clinical practice.

As an illustrative example of comparative T-wave alternans indices, and as process steps within the analysis element 2050, four reference microvolt T-wave alternans indices 1790 are computed by the present invention's software spectral analysis and alternans computing element 2020 for the set of time-phase matrices rTPX, rTPY, rTPZ, and the vector magnitude rVM. Next, four stimulated microvolt T-wave alternans indices 1790 are computed by the present invention's software spectral analysis and alternans computing element 2040 for the set of time-phase matrices sTPX, sTPY, sTPZ, and the vector magnitude sVM. The two sets of four microvolt T-wave alternans indices are next used to compute a combination of indices in the same manner as described for the R-wave alternans indices. These combinations include the absolute difference and the ratio indices. The reference, stimulated, difference, and ratio T-wave alternans indices are presented to the physician-operator for review and for interpretation. These new, weighted, normalized microvolt T-wave alternans indices, representing the changes due to subthreshold pacing to a subset of the totality of a patient's cardiac cycles during a Wedensky modulation test, are new indices and are described herein for the first time. These subthreshold pacing normalized microvolt T-wave alternans indices provide an improved diagnostic capability to determine a patient's susceptibility to ventricular arrhythmias.

In addition, the full set of eight microvolt alternans indices 1770 and 1790 are used to compute two types of R-wave normalized T-wave alternans index ratios. The R-wave normalized T-wave alternans index ratios measure the alternans energy measured in the T-wave in relationship to the amount of alternans energy that is measured in the R-wave and in the present invention these relationships are augmented by the alternans energy differences between reference and stimulated PT-waves. As an illustrative example for the first type, an R-wave difference-normalized T-wave index ratio for the X ECG signal is the ratio of the difference between the stimulated microvolt T-wave alternans index 1790 and the stimulated microvolt R-wave alternans index 1770 divided by the difference between the reference microvolt T-wave alternans index 1790 and the reference microvolt R-wave alternans index 1770. As an example formula, the R-wave difference-normalized T-wave index ratio for the X ECG signal is written as $$T_{AA(X)}^D = \left\lfloor \frac{T_{AA}(X_S) - R_{AA}(X_S)}{T_{AA}(X_R) - R_{AA}(X_R)} \right\rfloor.$$

In this way, there are four R-wave difference-normalized T-wave index ratio, one ratio index for each of the matched reference-stimulated X, Y, Z, and vector magnitude ECG signals. As an illustrative example for the second type, an R-wave ratio-normalized T-wave index ratio for the X ECG signal is the ratio of the ratio between the stimulated microvolt T-wave alternans index 1790 and the stimulated microvolt R-wave alternans index 1770 divided by the ratio between the reference microvolt T-wave alternans index 1790 and the reference microvolt R-wave alternans index 1770. As an example formula, the R-wave ratio-normalized T-wave index ratio for the X ECG signal is written as $$T_{AA(X)}^R = \left\lfloor \frac{T_{AA}(X_S)}{R_{AA}(X_S)} \cdot \frac{R_{AA}(X_R)}{T_{AA}(X_R)} \right\rfloor.$$

In this way, there are four R-wave difference-normalized T-wave index ratio, one ratio index for each of the matched reference-stimulated X, Y, Z, and vector magnitude ECG signals. These two types of R-normalized T-wave alternans ratio indices are computed and presented to the physician-operator for review and for interpretation.

For a time-phase matrix and in the same manner as described for R-waves and T-waves, the present invention computes a plurality of microvolt P-wave and ST-segment alternans indices based on the reference and stimulated PT-wave structures. The estimates of the discrete power spectrum of the P-wave and ST-segment at points in time in the P-wave and ST-segment are computed, such that a plurality of discrete power spectrums are computed from the start of the P-wave 220 to the end of the P-wave 230 and from the start of the ST-segment 250 to the end of the ST-segment 260 as illustrated in FIG. 2. The present invention's software spectral analysis and alternans computing elements which have been previously described for the analysis of the R-wave and T-wave structures are also now applied to the P-wave and ST-segment, and these various difference and ratio indices are presented to the physician-operator for review and for interpretation.

As a first illustrative operations example, the physician-operator of the present invention designates a first plurality of a patient's cardiac cycles as the reference cardiac cycles, for example the first at least 8 cardiac cycles are recorded from a patient as the first part of the patient's ECG signals. The operator sets a first pair of parameters to pre-select these first at least 8 cardiac cycles as the cycles that will not receive a synchronized injection of a subthreshold electrical pulse. The first pair of parameters are $K_{R1}$, the number of first cardiac cycles in a cardiac cycle sequence that are reference cardiac cycles, and $K_{R2}$, the number of reference cardiac cycle sequences. In this example, the pair $(K_{R1}, K_{R2})=(8,1)$, which represents 8 consecutive reference cardiac cycles acquired in the ECG signals from a patient during a test.

The operator also designates a second plurality of a patient's cardiac cycles as the stimulated cardiac cycles, for example the second at least 8 cardiac cycles in the ECG signals are then stimulated at a predetermined stimulation point in each cardiac cycle and are recorded from a patient as the second part of the patient's ECG signals. The operator sets a second pair of parameter to pre-select these second at least 8 cardiac cycles as the cycles that will receive a synchronized injection of a subthreshold electrical pulse. The second pair of parameters are $K_{S1}$, the number of second cardiac cycles in a cardiac cycle sequence that are stimulated cardiac cycles, and $K_{S2}$, the number of stimulated cardiac cycle sequences. In this example, the pair $(K_{S1}, K_{S2})=(8,1)$, which represents 8 consecutive stimulated cardiac cycles acquired in the ECG signals from a patient during a test. Using these recorded reference and stimulated cardiac cycles in the ECG signals, the present invention constructs the time-phase matrices and computes the associated microvolt R-wave and T-wave alternans indices described herein. In this illustration, the reference microvolt R-wave and T-wave alternans indices for the vector magnitude rVM corresponds to the conventional alternans ECG morphology index for the R-wave. This mode of operation of the present invention is called the batch mode 2000. In a second illustrative example and in a electrically noisy environment, an operator may wish to perform the test over many cardiac cycles to increase the signal to noise ratios in the ECG signals. The operator may therefore preselect the pair $(K_{R1}, K_{R2})=(100,1)$ and the pair $(K_{S1}, K_{S2})=(100,1)$. Upon the start of a next Wedensky modulation test, the operator acquires a first group of 100 reference cardiac cycles and then a second group of 100 stimulated (Wedensky modulated) cardiac cycles for a total of 200 consecutive cardiac cycles per ECG signal. The associated ECG signals are next processed by the software analysis elements to compute batch mode 2000 diagnostic indices. For the $K_{R1}$ and $K_{S1}$ parameters, the smallest value is $1*10^0$ and the highest value is $1*10^4$. For the $K_{R2}$ and $K_{S2}$ parameters, the smallest value is $1*10^0$ and the highest value is $1*10^3$. The highest values are also limited by the product $K_{R1}*K_{R2}$ less than $1*10^4$ and the product $K_{S1}*K_{S2}$ less than $1*1^4$.

Figure 21:
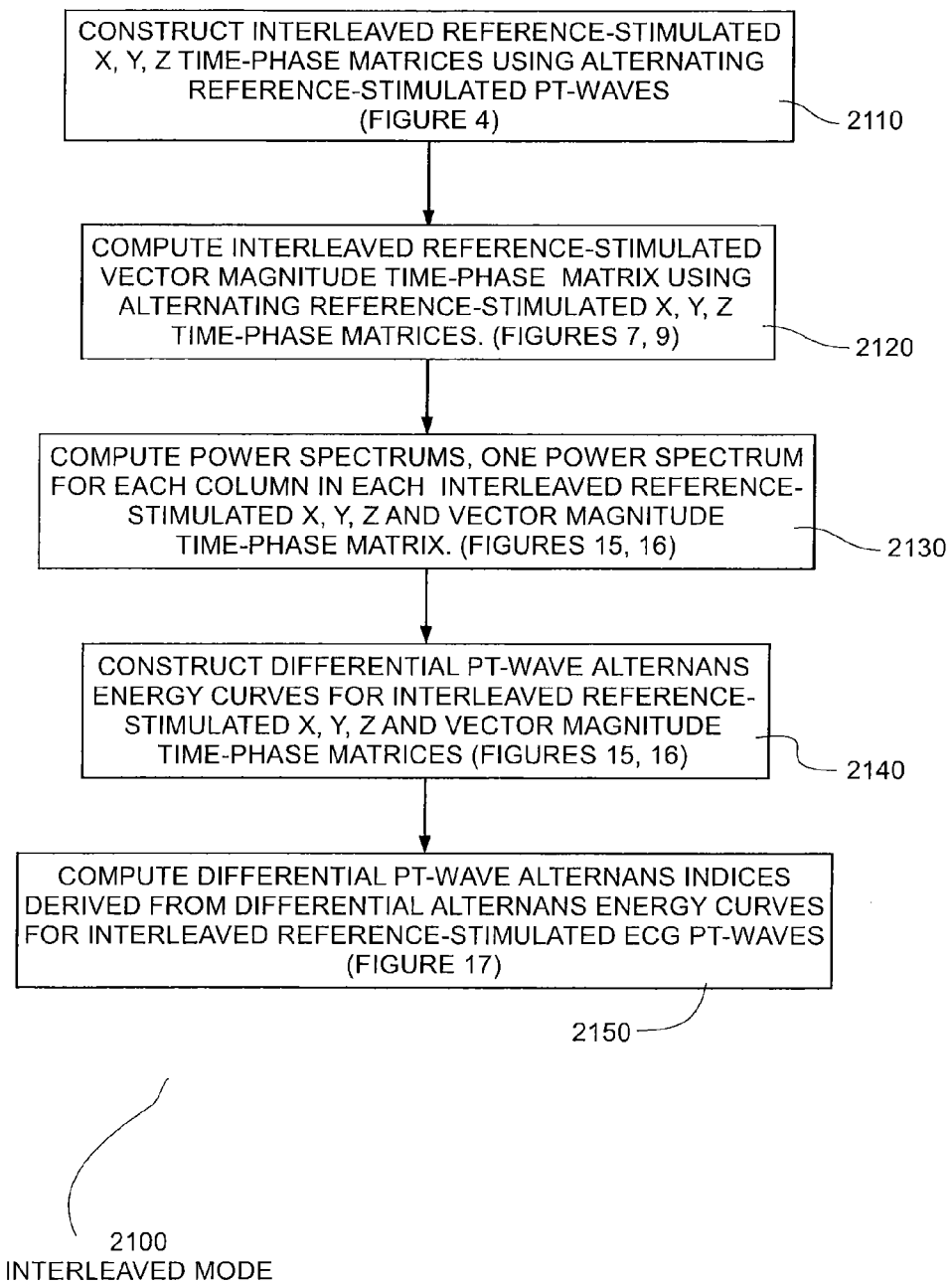
FIG. 21 illustrates a flowchart for a method of using an interleaved mode for analyzing a patient's Wedensky modulated ECG data (interleaved reference-stimulated ECG data) to compute R-wave and T-wave alternans indices in accordance with the invention.

FIG. 21 illustrates the steps operated by the software analysis elements described in FIG. 19 and applied to the interleaved reference-stimulated cardiac cycles derived from a Wedensky modulation test. The analysis elements 2110, 2120, 2130, 2140, and 2150 perform the same analysis steps for constructing time-phase matrices, alternans energy curves, and microvolt alternans indices as these elements are applied to the interleaved reference-stimulated time-phase matrices iTPX, iTPY, iTPZ, and iVM as representations of the interleaved reference-stimulated PT-waves and as these software analysis elements are elucidated by the description for analysis elements 1910, 1920, 1930, 1940, and 1950. The software analysis elements 2110, 2120, 2130, 2140, and 2150 computes integrated comparative PT-wave indices, as illustrated by R-wave and T-wave alternans indices, to describe the differential PT-wave alternans energy between reference and stimulated PT-waves by computing the R-wave and T-wave alternans indices using the interleaved reference-stimulated PT-waves in each of the time-phase matrices. These comparative R-wave and T-wave alternans indices are integrated by constructing time-phase matrices using the naturally occurring order of the PT-waves in the ECG signals and by applying subthreshold pulsing to interleaved cardiac cycles during a Wedensky modulation test. This new type of combination of the time-phase data further supports the present invention's method to apply subthreshold pulsing to the myocardial tissue in an interleaved manner to magnify the alternans as it relates to physiological alternans patterns due to compromised myocardial depolarization and repolarization caused by complications from ischemia and myocardial infarction substrate, and thereby increases the ability to measure alternans without strenuous physical or pharmacological stress.

As a second illustrative operations example, the physician-operator of the present invention designates a first plurality of a patient's cardiac cycles as the reference cardiac cycles, for example at least 8 cardiac cycles, and the operator also designates a second plurality of a patient's cardiac cycles as the stimulated cardiac cycles, for example at least 8 cardiac cycles, and configures the parameters of the present invention such that every other cardiac cycle is stimulated at a predetermined stimulation point and the total of these at least 16 cardiac cycles are recorded from a patient and are the totality of the patient's ECG signals. In this example, the pair $(K_{R1}, K_{R2})=(1,8)$ and the pair $(K_{S1}, K_{S2})=(1,8)$. Using these recorded reference and stimulated cardiac cycles in the ECG signals, the present invention constructs a form of the interleaved reference-stimulated time-phase matrices and computes the associated interleaved reference-stimulated and now integrated microvolt R-wave and T-wave alternans indices described herein. This mode of operation of the present invention is called the interleaved mode 2100. In a second illustrative example and in a electrically noisy environment, an operator may wish to perform the test over many cardiac cycles to increase the signal to noise ratios in the ECG signals. The operator may therefore preselect the pair $(K_{R1}, K_{R2})=(1, 250)$ and the pair $(K_{S1}, K_{S2})=(1,250)$. Upon the start of a next Wedensky modulation test, the operator acquires a total of 500 consecutive cardiac cycles per ECG signal comprising 250 reference cardiac cycles alternating every other cardiac cycle with 250 stimulated cardiac cycles. The associated ECG signals are next processed by the software analysis elements to compute interleaved mode 2100 diagnostic indices.

The Wedensky modulation pairs $(K_{R1}, K_{R2})$ and $(K_{S1}, K_{S2})$ are default settings that can be preselected by an operator when preparing the present invention to apply its default Wedensky modulation testing patterns during the course of a Wedensky modulation test. The present invention's electrical subthreshold pulsing and software control elements provide significant flexibility to defining Wedensky modulated series of cardiac cycles during a testing procedure. The present invention's interface provides a screen to enter a predetermined Wedensky modulation pattern that serves as a part of a Wedensky modulation and analysis instruction set used by the present invention's pulsing delivery hardware and pulsing control software elements. These hardware and software elements apply synchronized subthreshold pulsing to the cardiac cycles of a patient during the course of a test as taught by the Wedensky modulation instruction set. The instruction set comprises three elements. The first instruction set element is the number of times that the Wedensky modulation pattern is applied to the patient. The second element is a general Wedensky modulation pattern, which comprises a finite list of positive integers. Each number in the list represents the number of consecutive cardiac cycles to serve either as reference cardiac cycles or as stimulated cardiac cycles, starting with reference cardiac cycles. The third instruction set element is the analysis mode flag. The analysis mode flag is set to batch analysis mode (=1) or interleaved analysis mode (=2).

As a first illustrative example, the equivalent Wedensky modulation instruction set for the batch mode pairs $(K_{R1}, K_{R2})=(100,1)$ and $(K_{S1}, K_{S2})=(100,1)$ is (1; 100, 100; 1). As a second illustrative example, the equivalent Wedensky modulation instruction set for the interleaved mode pairs $(K_{R1}, K_{R2})=(1, 250)$ and $(K_{S1}, K_{S2})=(1, 250)$ that produce interleaved stimulated cardiac cycles is (250; 1, 1; 2).

As a third illustrative example, an operator can enter a Wedensky modulation instruction set (150; 2, 1, 1, 2; 1). When a Wedensky test is next started, the electrical subthreshold pulsing and software control elements apply the Wedensky pattern by first acquiring two reference (non-stimulated) cardiac cycles, next applying a subthreshold pulse to the third cardiac cycle while simultaneously acquiring the now stimulated cardiac cycle, next acquiring a fourth reference (non-stimulated) cardiac cycle, and next applying a subthreshold pulse to the fifth and sixth cardiac cycles while simultaneously acquiring these now stimulated cardiac cycles. The electrical subthreshold pulsing and software control elements repeat the administration of this Wedensky modulation pattern 150 times, thereby acquiring 900 cardiac cycles in each ECG signal, at which time the Wedensky modulation portion of the test stops and the Wedensky analysis portion of the test begins by separating the reference cardiac cycle PT-waves into the reference time-phase matrices and the stimulated cardiac cycle PT-waves into the stimulated time-phase matrices in preparation for batch mode analysis.

Figure 22:
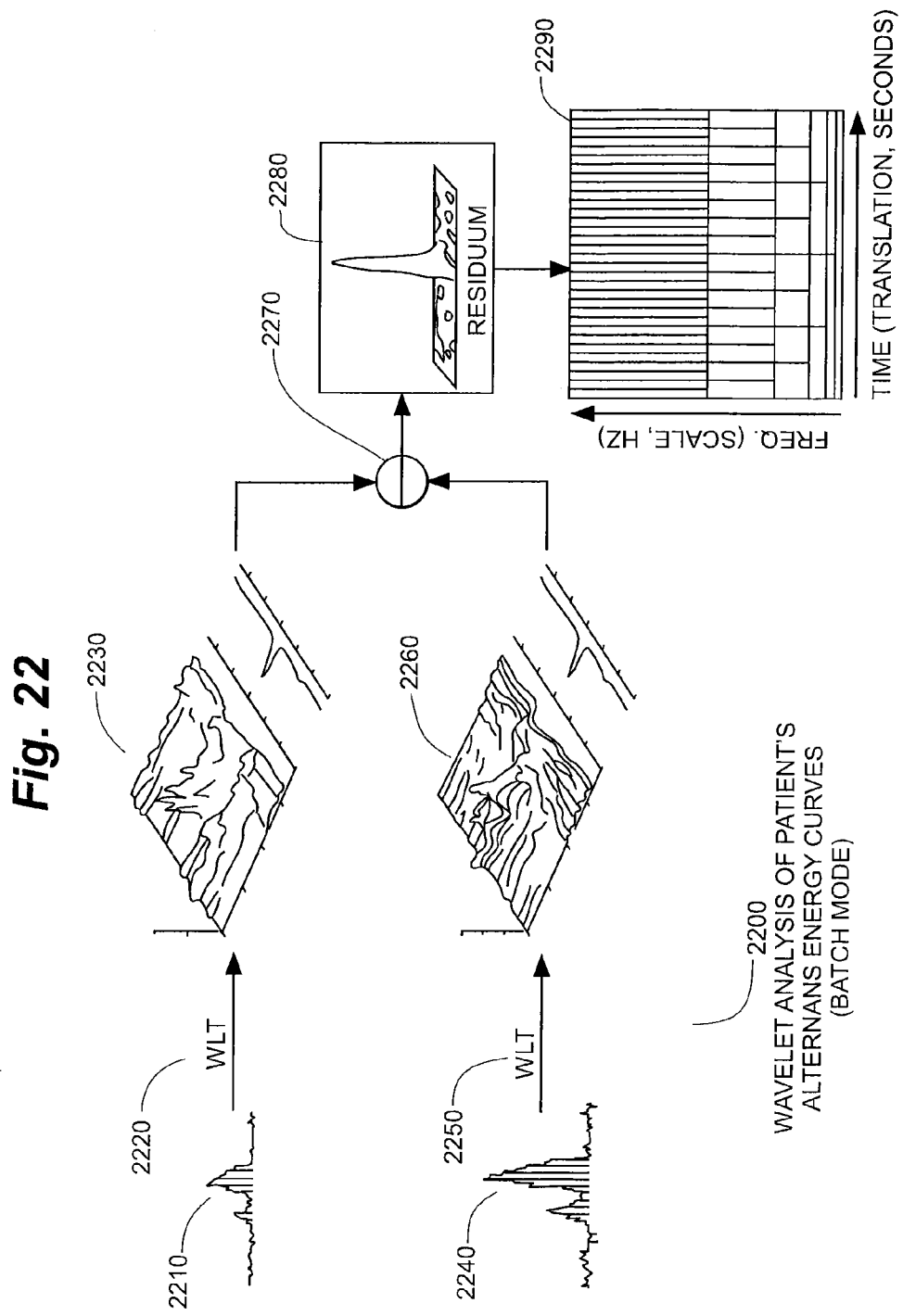
FIG. 22 illustrates a procedure for comparing an alternans energy curve computed using reference-based PT-waves to an alternans energy curve computed using stimulation-based PT-waves (Wedensky modulated PT-waves) by computing their respective continuous wavelet transforms and continuous wavelet residuum in accordance with the invention.
Figure 23:
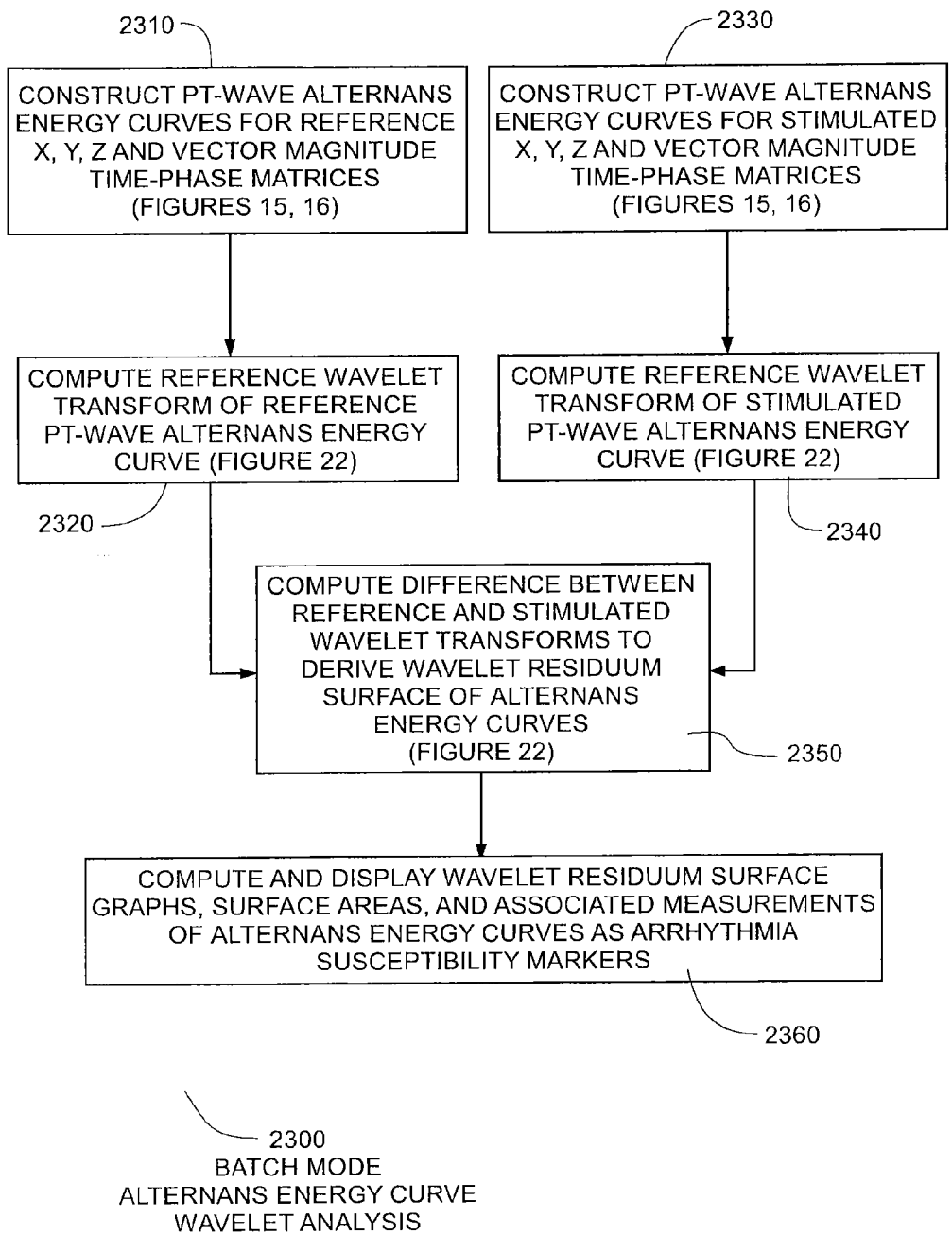
FIG. 23 illustrates a flowchart for a method of comparing alternans energy curves derived from reference-based and stimulation-based PT-wave time-phase matrices using continuous wavelet transforms and residuum to compute R-wave and T-wave alternans indices in accordance with the invention.

As a fourth illustrative example, an operator can enter a Wedensky modulation instruction set (200; 4, 4; 2). When a Wedensky test is next started, the electrical subthreshold pulsing and software control elements apply the Wedensky pattern by first acquiring four reference (non-stimulated) cardiac cycles, and next applying a subthreshold pulse to the next four cardiac cycle while simultaneously acquiring these now stimulated cardiac cycles. The electrical subthreshold pulsing and software control elements repeat the administration of this Wedensky modulation pattern 200 times, thereby acquiring 800 cardiac cycles in each ECG signal, at which time the Wedensky modulation portion of the test stops and the Wedensky analysis portion of the test begins by placing the 800 cardiac cycle PT-waves into the interleaved reference-stimulated time-phase matrices as a first initialization step to prepare for interleaved mode analysis. FIGS. 22 and 23 illustrate the application of the present invention's methods and apparatus to the PT-wave alternans energy curves 1750 constructed for each reference time-phase matrix and for each stimulated time-phase matrix. In FIGS. 22 and 23, the first step 2310 of the software analysis elements constructs the reference PT-wave alternans energy curve 2210 for each of the reference time-phase matrices rTPX, rTPY, rTPZ, and rVM (as previously described in this specification). The second step 2320 computes 2220 the reference continuous wavelet transform 2230 of these reference PT-wave alternans energy curves 2210. As shown, the third step 2330 of the software analysis elements constructs the stimulated PT-wave alternans energy curve 2240 for each of the stimulated time-phase matrices sTPX, sTPY, sTPZ, and sVM (as previously described in this specification) and the fourth step 2340 computes 2250 the stimulated continuous wavelet transform 2260 of these stimulated PT-wave alternans energy curves 2240. The fifth step 2350 in the analysis method computes the difference 2270 between the reference and stimulated continuous wavelet transforms 2230 and 2260 for the energy curves 2210 and 2240, respectively, to construct a wavelet surface residuum 2280 for the alternans energy curves.

As a sixth step, the analysis element 2360 computes weighted arithmetic, geometric, and harmonic averages, absolute differences, and normalizing ratios using the wavelet residuum coefficients. These indices are computed values that represent discriminating morphology features between the reference alternans energy curve and the stimulated alternans energy curve. This process 2200 and 2300 is the batch mode for computing alternans energy curve indices using continuous wavelet transform analysis.

Figure 24:
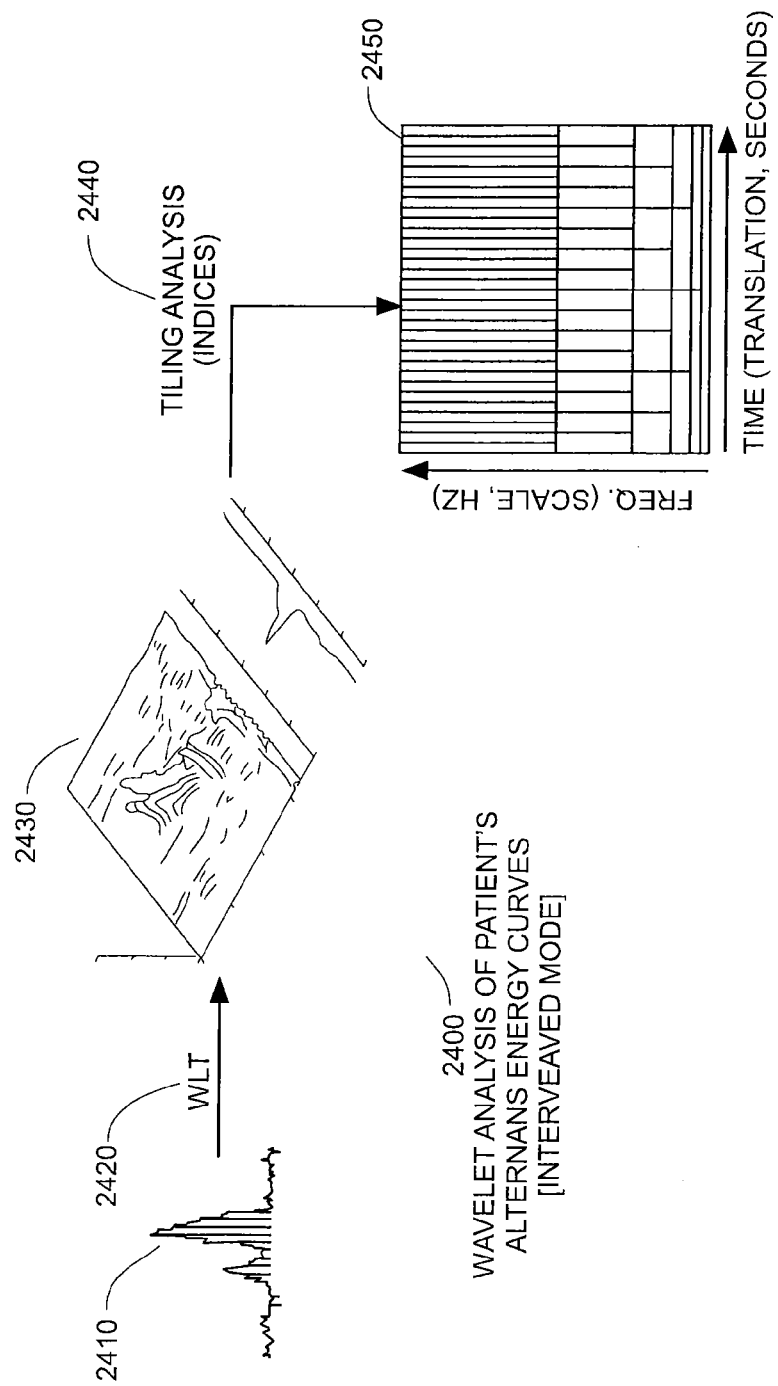
FIG. 24 illustrates a procedure for computing alternans indices using an alternans energy curve derived from interleaved reference-stimulation PT-waves and by computing its continuous wavelet transform, its discrete wavelet packet transform, and combining a plurality of wavelet coefficients using wavelet packet tiling in accordance with the invention.
Figure 25:
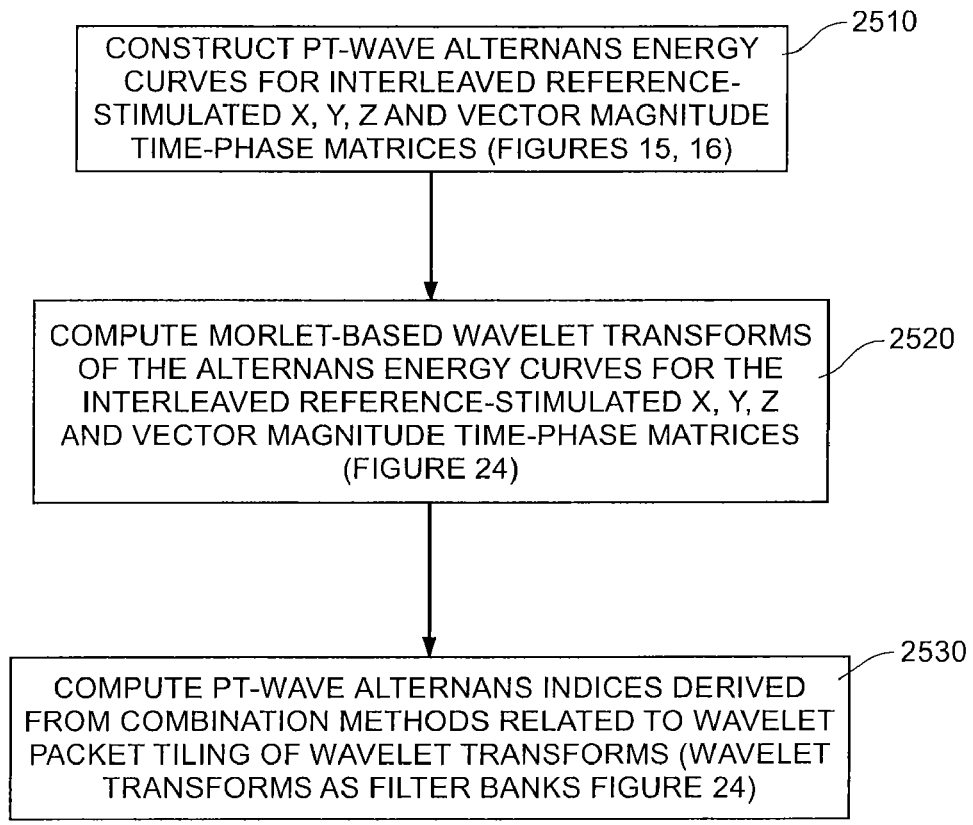
FIG. 25 illustrates a flowchart for a method of computing alternans indices using an alternans energy curve derived from interleaved reference-stimulation PT-waves and by computing its continuous wavelet transform, its discrete wavelet packet transform, and combining a plurality of wavelet coefficients using wavelet packet tiling in accordance with the invention.

FIGS. 24 and 25 illustrate the application of the present invention's methods and apparatus to the PT-wave alternans energy curves 1750 constructed for each interleaved reference-stimulated time-phase matrix. In FIGS. 24 and 25, the first step 2510 of the software analysis elements constructs the interleaved reference-stimulated PT-wave alternans energy curve 2410 for each of the interleaved reference-stimulated time-phase matrices iTPX, iTPY, iTPZ, and iVM (as previously described in this specification). The second step 2520 computes, using the continuous wavelet transform methods (WLT) 2420, the interleaved reference-stimulated continuous wavelet transform 2430 of these interleaved reference-stimulated PT-wave alternans energy curves 2410. As a third step, the analysis element 2530 computes weighted arithmetic, geometric, and harmonic averages, absolute differences, and normalizing ratios using the wavelet transform coefficients. These indices are computed values that represent magnified morphology features within the interleaved reference-stimulated alternans energy curve for a patient with a high likelihood for ventricular arrhythmias when compared to the same feature values for a patient with a low likelihood for ventricular arrhythmias. As a fourth step, using the multiresolution algorithm and the wavelet packet transform (WPT), weighting schemes are applied to the wavelet packet tiling representation 2450 to compute the alternans energy indices for the interleaved reference-stimulated alternans energy curve 2410. Illustrative examples of such weighting schemes to compute important diagnostic indices are described in detail in FIG. 26. Therefore, the process 2400 and 2500 is the interleaved mode for computing alternans energy curve indices using continuous wavelet transform and discrete wavelet packet transform analysis.

Figure 26:
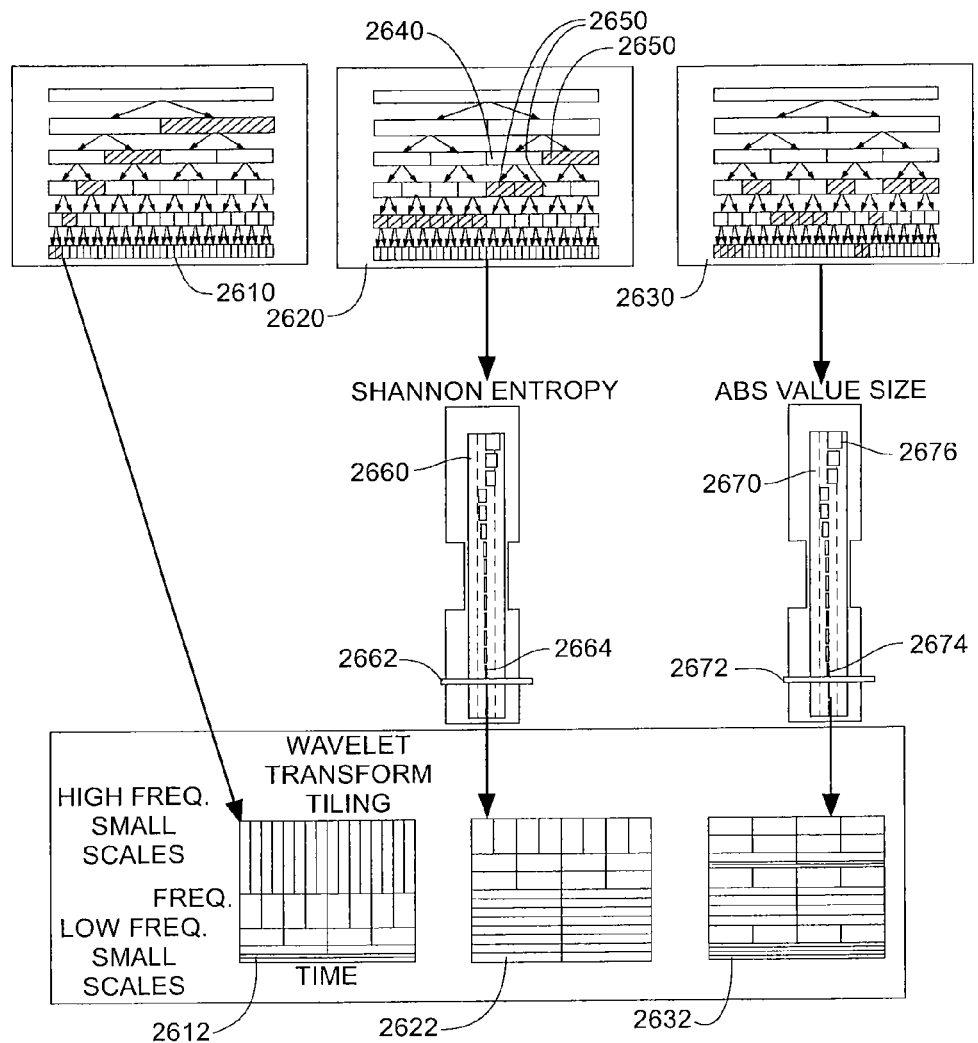
FIG. 26 illustrates examples of wavelet coefficients represented as wavelet packet tiling available for alternans index computations following wavelet transformation using a multiresolution algorithm in accordance with the invention.

FIG. 26 together with its associated detailed description illustrate the wavelet packet tiling representations and associated alternans energy curve indices. The wavelet packet transform (WPT) is generalized multiresolution decomposition of a signal with the multiresolution algorithm applied to each component at each scale level in the discrete wavelet transform. Using the WPT signal decomposition, both the approximation (low-frequency) and detailed (high-frequency) wavelet coefficients are iteratively decomposed. At each scale level, the WPT partitions the time-frequency plane into rectangles of constant aspect ratio, called tiles. FIG. 26 illustrates three wavelet packet decompositions 2610, 2620, and 2630, and associated tiling 2612, 2622, and 2632 for example alternans energy curves 1750 for three unique patients. A wavelet packet decomposition depends directly on the alternans energy information contained in a patient's alternans energy curve. The method for index construction for an alternans energy curve automatically selects wavelet packets and hence the associated tiling. The details to the method of index construction for alternans energy curves is now described in two illustrative examples.

As a first illustrative example of constructing an alternans energy curve index using WPT tiles, WPT coefficients are automatically selected based on the Shannon entropy measure (the minimum entropy criterion). At each scale, each pair of partitioned coefficients 2640 is compared with the singleton coefficient 2650 from which the pair was derived. If the combination of the coefficient pair has smaller entropy than the coefficient from which the pair was derived, then the coefficient pair 2640 is retained. Otherwise the original coefficient 2650 is retained. This comparison and selection process is iterated for each coefficient at each scale from the first scale to the last scale. Following the entropy-sorting step of the wavelet coefficients, in order of decreasing entropy contribution 2660, the wavelet coefficients are summed until the sum is larger than a predetermined entropy threshold 2662. The last wavelet coefficient added to the sum, which is the wavelet with the smallest contributing entropy value, is called the entropy wavelet coefficient $w_e$ 2664. The retained coefficients are then summed to form an alternans energy curve index representing the alternans energy curve. As part of this example illustration, this process produces wavelet packet decompositions 2620 and the retained coefficients create an optimal tiling 2622 of the time-frequency plane.

As a second illustrative example of constructing an alternans energy curve index using WPT tiles, WPT coefficients are automatically selected based on the size of the coefficients. Regardless of scale, all WPT coefficients are sorted into decreasing size 2670 of the absolute value of each coefficient. In general, wavelets with larger coefficients are positioned in time to better align their positive phase with the highest points in an alternans energy curve and their negative phase with the lowest point in the alternans energy curve. Following the size-sorting step of the wavelet coefficients, the smallest wavelet coefficient greater than a predetermined energy threshold 2672 is determined, and is called the central wavelet coefficient $w_c$ 2674. All coefficients from the largest coefficient 2676 down to $w_c$ 2674 are retained. The retained coefficients are next summed to form an alternans energy curve index representing the alternans energy curve. As part of this example illustration, this process produces wavelet packet decompositions 2630 and the retained coefficients create an optimal tiling 2632 of the time-frequency plane.

In this manner, a physician-operator selects a process to compute a wavelet-based alternans energy curve index for a patient, and constructs an interpretable wavelet decomposition of the alternans energy curve for the patient, whereby the alternans energy information in the curve is summarized to represent the patient's susceptibility to arrhythmia. Depending on the choice preselected for the entropy-sort threshold, the entropy wavelet coefficient $w_e$ 2664 also serves as an alternans energy curve index. Depending on the choice preselected for the size-sort threshold, the central wavelet coefficient $w_c$ 2674 also serves as an alternans energy curve index. Detailed descriptions of wavelet packet tiling and index construction are presented in the previously incorporated reference by Addison and the books (a) Addison PS, The Illustrated Wavelet Transform Handbook, Institute of Physics Publishing, Bristol BS1 6BE, UK, 2002, and (b) Burrus C S, Gopinath R A, Guo H, Introduction To Wavelets And Wavelet Transforms, A Primer, Prentice Hall, Upper Saddle River, N.J. 07458, US, 1998.

As an alternative embodiment of the present invention, the associated time-phase matrices are combined following their construction and prior to computing the microvolt R-wave and T-wave alternans indices. As an illustration to this method to the present invention regarding the combination of the time-phase matrices, the reference time-phase matrix rTPX for the X ECG signal is subtracted from the stimulated time-phase matrix sTPX, thereby producing a difference time-phase matrix for the X ECG signal, herein labeled dTPX, prior to computing the R-wave and T-wave alternans indices. In this manner, the time-phase software computation elements of the present invention compute the set of differenced time-phase matrices dTPX, dTPY, dTPZ, and dVM. The index computing software elements next compute the microvolt R-wave and T-wave alternans indices using these differenced time-phase matrices dTPX, dTPY, dTPZ, and dVM matrices. The resulting R-wave and T-wave alternans indices reflect the significantly larger electrophysiological fluctuations in the R-wave and T-wave due to the changes in depolarization and repolarization that are intensified by the pattern of subthreshold pulsing applied to a patient during the recording of the patient's ECG signals.

Figure 27:
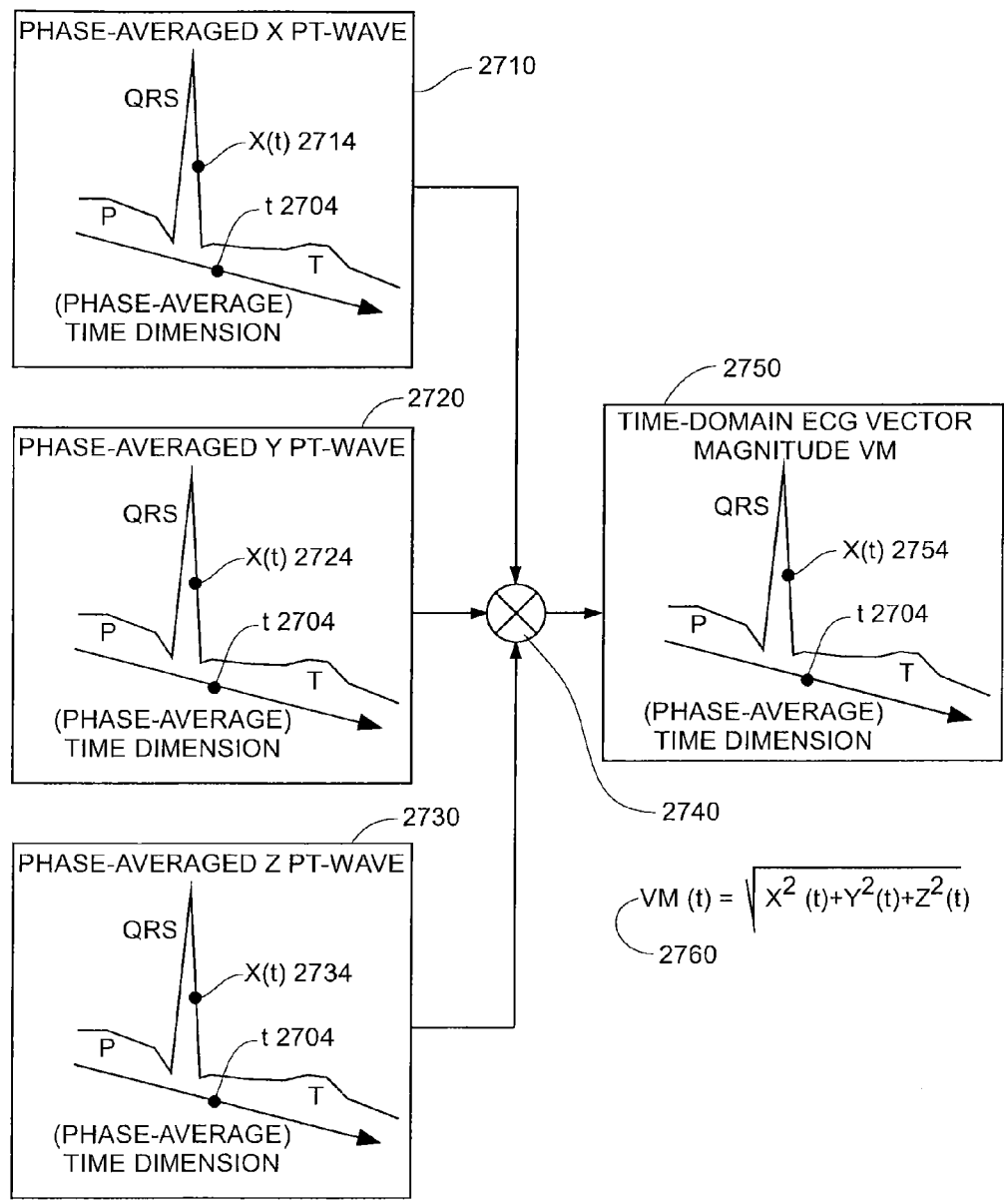
FIG. 27 illustrates a method for combining 1-dimensional phase-averaged X, Y, and Z PT-waves into a 1-dimensional time-domain vector magnitude VM in accordance with the invention.
Figure 28:
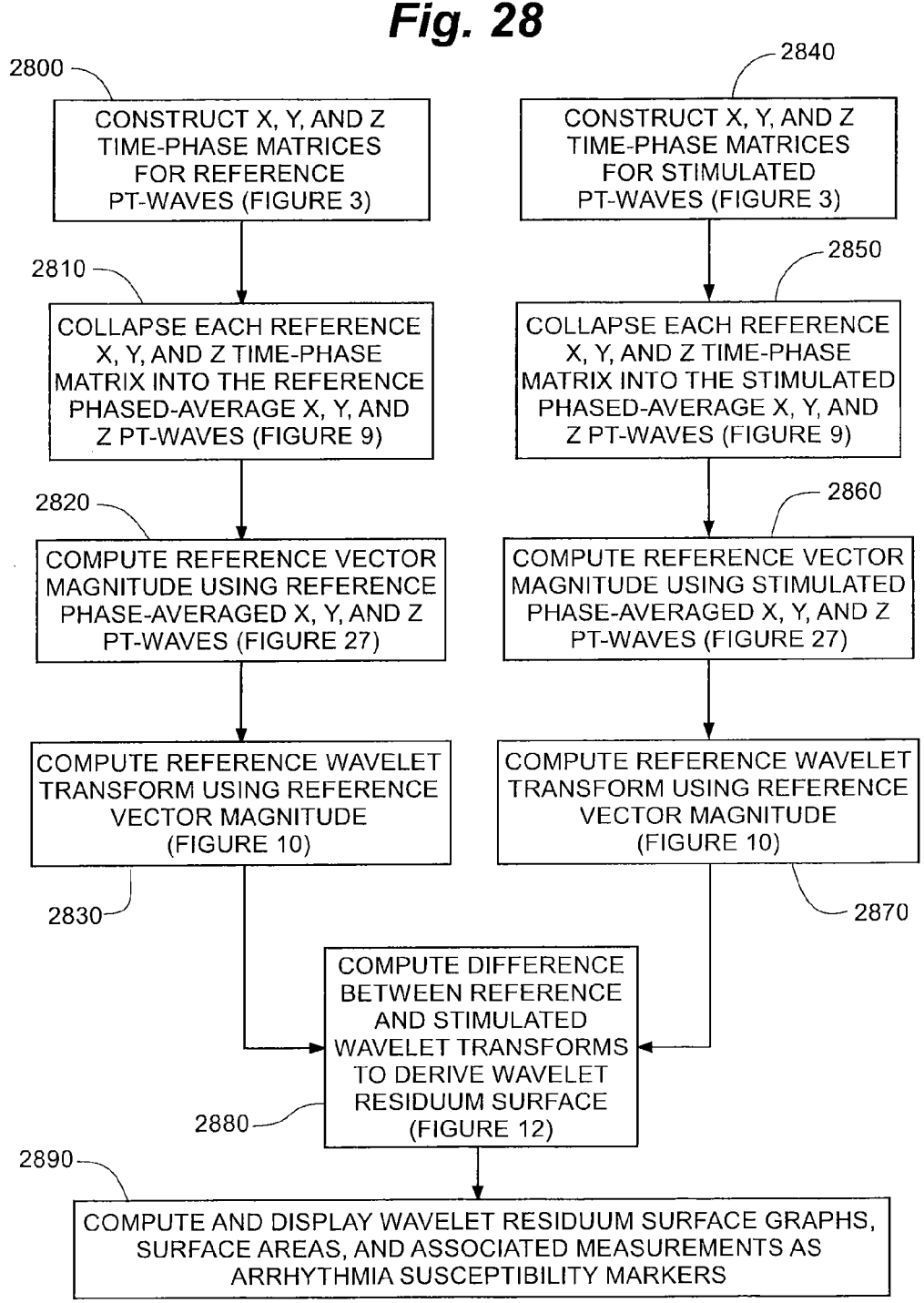
FIG. 28 illustrates a flowchart for a method of analyzing a patient's Wedensky modulated ECG data using time-domain ECG vector magnitudes to determine continuous wavelet-based modulation graphs and associated arrhythmia indices in accordance with the invention.

As an alternative embodiment of the present invention, as a first step following the process of Wedensky modulation and the acquisition of the ECG signals, the present invention's software analysis element 2800 constructs the rTPX, rTPY, and rTPZ time-phase matrices for the reference PT-waves (FIGS. 2 and 3). As a second step, the software analysis element 2810 collapses the reference rTPX, rTPY, and rTPZ time-phase matrices into the reference phase-averaged X, Y, and Z PT-waves illustrated by FIG. 9. As a third step, the software analysis element 2820 computes the reference vector magnitude rVM 2750 of the phase-averaged X 2710, Y 2720, and Z 2730 PT-waves using the vector magnitude operation 2740 and described by formula 2760 for a point t 2704 in time, as illustrated in FIG. 27. For illustrative phase-averaged values X(t) 2714, Y(t) 2724, and Z(t) 2734 the formula 2760 is computed for each vector magnitude value VM(t) 2754. As a fourth step, the software analysis element 2830 computes the reference wavelet vector magnitude, similarly herein labeled rWVM, using the reference time-domain vector magnitude rVM, as illustrated in FIG. 10. FIG. 28, together with FIGS. 3, 9, 27, and 11, further illustrate the software analysis elements 2840, 2850, 2860, and 2870 and their four construction and computation steps to first construct the stimulated sTPX, sTPY, and sTPZ time-phase matrices for the stimulated PT-waves (FIGS. 2 and 3), to second collapse the stimulated sTPX, sTPY, and sTPZ time-phase matrices into the stimulated phase-averaged PT-waves for the X, Y, and Z ECG signals (FIG. 9), to third compute the stimulated vector magnitude sVM of the stimulated phase-averaged X, Y, and Z PT-waves (FIG. 27), and to fourth compute the stimulated wavelet vector magnitude sWVM using the stimulated time-domain vector magnitude sVM (FIG. 10). FIG. 28 further illustrates the software analysis element 2880 that computes the continuous wavelet surface residuum in the same manner that the residuum is computed by analysis element 1880. As a sixth step, the software analysis element 2890 computes and display the residuum, surface area measurements, and statistical comparisons to serve as a set of diagnostic markers.

Figure 29:
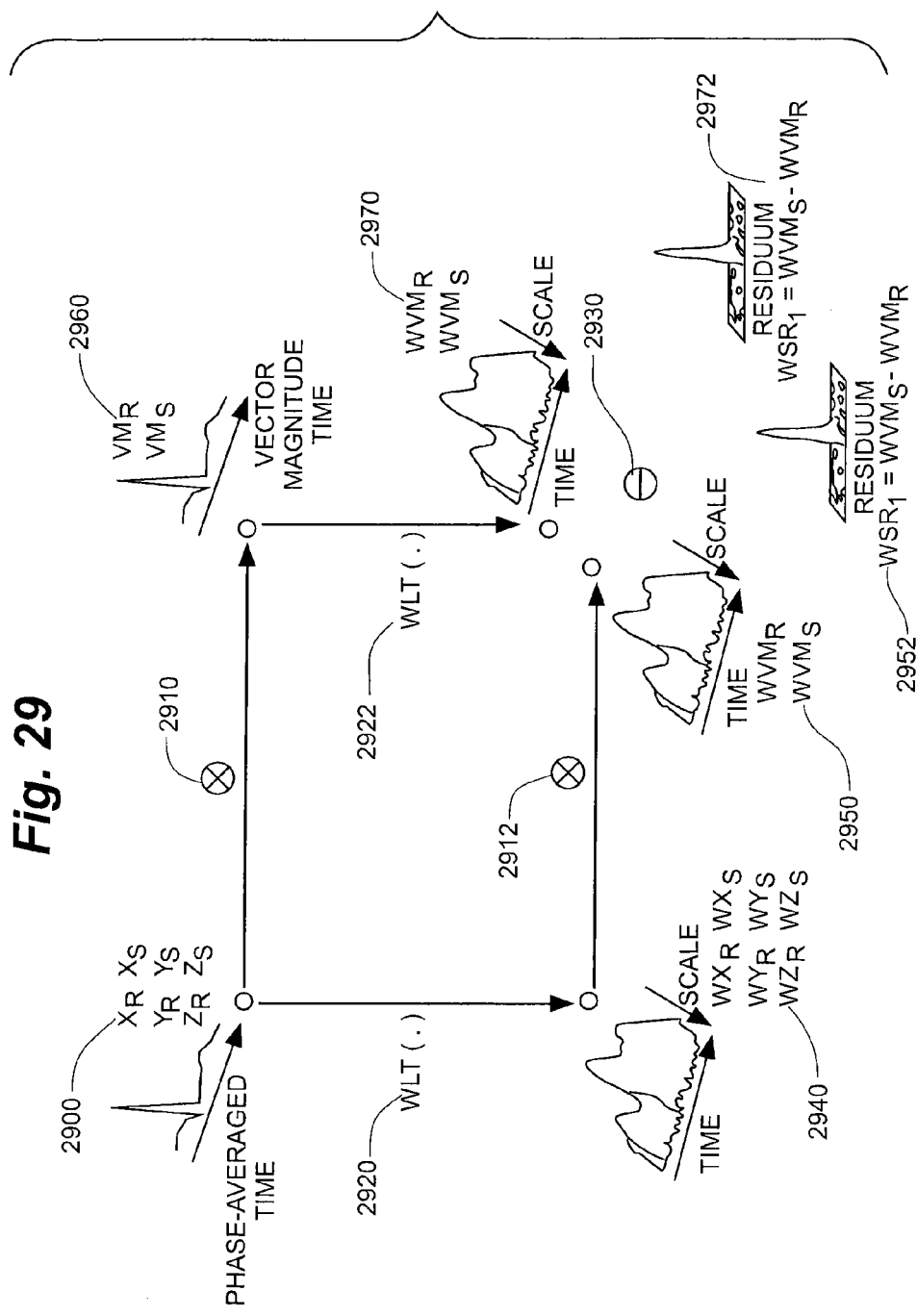
FIG. 29 illustrates process diagrams for vector magnitude methods of analyzing a patient's Wedensky modulated ECG data using time-domain ECG vector magnitudes and using frequency-domain wavelet vector magnitudes to determine wavelet-based modulation graphs and associated arrhythmia indices in accordance with the invention.

FIG. 29 illustrates two of the methods and apparatus of the present invention as illustrated by FIGS. 18 and 28. Each method and apparatus receives the reference phase-averaged PT-waves $X_R$, $Y_R$, and $Z_R$ 2900 derived from the reference time-phase matrices and the stimulated phase-averaged PT-waves $X_S$, $Y_S$, and $Z_S$ 2900 derived from the stimulated time-phase matrices as inputs. The method and apparatus of FIG. 18 is illustrated by first the operational arrow 2920 representing the wavelet transform computation and the derivation of the continuous wavelet transforms 2940 and second the operational arrow 2912 representing the vector magnitude construction and the derivation of the wavelet vector magnitudes 2050. The method and apparatus of FIG. 28 is illustrated by first the operational arrow 2910 representing the vector magnitude construction and the derivation of the time-domain vector magnitudes 2960 and second the operational arrow 2922 representing the continuous wavelet transform computation and the derivation of the continuous wavelet transforms 2970 of the vector magnitudes 2060. Each method and apparatus computes the continuous wavelet surface residuum as output from the difference operation 2930, by subtracting a stimulated wavelet vector magnitude $WVM_S$ from a reference wavelet vector magnitude $WVM_R$. The resulting wavelet surface residuums $WSR_1$ 2952 and $WSR_2$ 2972 are different due to the non-commutative order of the computational steps, and therefore these residuums each contain complementary and balancing diagnostic information and markers regarding a patient's arrhythmia susceptibility. The markers derived from each of these two residuums are combined by averaging, normalized differencing, and ratios to derive new diagnostic markers. Other diagnostic markers derived from a continuous wavelet residuum have been described in this specification and the computation of these markers are applicable to the general residuum pair ($WSR_1$, $WSR_2$). Each of these two methods and apparatus of the present invention process a patient's Wedensky modulated ECG signals using the batch mode of operation and the interleaved mode of operation. The invention interface permits the physician-operator to preselect the method and mode at the start of an alternans analysis and the invention interface permits the physician-operator to perform the analysis using different methods and modes. The results output from each analysis session is stored in the computer and accessible to the physician-operator to display, to print, and to electronically communicate to other physician-operators' networks.

Figure 30:
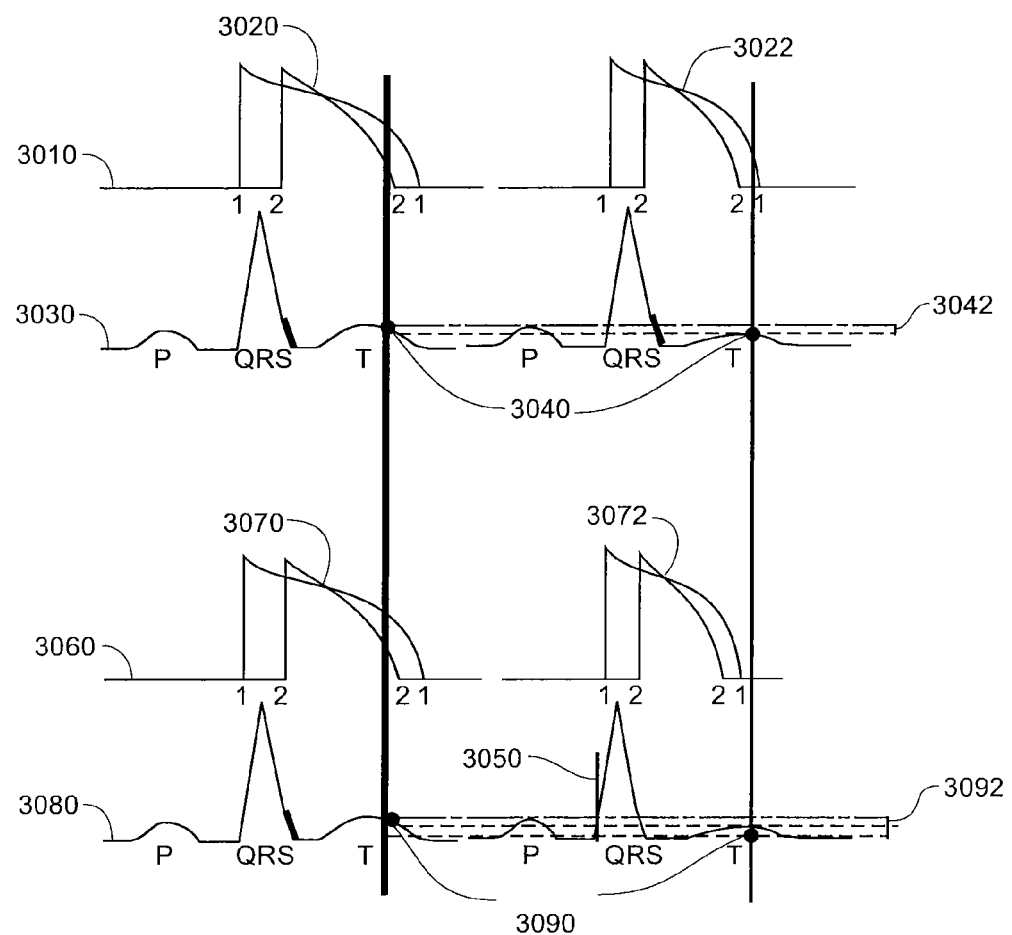
FIG. 30 illustrates effects of Wedensky modulation to the general electrophysiological findings for T-wave alternans at the cellular action potential level in myocardial tissue as measured using an ECG signal in accordance with the invention.

FIG. 30 illustrates the effects of Wedensky modulation to the general electrophysiological findings for T-wave alternans at the cellular action potential levels 3010 and 3060 in myocardial tissue as measured using an ECG signal 3030 and 3080. Naturally-occurring T-wave alternans values 3040 reflect the changes that occur at the cellular level due to cardiac cycle to cardiac cycle changes in the different phases for a myocardial cell's action potentials 3020 and 3022. FIG. 30 illustrates a shortening 3022 of the cellular action potentials for a second cardiac cycle when compared to a first cardiac cycle, as an example of the types of changes that occur at the cellular level. The following third cardiac cycle has a lengthening 3020 of the cellular action potentials similar to the first cardiac cycle, which is then followed by a shortening 3022 of the cellular action potentials in the fourth cardiac cycle similar to the second cardiac cycle. As described in this paragraph and illustrated in FIG. 30, this pattern repeats every two cardiac cycles. Further, the cell to cell changes in depolarization and repolarization are measured using one or more ECG signals 3030 and are analyzed by detecting the cardiac cycle to cardiac cycle changes in R-waves and T-waves as the R-waves and T-waves reflect the cycle to cycle cellular changes. In FIG. 30, these cardiac cycle to cardiac cycle changes 3042 are illustrated for T-waves values 3040. A plurality of prior art teach methods to measure and report the naturally-occurring cycle to cycle T-wave changes 3042 as clinical significant diagnostic markers for arrhythmia susceptibility. These methods determine the cycle to cycle changes 3042 at each time point in the T-wave. In FIG. 30, Wedensky modulation of the cardiac cycles is illustrated by the application of a subthreshold pulse 3050 applied to the second cardiac cycle in the ECG signal 3080. The effect of the subthreshold pulse 3050 is illustrated by example in FIG. 30 by additional shortening 3072 and then lengthening changes 3070 to cycle to cycle repolarization. These example changes 3070 and 3072 in cycle to cycle repolarization are illustrated for T-waves values 3090 and produce significant cycle to cycle changes 3092 in the T-wave that are measured in an ECG signal and that are significantly different from the alternating cycle to cycle changes 3042 in the T-wave that occur naturally (without Wedensky modulation). The present invention determines the significantly different cycle to cycle changes 3092 that occur at each time point in the T-wave due to Wedensky modulation.

Figure 31:
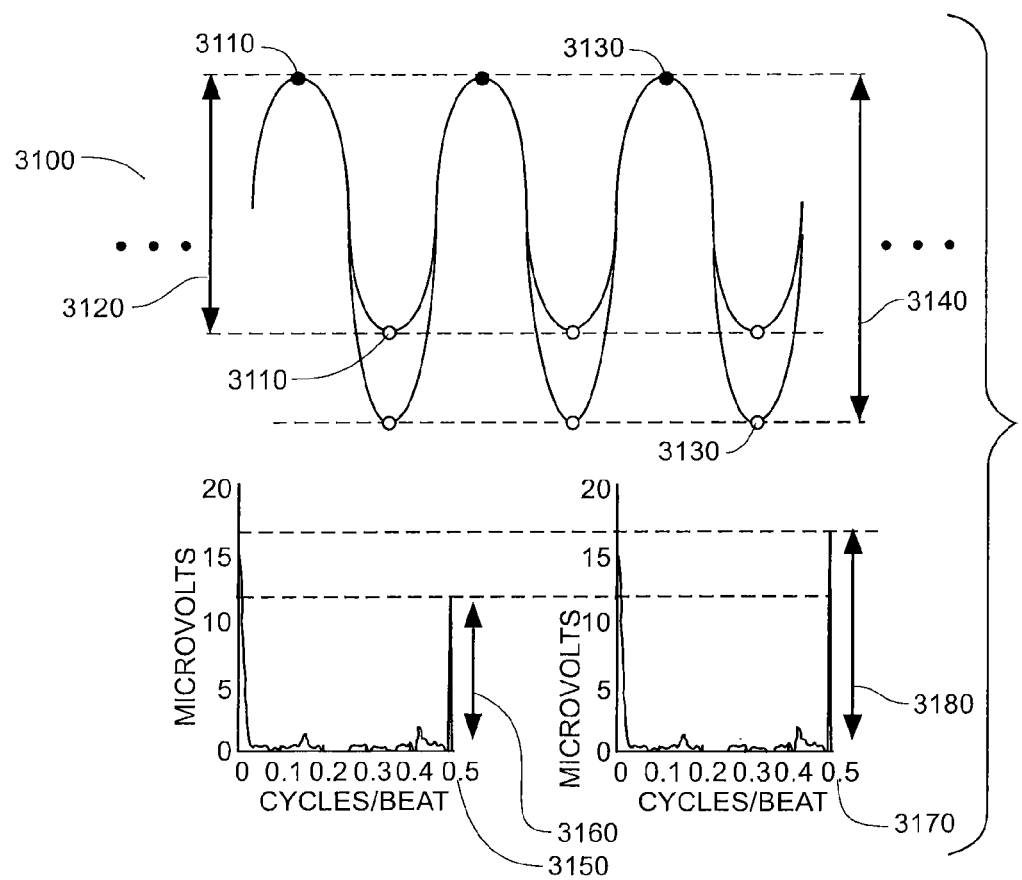
FIG. 31 illustrates effects of Wedensky modulation to general electrophysiological findings for T-wave alternans at the digital signal processing level of an ECG signal as measured using Fourier transform methodology in accordance with the invention.

To further illustrate the present invention, FIG. 31 illustrates the effects of Wedensky modulation to the general electrophysiological findings for T-wave alternans at the digital signal processing level of an ECG signal as measured using Fourier transform methodology. FIG. 31 illustrates a plot 3100 of the naturally-occurring voltage values 3110 and the Wedensky modulated voltage values 3130 in an ECG signal for a single time point in the T-wave from one cardiac cycle to a next cardiac cycle, described in this specification as the phase dimension. The naturally-occurring cycle to cycle changes 3120 in the T-wave are illustrated by the difference between one T-wave voltage value 3110 to a next T-wave voltage value 3110 for a fixed point in time. The Wedensky modulated cycle to cycle changes 3140 in the T-wave are illustrated by the amplified difference that occurs between one T-wave voltage value 3130 to a next T-wave voltage value 3130 for a fixed point in time. The differences between measuring T-wave alternans that occur naturally and measuring T-wave alternans that occur due to Wedensky modulation are further illustrated in FIG. 31 by the plots 3150 and 3170 of the Fourier transforms of the T-wave voltage values 3110 and 3130 in the phase dimension for a fixed time point in the T-wave. Due to the differences between naturally-occurring alternans and Wedensky modulated alternans, the spectral measurement 3160 for naturally-occurring T-wave alternans is different from the spectral measurement 3180 for Wedensky modulated T-wave alternans.

As alternate embodiments of the present invention, the alternans energy values derived from the power spectrum computed by using the Fourier transform can also be computed by one of several frequency-domain methods. The present invention's method for computing the power spectrum is a method of spectral analysis, in which spectral analysis is described as any signal processing method that characterizes the frequency or periodicity content of a measured signal.

In the present invention, the signal processing method for estimating or deriving the alternans energy values from a patient's ECG signal is the power spectrum (also known as the power spectral density, the energy spectral density, and the periodogram, which is the square of the modulus of the Fourier transform and is classified as a non-parametric method for estimating second-order statistics). In the present invention, the measured signal is the phase-dimension of an ECG signal derived from a patient and constructed within a time-phase matrix. A method for computing the non-parametric power spectral density is the fast Fourier transform (FFT). The method of the power spectrum determines the periodicities of the measured phase-domain of a patient's ECG signal and uses one or more of the computed periodicity values as an alternans energy value. Other spectral analytic methods also measure a signal's periodicity and are used in the alternate embodiments. These other non-parametric spectral analytic methods are the Daniel periodogram, the Bartlett periodogram, the Welch pieriodogram, and the correlation power spectral density method. Parametric methods for estimating second-order statistics for a signal are the autoregressive (AR) model, the moving average (MA) model, and the autoregressive moving average (ARMA) model. A method for computing the AR and ARMA model power spectral densities is the Levinson algorithm. Another class of methods for computing the AR and ARMA model power spectral densities is the class of sequential algorithms for adaptive AR and ARMA parameter estimation, which fall into two categories. The first category is defined by the gradient approximation approach and includes the least-mean-square (LMS) algorithm. The second category is defined by the recursive-least-squares (RLS) algorithms. Each of these spectral analytic methods computes the value for the periodicities of a measured signal and is therefore appropriate for use in the present invention to measure one or more alternans energy values from a patient's ECG signal. A reference for these methods is Kay S M, Modern Spectral Estimation, Theory and Application, Prentice Hall, Englewood Cliffs, N.J., 1988.

Further, as alternative embodiments of the present invention, the alternans energy values derived from the two-dimensional wavelet transform analysis can also be computed by one of several time-frequency domain methods. Other spectral analytic methods are the short-time Fourier (STFT) transform, the Wigner-Ville transform, the exponential (Choi-Williams) transform, the cone kernel (Zhao-Atlas-Marks) transform, and the reduced interference transform. Each of these methods are members of the Cohen class of time-frequency representations of a signal's time-frequency content. Other time-frequency methods employ fixed kernel or adaptive kernel designs. The squares of the time-frequency representations also provide methods for computing alternans energy values. The square of the wavelet transform representation is called the scalogram and the square of the STFT transform representation is called the spectrogram. A reference for these methods is Akay M, editor, Time Frequency and Wavelets in Biomedical Signal Processing, IEEE Press, Piscataway, N.J., 1998.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

We claim:

1. A method of assessing a patient's susceptibility to ventricular arrhythmia, comprising: obtaining data by
    applying electrodes to the patient, the electrodes being adapted to detect electrocardiographic signals from the patient;
    selectively delivering a plurality of subthreshold electrical stimuli into the patient's body that are synchronized to a plurality of selected cardiac cycles to present stimulated cardiac cycles to the electrodes such that other unselected cardiac cycles are unstimulated to present unstimulated reference cardiac cycles to the electrodes;

using the electrodes to record a plurality of the electrocardiographic signals including the stimulated cardiac cycles and the unstimulated reference cardiac cycles;

analyzing the plurality of electrocardiographic signals that are recorded by creating a matrix of vectorized time-phase data representing a plurality cardiac cycles contained in the electrocardiographic signals that are recorded;

processing the matrix to generate spectral analytic representation of the matrix;

analyzing at least the spectral analytic representation to determine at least one alternans index for the patient; and displaying the at least one alternans index as an indicator of the patient's susceptibility to arrhythmia.

2. The method of assessing a patient's susceptibility to ventricular arrhythmia as claimed in claim 1, wherein creating, processing and analyzing further comprise:

constructing at least two stimulated time phase matrices from the stimulated cardiac cycles including at least one stimulated time phase matrix for each electrocardiographic signal;

constructing at least two reference time phase matrices from the reference cardiac cycles including at least one reference time phase matrix for each electrocardiographic signal;

computing a stimulated vector magnitude time phase matrix from the stimulated time-phase matrices from the stimulated time-phase matrices;

computing a reference vector magnitude time phase matrix from the reference time-phase matrices;

computing power spectra for each phase dimension column in each stimulated time phase matrix and each phase dimension column in the stimulated vector magnitude time phase matrix;

computing power spectra for each phase dimension column in each reference time phase matrix and each phase dimension column in the reference vector magnitude time phase matrix;

constructing alternans energy curves for each stimulated time phase matrix and each stimulated vector magnitude time phase matrix;

constructing alternans energy curves for each reference time phase matrix and each reference vector magnitude time phase matrix;

computing stimulated alternans indices from the stimulated alternans energy curves;

computing reference alternans indices from the reference alternans energy curves; and computing comparative alternans indices by comparing the stimulated alternans indices and the reference alternans indices thereby assessing the patients susceptibility to arrhythmias.

3. The method of assessing a patient's susceptibility to ventricular arrhythmia as claimed in claim 2, wherein analyzing further comprises performing wavelet analysis of the stimulated and reference alternans energy curves.

4. The method of assessing a patient's susceptibility to ventricular arrhythmia as claimed in claim 3, wherein analyzing further comprises:

computing a stimulated wavelet transform for at least one of the stimulated alternans energy curves;

computing a reference wavelet transform for at least one of the reference alternans energy curves;

computing a difference between the at least one stimulated and the at least one reference wavelet transform to derive for at least one wavelet residuum surface;

computing a plurality of wavelet residuum surface area elements; and displaying a graph of the for at least one wavelet residuum surface graph, and a plurality of surface area elements.

5. The method of assessing a patient's susceptibility to ventricular arrhythmia as claimed in claim 1, wherein analyzing further comprises processing the matrix in a batch mode.

6. The method of assessing a patient's susceptibility to ventricular arrhythmia as claimed in claim 1, wherein analyzing further comprises processing the matrix in an interleaved mode.

7. The method of assessing a patient's susceptibility to ventricular arrhythmia as claimed in claim 1, wherein analyzing further comprises:

constructing a plurality of interleaved stimulated-reference time-phase matrices from the recorded stimulated cardiac cycles and unstimulated reference cardiac cycles, one interleaved stimulated-reference time-phase matrix for each orthogonal electrocardiographic signal;

computing an interleaved stimulated-reference vector magnitude time-phase matrix from the interleaved stimulation-reference time-phase matrices;

computing power spectra for each phase dimension column in each interleaved stimulated-reference time-phase matrix and each phase dimension column in the interleaved stimulated-reference vector magnitude time-phase matrix;

constructing differential alternans energy curves for the interleaved stimulated-reference time-phase matrices and the interleaved stimulated-reference vector magnitude time-phase matrix; and computing differential alternans indices from the differential alternans energy curves thereby assessing the patients susceptibility to arrhythmias.

8. The method of assessing a patient's susceptibility to ventricular arrhythmia as claimed in claim 7, wherein analyzing further comprises performing wavelet analysis of the differential alternans energy curves.

9. The method of assessing a patient's susceptibility to ventricular arrhythmia as claimed in claim 7, wherein analyzing further comprises:

computing Morlet wavelet based wavelet transforms of the alternans energy curves of the interleaved stimulated-reference time-phase matrix and the interleaved stimulated-reference vector magnitude time-phase matrix; and computing alternans indices derived from combination methods related to wavelet packet tiling.

10. The method of assessing a patient's susceptibility to ventricular arrhythmia as claimed in claim 7, wherein analyzing further comprises applying Fourier transform methodology.

11. The method of assessing a patient's susceptibility to ventricular arrhythmia as claimed in claim 7, wherein analyzing further comprises applying continuous wavelet transform methods.

12. The method of assessing a patient's susceptibility to ventricular arrhythmia as claimed in claim 11, wherein applying continuous wavelet transform methods comprises applying a continuous wavelet transform.

13. The method of assessing a patient's susceptibility to ventricular arrhythmia as claimed in claim 11, wherein applying continuous wavelet transform methods comprises applying a discrete wavelet transform.

14. The method of assessing a patient's susceptibility to ventricular arrhythmia as claimed in claim 11, wherein applying continuous wavelet transform methods comprises applying a wavelet packet transform.

15. The method of assessing a patient's susceptibility to ventricular arrhythmia as claimed in claim 7, wherein analyzing further comprises applying a weighting scheme using a multiresolution algorithm and a wavelet packet transform to a wavelet tiling representation.

16. The method of assessing a patient's susceptibility to ventricular arrhythmia as claimed in claim 15, wherein the weighting scheme comprises sorting wavelet packet coefficients from largest value to smallest value, selecting a plurality of coefficients larger than a predetermined coefficient threshold value, and summing the selected coefficients to form an alternans energy curve index.

17. The method of assessing a patient's susceptibility to ventricular arrhythmia as claimed in claim 15, wherein the weighting scheme comprises computing an entropy value for each wavelet packet coefficient, sorting wavelet packet coefficient entropy values from smallest to largest, selecting a plurality of coefficients smaller than a predetermined entropy threshold value, and summing the selected coefficients to form an alternans energy curve index.

18. The method of assessing a patient's susceptibility to ventricular arrhythmia as claimed in claim 1, wherein analyzing further comprises eliminating data for outlier cardiac cycles in pairs.

19. The method of assessing a patient's susceptibility to ventricular arrhythmia as claimed in claim 1, further comprising delivering the subthreshold cardiac signal to an R-wave of the electrocardiographic signals.

20. The method of assessing a patient's susceptibility to ventricular arrhythmia as claimed in claim 1, further comprising delivering the subthreshold cardiac signal to a T-wave of the electrocardiographic signals.

21. The method of assessing a patient's susceptibility to ventricular arrhythmia as claimed in claim 1, further comprising delivering the subthreshold cardiac signal to a P-wave of the electrocardiographic signals.

22. A device to assess a patient's susceptibility to ventricular arrhythmia, comprising:
    electrodes adapted to detect electrocardiographic signals from the patient;
    means for selectively delivering a plurality of subthreshold electrical stimuli into the patient's body that are synchronized to a plurality of selected cardiac cycles to present stimulated cardiac cycles to the electrodes such that other unselected cardiac cycles are unstimulated to present unstimulated reference cardiac cycles to the electrodes;
    means for recording a plurality of the electrocardiographic signals including the stimulated cardiac cycles and the unstimulated reference cardiac cycles;
    means for analyzing the plurality of electrocardiographic signals that are recorded by creating a matrix of vectorized time-phase data representing a plurality cardiac cycles contained in the electrocardiographic signals that are recorded;
    means for processing the matrix to generate spectral analytic representation of the matrix;
    means for analyzing at least the spectral analytic representation to determine at least one alternans index for the patient; and
    means for displaying the at least one alternans index as an indicator of the patient's susceptibility to arrhythmia.

23. The device to assess a patient's susceptibility to ventricular arrhythmia as claimed in claim 22, wherein the means for creating, processing and analyzing further comprise:
    means for constructing at least two stimulated time phase matrices from the stimulated cardiac cycles including at least one stimulated time phase matrix for each electrocardiographic signal;
    means for constructing at least two reference time phase matrices from the reference cardiac cycles including at least one reference time phase matrix for each electrocardiographic signal;
    means for computing a stimulated vector magnitude time phase matrix from the stimulated time-phase matrices from the stimulated time-phase matrices;
    means for computing a reference vector magnitude time phase matrix from the reference time-phase matrices;
    means for computing power spectra for each phase dimension column in each stimulated time phase matrix and each phase dimension column in the stimulated vector magnitude time phase matrix;
    means for computing power spectra for each phase dimension column in each reference time phase matrix and each phase dimension column in the reference vector magnitude time phase matrix;
    means for constructing alternans energy curves for each stimulated time phase matrix and each stimulated vector magnitude time phase matrix;
    means for constructing alternans energy curves for each reference time phase matrix and each reference vector magnitude time phase matrix;
    means for computing stimulated alternans indices from the stimulated alternans energy curves;
    means for computing reference alternans indices from the reference alternans energy curves; and
    means for computing comparative alternans indices by comparing the stimulated alternans indices and the reference alternans indices thereby assessing the patients susceptibility to arrhythmias.

24. The device to assess a patient's susceptibility to ventricular arrhythmia as claimed in claim 22, wherein the means for analyzing further comprises means for performing wavelet analysis of the stimulated and reference alternans energy curves.

25. The device to assess a patient's susceptibility to ventricular arrhythmia as claimed in claim 24, wherein the means for analyzing further comprises:
    means for computing a stimulated wavelet transform for at least one of the stimulated alternans energy curves;
    means for computing a reference wavelet transform for at least one of the reference alternans energy curves;
    means for computing a difference between for at least one stimulated and reference wavelet transforms to derive for at least one wavelet residuum surface;
    means for computing a plurality of wavelet residuum surface area elements; and
    means for displaying a graph of the for at least one wavelet residuum surface graph, and a plurality of surface area elements.

26. The device to assess a patient's susceptibility to ventricular arrhythmia as claimed in claim 22, wherein the means for analyzing further comprises means for processing the matrix in a batch mode.

27. The device to assess a patient's susceptibility to ventricular arrhythmia as claimed in claim 22, wherein the means for analyzing further comprises means for processing the matrix in an interleaved mode.

28. The device to assess a patient's susceptibility to ventricular arrhythmia as claimed in claim 22, wherein the means for analyzing further comprises:
- means for constructing a plurality of interleaved stimulated-reference time-phase matrices from the recorded stimulated cardiac cycles and unstimulated reference cardiac cycles, one interleaved stimulated-reference time-phase matrix for each orthogonal electrocardiographic signal;
- means for computing an interleaved stimulated-reference vector magnitude time-phase matrix from the interleaved stimulation-reference time-phase matrices;
- means for computing power spectra for each phase dimension column in each interleaved stimulated-reference time-phase matrix and each phase dimension column in the interleaved stimulated-reference vector magnitude time-phase matrix;
- means for constructing differential alternans energy curves for the interleaved stimulated-reference time-phase matrices and the interleaved stimulated-reference vector magnitude time-phase matrix; and
- means for computing differential alternans indices from the differential alternans energy curves thereby assessing the patients susceptibility to arrhythmias.

29. The device to assess a patient's susceptibility to ventricular arrhythmia as claimed in claim 28, wherein the means for analyzing further comprises means for performing wavelet analysis of the differential alternans energy curves.

30. The device to assess a patient's susceptibility to ventricular arrhythmia as claimed in claim 28, wherein the means for analyzing further comprises:
- means for computing Morlet wavelet based wavelet transforms of the alternans energy curves of the interleaved stimulated-reference time-phase matrix and the interleaved stimulated-reference vector magnitude time-phase matrix; and
- means for computing alternans indices derived from combination methods related to wavelet packet tiling.

31. The device to assess a patient's susceptibility to ventricular arrhythmia as claimed in claim 28, wherein the means for analyzing further comprises means for applying Fourier transform methodology to the process.

32. The device to assess a patient's susceptibility to ventricular arrhythmia as claimed in claim 28, wherein the means for analyzing further comprises means applying continuous wavelet transform methods.

33. The device to assess a patient's susceptibility to ventricular arrhythmia as claimed in claim 32, wherein the means for applying continuous wavelet transform methods comprises means for applying a continuous wavelet transform.

34. The device to assess a patient's susceptibility to ventricular arrhythmia as claimed in claim 32, wherein the means for applying continuous wavelet transform methods comprises means for applying a discrete wavelet transform.

35. The device to assess a patient's susceptibility to ventricular arrhythmia as claimed in claim 32, wherein the means for applying continuous wavelet transform methods comprises means for applying a wavelet packet transform.

36. The device to assess a patient's susceptibility to ventricular arrhythmia as claimed in claim 28, wherein the means for analyzing further comprises means for applying weighting schemes using a multiresolution algorithm and a wavelet packet transform to a wavelet tiling representation.

37. The device to assess a patient's susceptibility to ventricular arrhythmia as claimed in claim 36, wherein the weighting scheme comprises sorting wavelet packet coefficients from a largest value to a smallest value, selecting a plurality of coefficients larger than a predetermined coefficient threshold value, and summing the selected plurality of coefficients, wherein the sum of the coefficients forms an alternans energy curve index.

38. The device to assess a patient's susceptibility to ventricular arrhythmia as claimed in claim 36, wherein the weighting scheme comprises computing an entropy value for each wavelet packet coefficient, sorting the wavelet packet coefficient entropy values from smallest value to largest value, selecting a plurality of coefficients based on a coefficient's entropy value smaller than a predetermined entropy threshold value, and summing the selected plurality of coefficients, wherein the sum of the coefficients forms an alternans energy curve index.

39. The device to assess a patient's susceptibility to ventricular arrhythmia as claimed in claim 22, wherein the means for analyzing further comprises means for eliminating data for outlier cardiac cycles in pairs.

40. The device to assess a patient's susceptibility to ventricular arrhythmia as claimed in claim 22, further comprising means for delivering the subthreshold cardiac signal to an R-wave of the electrocardiographic signals.

41. The device to assess a patient's susceptibility to ventricular arrhythmia as claimed in claim 22, further comprising means for delivering the subthreshold cardiac signal to a T-wave of the electrocardiographic signals.

42. The device to assess a patient's susceptibility to ventricular arrhythmia as claimed in claim 22, further comprising means for delivering the subthreshold cardiac signal to a P-wave of the electrocardiographic signals.

* * * * *